US008367356B2

(12) United States Patent
Shen et al.

(10) Patent No.: US 8,367,356 B2
(45) Date of Patent: Feb. 5, 2013

(54) GELSOLIN BINDING AGENT COMPOSITIONS AND USES OF SAME

(75) Inventors: Enyun Shen, Beijing (CN); Zheng Yu, Beijing (CN); Min Zhou, Beijing (CN); Fei Guo, Beijing (CN)

(73) Assignee: Beijing Cotimes Biotech Co., Ltd., Beijing (CN)

( * ) Notice: Subject to any disclaimer, the term of this patent is extended or adjusted under 35 U.S.C. 154(b) by 227 days.

(21) Appl. No.: 12/673,134

(22) PCT Filed: Aug. 15, 2007

(86) PCT No.: PCT/CN2007/002467
§ 371 (c)(1),
(2), (4) Date: Feb. 11, 2010

(87) PCT Pub. No.: WO2009/021360
PCT Pub. Date: Feb. 19, 2009

(65) Prior Publication Data
US 2011/0207152 A1    Aug. 25, 2011

(51) Int. Cl.
*C07K 16/18* (2006.01)
*C07K 16/40* (2006.01)
*C12N 5/20* (2006.01)
*G01N 33/53* (2006.01)
*G01N 33/543* (2006.01)
*G01N 33/563* (2006.01)
*G01N 33/573* (2006.01)
*G01N 33/577* (2006.01)

(52) U.S. Cl. .......... 435/7.94; 424/9.1; 435/7.1; 435/7.4; 435/7.92; 435/7.95; 435/70.21; 435/331; 435/337; 435/338; 436/501; 436/512; 436/518; 436/548; 436/811; 530/387.9; 530/388.25; 530/388.26; 530/391.1; 530/391.3

(58) Field of Classification Search ............. 435/7.1, 435/7.4, 7.8, 7.92, 7.94, 7.95, 70.21, 331, 435/337, 338; 436/501, 518, 547, 548, 811, 436/512; 530/387.9, 388.25, 388.26, 389.3, 530/391.1, 391.3; 424/9.1
See application file for complete search history.

(56) References Cited

U.S. PATENT DOCUMENTS

| 5,648,465 A | 7/1997 | Margolis |
| 5,650,487 A | 7/1997 | Chang |
| 6,271,353 B1 | 8/2001 | Nakamura et al. |
| 2007/0238655 A1* | 10/2007 | Bucki et al. ............ 514/12 |
| 2010/0227807 A1* | 9/2010 | Stossel et al. ........... 514/12 |

FOREIGN PATENT DOCUMENTS

| CN | 1746676 | * | 3/2006 |
| WO | WO 2005014635 A2 | | 2/2005 |
| WO | WO 2006091861 A2 | | 8/2006 |
| WO | WO 2007/109056 | | 9/2007 |
| WO | WO-2007/137582 | | 12/2007 |

OTHER PUBLICATIONS

Hellström et al., 1985. In Monoclonal Antibodies for Cancer Detection and Therapy (Baldwin et al, eds.), Academic Press, London. p. 20.*
Ulrike Fock et al: "Topological assignment of the N-terminal extension of plasma gelsolin to the gelsolin surface", Biochem. J., 2005, vol. 385, pp. 659-665.
Lorraine E. Laham et al: "Identification of two sites in gelsolin with different sensitivities to adenine nucleotides", Eur. J. Biochem., 1995, vol. 234, pp. 1-7.
International Search Report and Written Opinion for PCT/CN2007/002467 mailed May 29, 2008.
International Search Report and Written Opinion for PCT/CN2008/072005 mailed Nov. 27, 2008.
International Preliminary Report on Patentability issued in PCT/CN2008/072005 and mailed Feb. 25, 2010.
International Preliminary Report on Patentability issued in PCT/CN2007/002467 and mailed on Feb. 25, 2010.
Asch, H. L. et al., "Down-regulation of gelsolin expression in human breast ductal carcinoma in situ with and without invasion", *Breast Cancer Research and Treatment*, (May 1, 1999), vol. 55, No. 2, pp. 179-188, Kluwer Academic Publishers.
Cabello-Agueros, Jose F. et al., "The Role of F-Actin Cytoskeleton-Associated Gelsolin in the Guinea Pig Capacitation and Acrosome Reaction", *Cell Motility and the Cytoskeleton*, (Oct. 2003), vol. 56, No. 2, pp. 94-108.
Extended European Supplementary Search Report for European Pat. Appln. No. 07785362.0, mailed on Feb. 28, 2011, 14 pp.
Hiyoshi, M. et al., "Comparison of Two Monoclonal Antibodies, H6B11 and GS2C4, Against Human Plasma Gelsolin", *Biochemistry and Molecular Biology International*, (Mar. 1994), vol. 32, No. 4, pp. 755-762.
Hwo, S. et al., "Immuno-identification of $CA^{2+}$-induced Conformational Changes in Human Gelsolin and Brevin", *The Journal of Cell Biology*, (Jan. 1986), vol. 102, pp. 227-236.
Lee, Po-Shun, M.D. et al, "Plasma gelsolin is a marker and therapeutic agent in animal sepsis", *Critical Care Medicine*, (2007), vol. 35, No. 3, pp. 849-855, Williams and Wilkings Company, Baltimore, MA, US.
Mounzer, K. C. et al., "Relationship of Admission Plasma Gelsolin Levels to Clinical Outcomes in Patients after Major Trauma", *American Journal of Respiratory and Critical Care Medicine*, (Jan. 1, 1999), vol. 160, No. 5, pp. 1673-1681.
Smith, D. B., M.D. et al., "Circulating Actin-Gelsolin Complexes Following Oleic Acid-Induced Lung Injury", *American Journal of Pathology*, (Feb. 1988), vol. 130, No. 2, pp. 261-267.

(Continued)

*Primary Examiner* — Gail R Gabel
*Assistant Examiner* — James L Grun
(74) *Attorney, Agent, or Firm* — Foley & Lardner LLP

(57) ABSTRACT

The invention relates generally to gelsolin binding agents (e.g., antibodies) which can bind to gelsolin polypeptides. Gelsolin binding agents of the invention are useful, alone or in combination, to detect a gelsolin polypeptide (a.k.a., the target polypeptide) in a test sample as well as to purify native gelsolin proteins. Gelsolin binding agents are also useful to diagnose, a gelsolin related medical condition in subjects in need thereof. Kits to detect gelsolin in biological samples are provided by the present invention.

13 Claims, 29 Drawing Sheets

OTHER PUBLICATIONS

Suhler, Eric, M.D. et al., "Decreased plasma gelsolin concentrations in acute liver failure, myocardial infarction, septic shock, and myonecrosis", *Critical Care Medicine*, (Apr. 1, 1997), vol. 25, No. 4, pp. 594-598, Williams and Wilkins Company, Baltimore, MD, US.

Thor, Ann D. et al., Gelsolin as a Negative Prognostic Factor and Effector of Motility in erbB-2-positive Epidermal Growth Factor Receptor-positive Breast Cancers, *Clinical Cancer Research*, (Aug. 2001), vol. 7, Cover Sheet and pp. 2415-2424, American Association for Cancer Research.

Yang, Jun et al., "Prognostic significance of MCM2, Ki-67 and gelsolin in non-small cell lung cancer", *BMC Cancer*, (Aug. 1, 2006), vol. 6:203, 10 pp., BioMed Central Ltd.

Grossman H. Barton et al., "Surveillance for recurrent bladder cancer using a point-of-care proteomic assay", *JAMA: The Journal of the American Medical Association*, Jan. 2006, vol. 295, No. 3, pp. 299-305.

Han, W. K. et al., "Kidney injury molecule-1 (KIM-1): A novel biomarker for human renal proximal tubule injury", *Kidney International*, Jul. 2002, vol. 62. No. 1, pp. 237-244, Nature Publishing Group, London, GB.

Krishna J. et al., "Urinary protein expression patterns in children with sleep-disordered breathing: Preliminary findings", *Sleep Medicine*, Apr. 2006, vol. 7, No. 3, pp. 221-227, Elsevier, Amsterdam, NL.

Rasmussen et al., "Towards a comprehensive database of proteins from the urine of patients with bladder cancer", *Journal of Urology*, Jun. 1996, vol. 155, No. 6, pp. 2113-2119, Lippincott Williams & Wilkins, Baltimore, MD, US.

Supplementary European Search Report—(EP 08783996) mailed on Jun. 7, 2011 (16 pages).

Vanhoutte Kurt J. A. et al., "Biomarker discovery with SELDI-TOF MS in human urine associated with early renal injury: Evaluation with computational analytical tools", *Nephrology Dialysis Transplantation*, Jul. 2007, vol. 22, No. 10, pp. 2932-2943.

International Preliminary Report on Patentability issued in PCT/CN2008/072005 and mailed on Feb. 25, 2010 (7 pages).

International Preliminary Report on Patentability issued in PCT/CN2007/002467 and mailed on Feb. 25, 2010 (9 pages).

Examination Report received for European Patent Application No. 07785362.0 dated Jun. 29, 2012.

Lind, S.E., et al., "Depression of Gelsolin Levels and Detection of Gelsolin-Actin Complexes in Plasma of Patients with Acute Lung Injury," XP-001041297, Actin and Gelsolin in Acute Lung Injury, Aug. 1988, pp. 429-434.

Office Action issued in Chinese Patent Application No. 200880110871.1 and issued May 3, 2012 (*English language summary provided*).

European Communication received in EP Appln. No. 08783996.5 dated Jul. 11, 2012.

Maury, C.P.J., et al., "Danish type gelsolin related amyloidosis: 654G-T mutation is associated with a disease pathogenetically and clinically similar to that caused by the 654G-A mutation (familial amyloidosis of the Finnish type)," J. Clin. Pathol., 2000, vol. 53, pp. 95-99.

Maury, C.P.J., et al., Identification of the Circulating Amyloid Precursor and Other Gelsolin Metabolites in Patients with G654A Mutation in the Gelsolin Gene (Finnish Familial Amyloidosis): Pathogenetic and Diagnostic Implications, 1997, vol. 77, No. 3, pp. 299-304.

Non-final Office Action received for U.S. Appl. No. 12/673,139 dated Sep. 11, 2012.

* cited by examiner

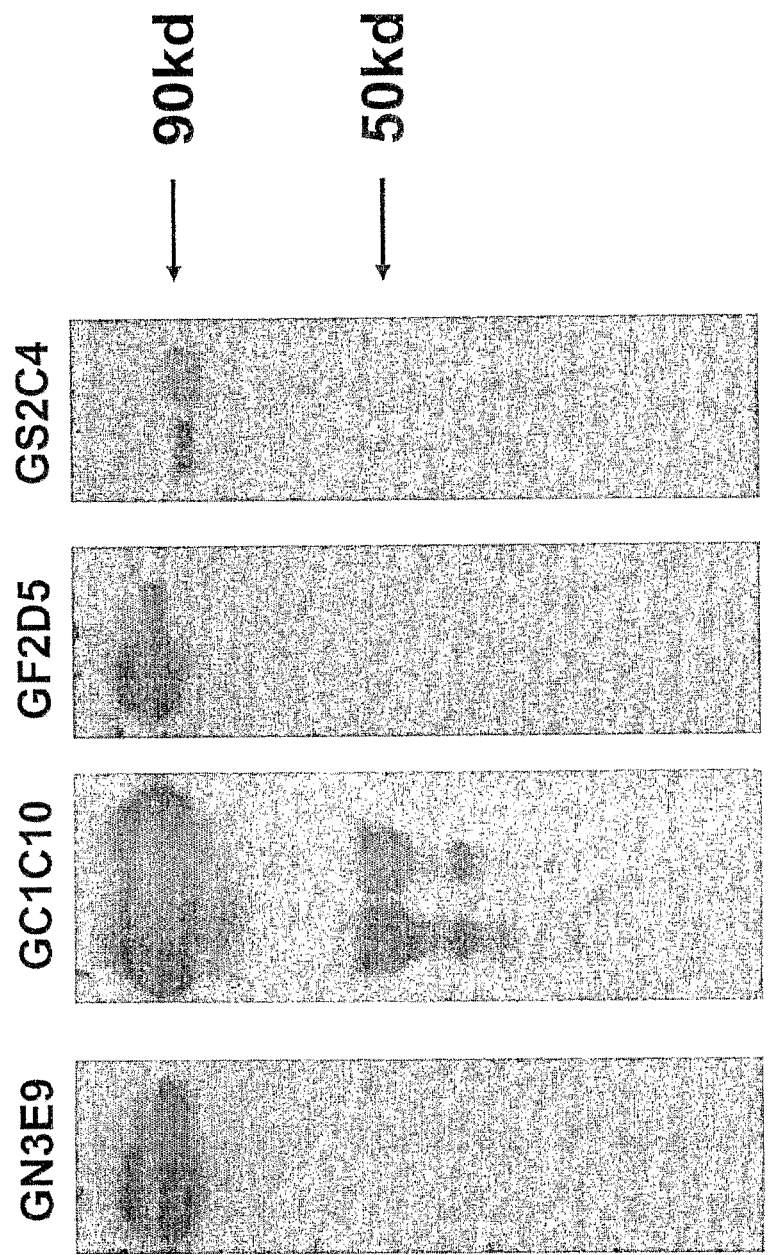

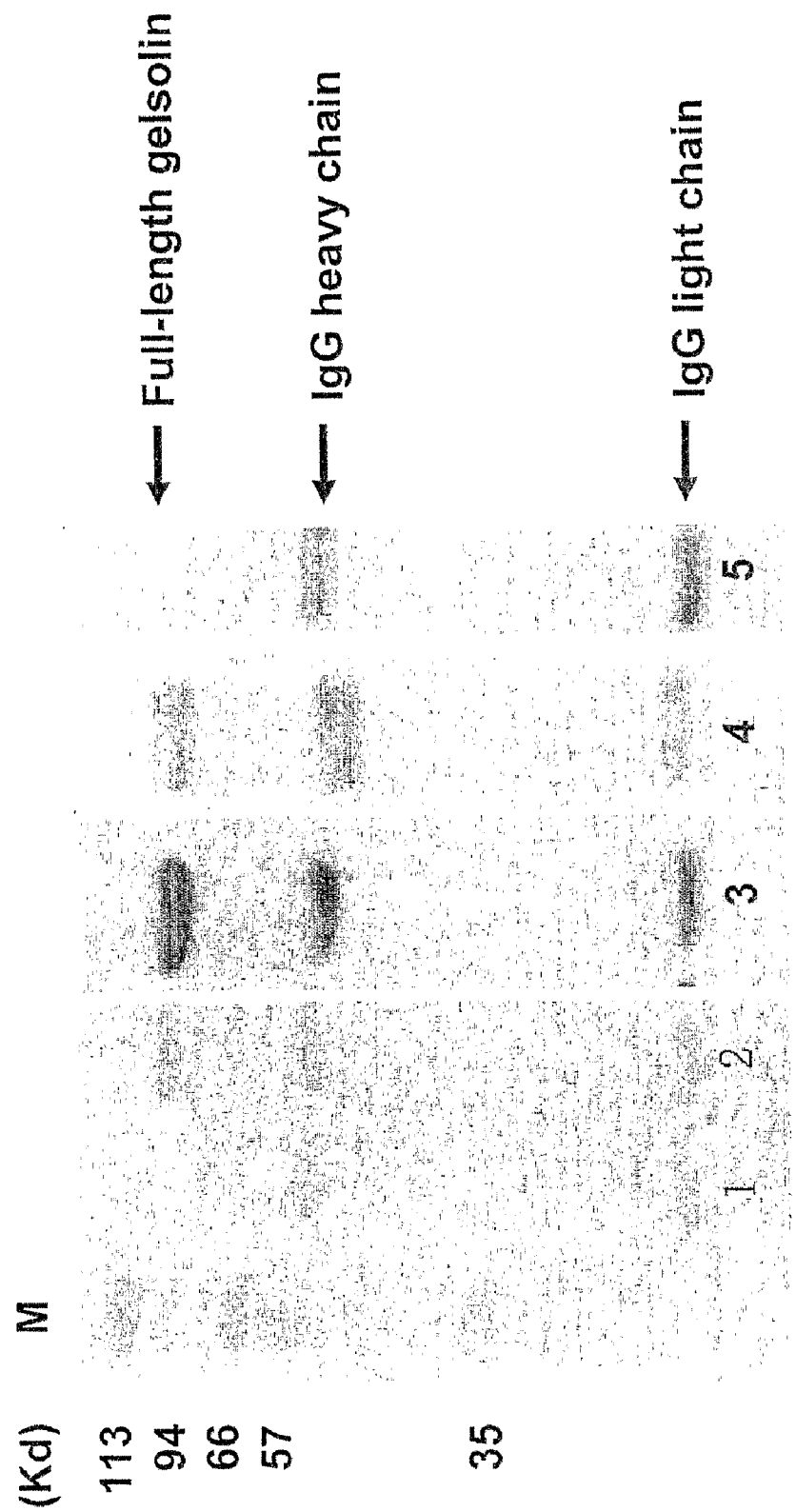

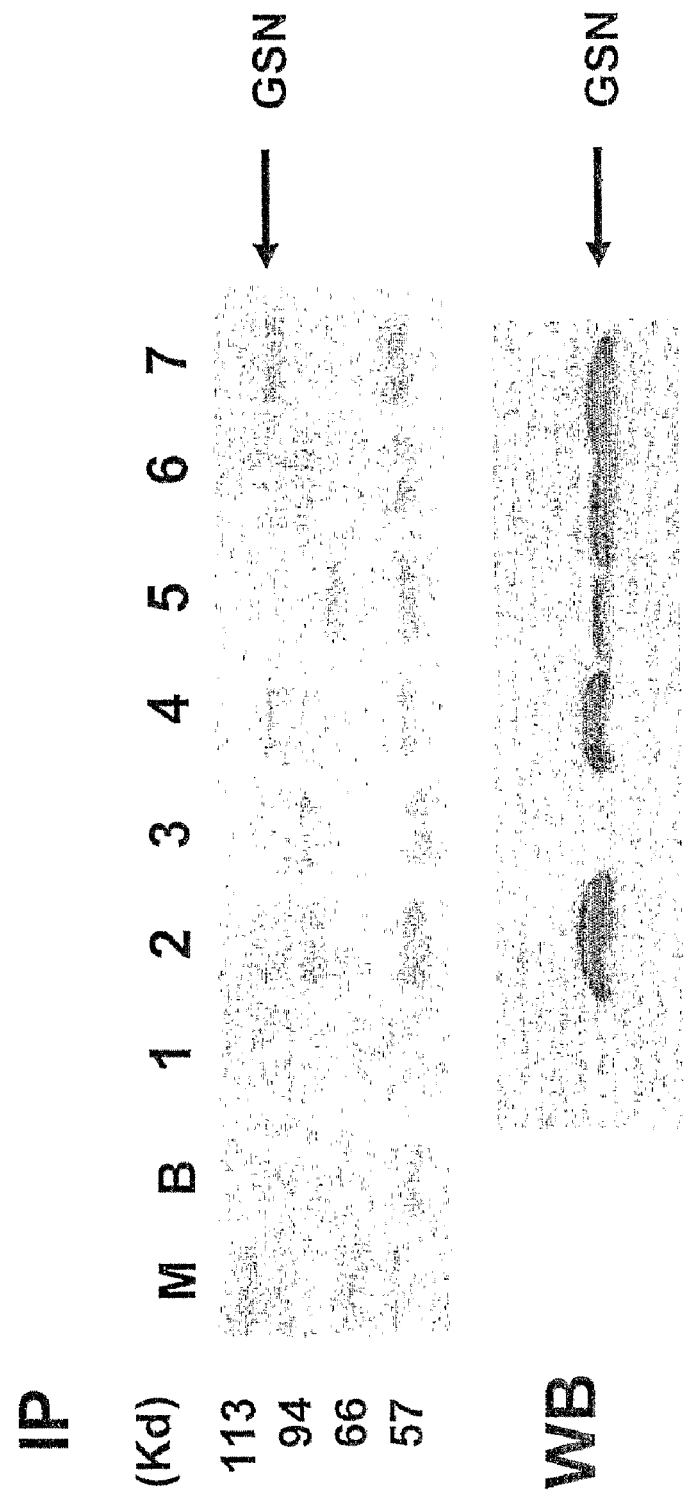

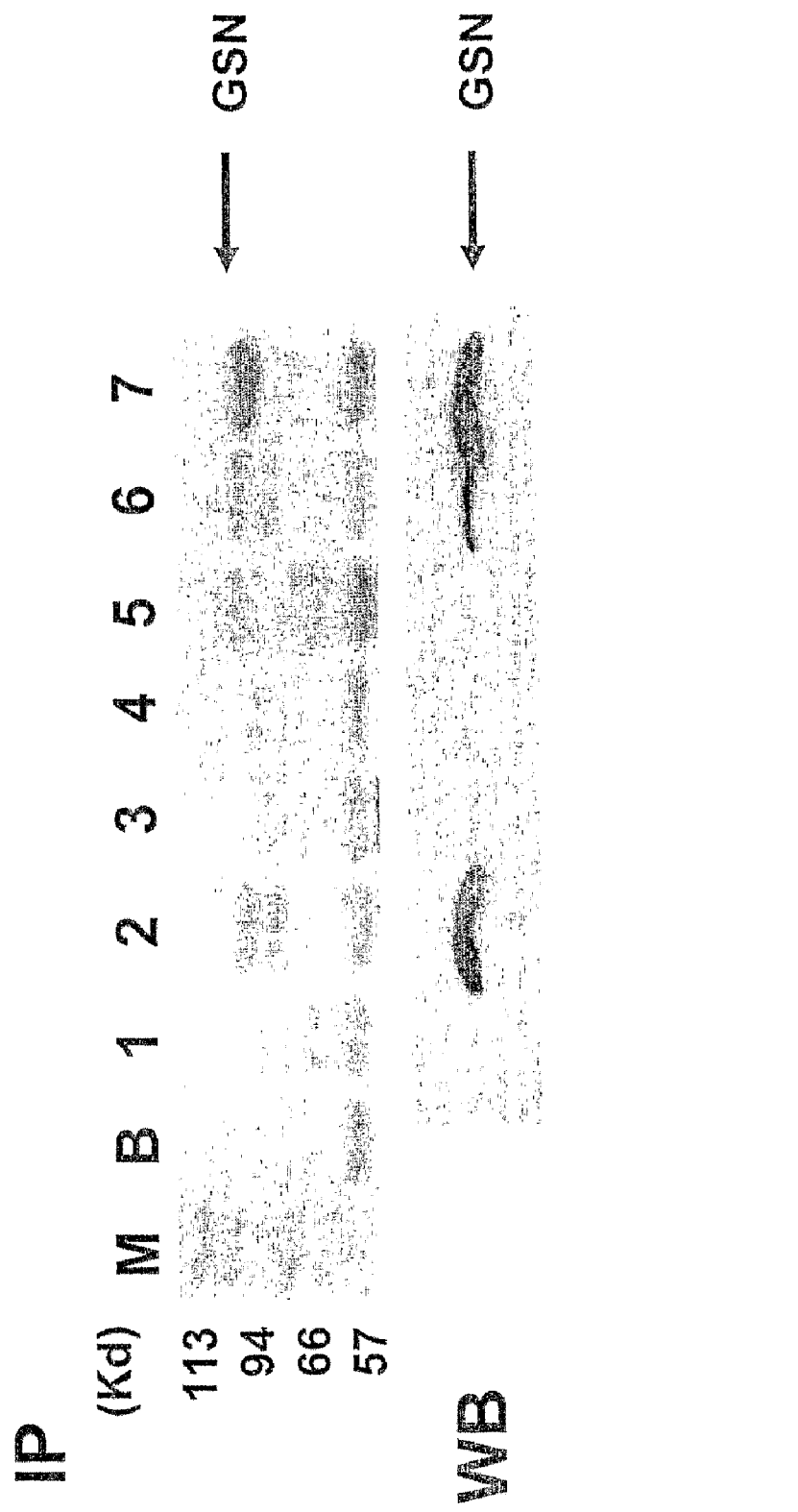

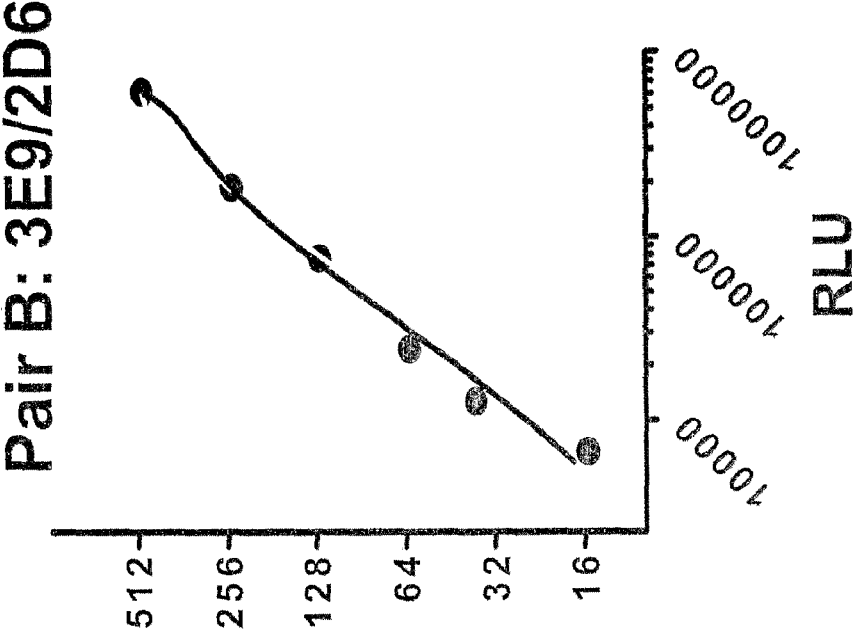
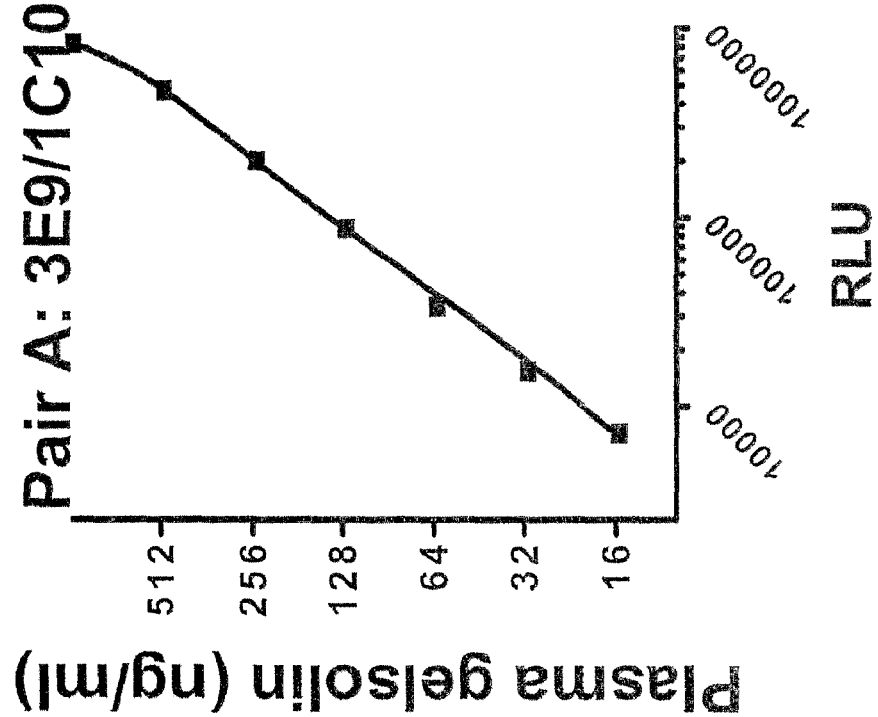

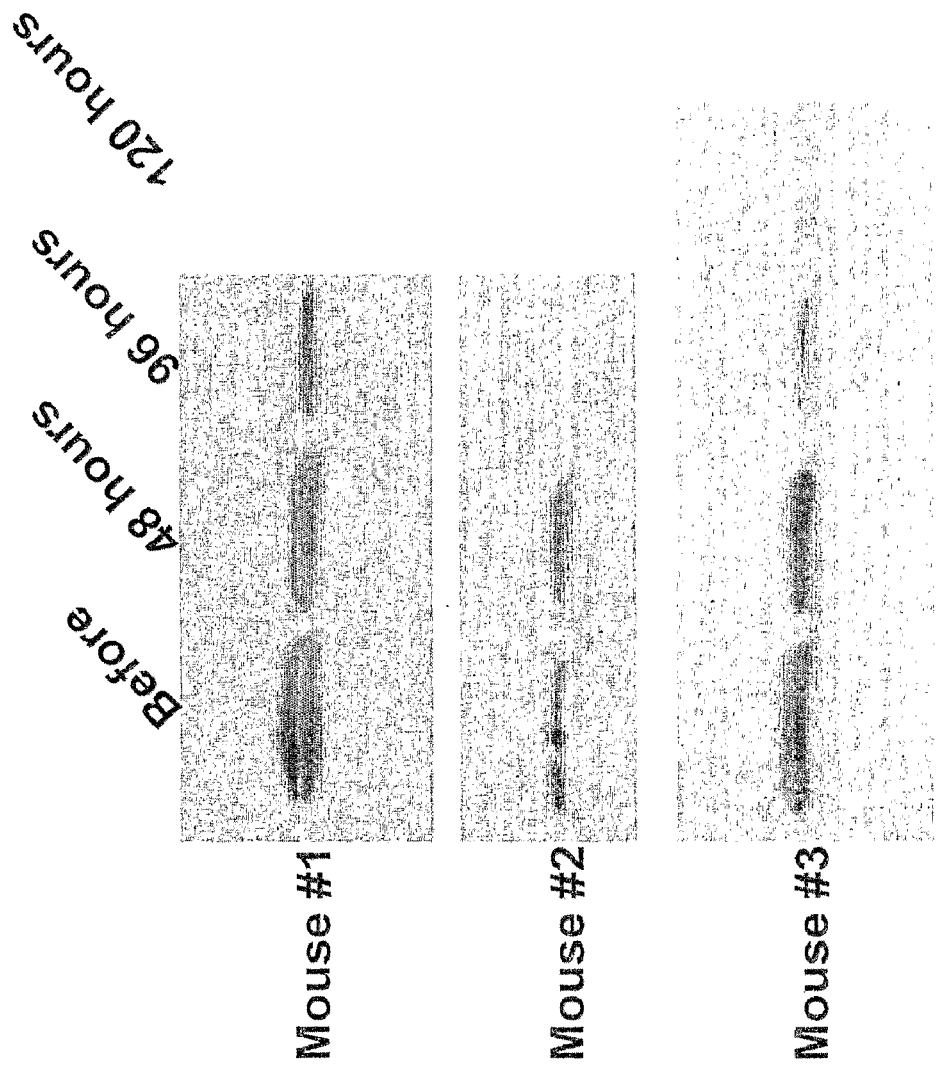

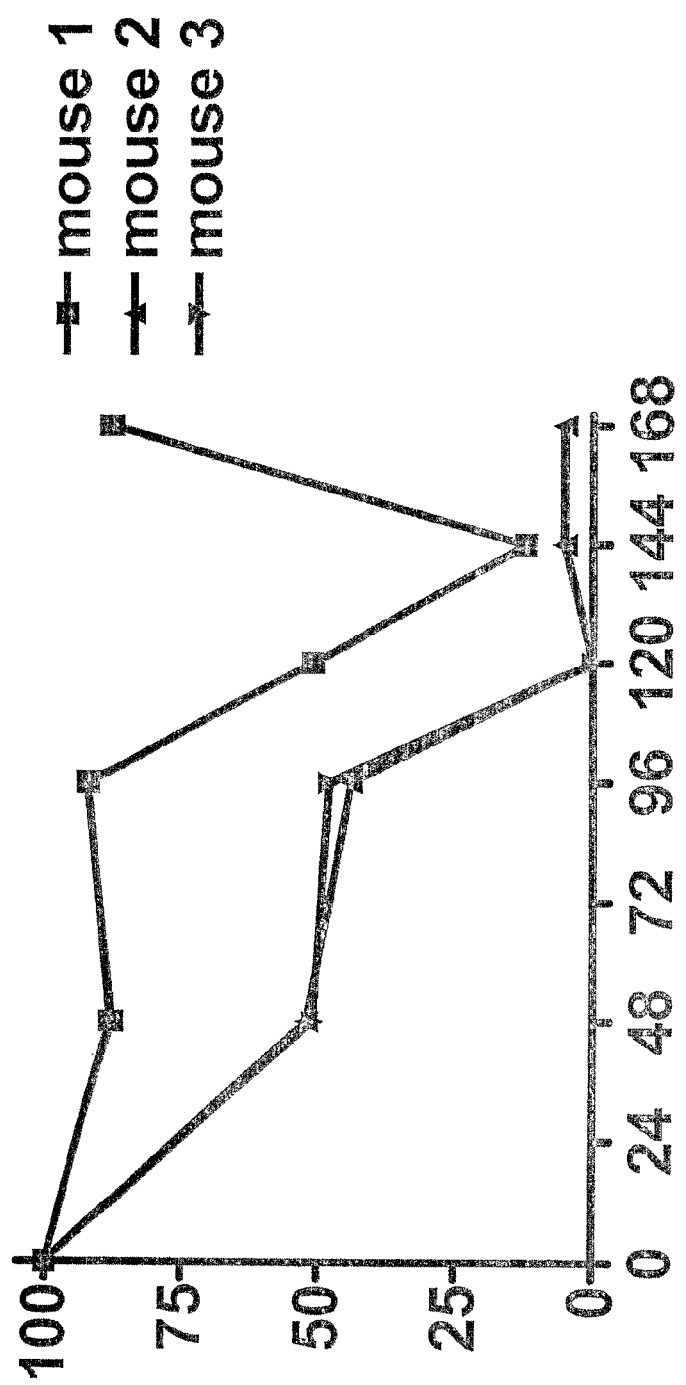

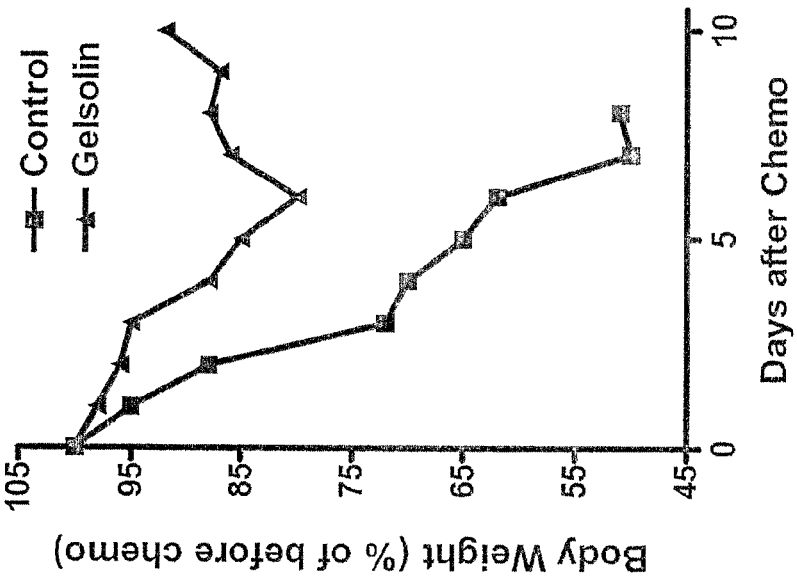
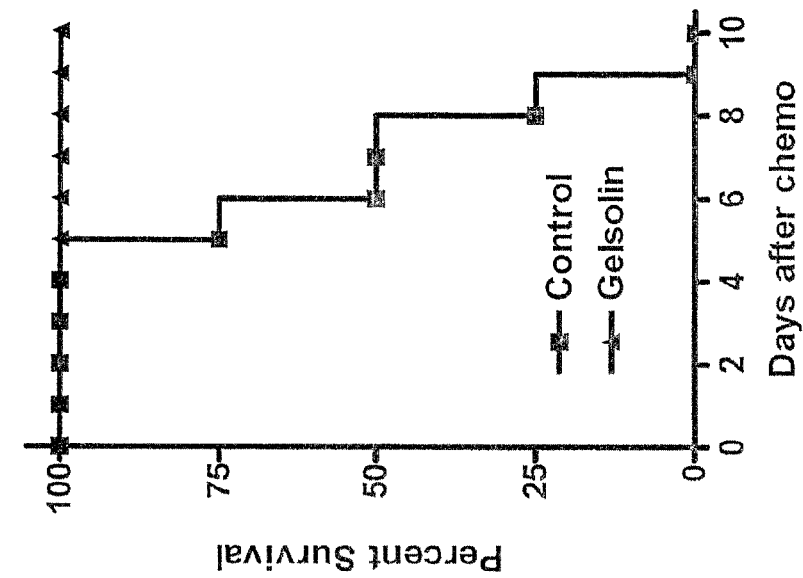
FIG. 18A
FIG. 18B

FIG. 19

SEQUENCE LISTING

```
<160> NUMBER OF SEQ ID NOS: 47

<210> SEQ ID NO 1
<211> LENGTH: 782
<212> TYPE: PRT
<213> ORGANISM: Homo sapiens

<400> SEQUENCE: 1

Met Ala Pro His Arg Pro Ala Pro Ala Leu Leu Cys Ala Leu Ser Leu
1               5                   10                  15

Ala Leu Cys Ala Leu Ser Leu Pro Val Arg Ala Ala Thr Ala Ser Arg
                20                  25                  30

Gly Ala Ser Gln Ala Gly Ala Pro Gln Gly Arg Val Pro Glu Ala Arg
                35                  40                  45

Pro Asn Ser Met Val Val Glu His Pro Glu Phe Leu Lys Ala Gly Lys
        50                  55                  60

Glu Pro Gly Leu Gln Ile Trp Arg Val Glu Lys Phe Asp Leu Val Pro
65                  70                  75                  80

Val Pro Thr Asn Leu Tyr Gly Asp Phe Phe Thr Gly Asp Ala Tyr Val
                85                  90                  95

Ile Leu Lys Thr Val Gln Leu Arg Asn Gly Asn Leu Gln Tyr Asp Leu
                100                 105                 110
```

-continued

```
His Tyr Trp Leu Gly Asn Glu Cys Ser Gln Asp Glu Ser Gly Ala Ala
            115                 120                 125

Ala Ile Phe Thr Val Gln Leu Asp Asp Tyr Leu Asn Gly Arg Ala Val
        130                 135                 140

Gln His Arg Glu Val Gln Gly Phe Glu Ser Ala Thr Phe Leu Gly Tyr
145                 150                 155                 160

Phe Lys Ser Gly Leu Lys Tyr Lys Lys Gly Val Ala Ser Gly Phe
                165                 170                 175

Lys His Val Val Pro Asn Glu Val Val Gln Arg Leu Phe Gln Val
                180                 185                 190

Lys Gly Arg Arg Val Val Arg Ala Thr Glu Val Pro Val Ser Trp Glu
                195                 200                 205

Ser Phe Asn Asn Gly Asp Cys Phe Ile Leu Asp Leu Gly Asn Asn Ile
210                 215                 220

His Gln Trp Cys Gly Ser Asn Ser Asn Arg Tyr Glu Arg Leu Lys Ala
225                 230                 235                 240

Thr Gln Val Ser Lys Gly Ile Arg Asp Asn Glu Arg Ser Gly Arg Ala
                245                 250                 255

Arg Val His Val Ser Glu Glu Gly Thr Glu Pro Glu Ala Met Leu Gln
                260                 265                 270

Val Leu Gly Pro Lys Pro Ala Leu Pro Ala Gly Thr Glu Asp Thr Ala
                275                 280                 285

Lys Glu Asp Ala Ala Asn Arg Lys Leu Ala Lys Leu Tyr Lys Val Ser
290                 295                 300

Asn Gly Ala Gly Thr Met Ser Val Ser Leu Val Ala Asp Glu Asn Pro
305                 310                 315                 320

Phe Ala Gln Gly Ala Leu Lys Ser Glu Asp Cys Phe Ile Leu Asp His
                325                 330                 335

Gly Lys Asp Gly Lys Ile Phe Val Trp Lys Gly Lys Gln Ala Asn Thr
                340                 345                 350

Glu Glu Arg Lys Ala Ala Leu Lys Thr Ala Ser Asp Phe Ile Thr Lys
            355                 360                 365

Met Asp Tyr Pro Lys Gln Thr Gln Val Ser Val Leu Pro Glu Gly Gly
        370                 375                 380

Glu Thr Pro Leu Phe Lys Gln Phe Phe Lys Asn Trp Arg Asp Pro Asp
385                 390                 395                 400

Gln Thr Asp Gly Leu Gly Leu Ser Tyr Leu Ser Ser His Ile Ala Asn
                405                 410                 415

Val Glu Arg Val Pro Phe Asp Ala Ala Thr Leu His Thr Ser Thr Ala
                420                 425                 430

Met Ala Ala Gln His Gly Met Asp Asp Asp Gly Thr Gly Gln Lys Gln
            435                 440                 445

Ile Trp Arg Ile Glu Gly Ser Asn Lys Val Pro Val Asp Pro Ala Thr
    450                 455                 460

Tyr Gly Gln Phe Tyr Gly Gly Asp Ser Tyr Ile Ile Leu Tyr Asn Tyr
465                 470                 475                 480

Arg His Gly Gly Arg Gln Gly Gln Ile Ile Tyr Asn Trp Gln Gly Ala
                485                 490                 495

Gln Ser Thr Gln Asp Glu Val Ala Ala Ser Ala Ile Leu Thr Ala Gln
            500                 505                 510

Leu Asp Glu Glu Leu Gly Gly Thr Pro Val Gln Ser Arg Val Val Gln
        515                 520                 525

Gly Lys Glu Pro Ala His Leu Met Ser Leu Phe Gly Gly Lys Pro Met
530                 535                 540
```

```
Ile Ile Tyr Lys Gly Gly Thr Ser Arg Glu Gly Gly Gln Thr Ala Pro
545                 550                 555                 560

Ala Ser Thr Arg Leu Phe Gln Val Arg Ala Asn Ser Ala Gly Ala Thr
            565                 570                 575

Arg Ala Val Glu Val Leu Pro Lys Ala Gly Ala Leu Asn Ser Asn Asp
        580                 585                 590

Ala Phe Val Leu Lys Thr Pro Ser Ala Ala Tyr Leu Trp Val Gly Thr
    595                 600                 605

Gly Ala Ser Glu Ala Glu Lys Thr Gly Ala Gln Glu Leu Leu Arg Val
610                 615                 620

Leu Arg Ala Gln Pro Val Gln Val Ala Glu Gly Ser Glu Pro Asp Gly
625                 630                 635                 640

Phe Trp Glu Ala Leu Gly Gly Lys Ala Ala Tyr Arg Thr Ser Pro Arg
            645                 650                 655

Leu Lys Asp Lys Lys Met Asp Ala His Pro Pro Arg Leu Phe Ala Cys
        660                 665                 670

Ser Asn Lys Ile Gly Arg Phe Val Ile Glu Glu Val Pro Gly Glu Leu
    675                 680                 685

Met Gln Glu Asp Leu Ala Thr Asp Val Met Leu Leu Asp Thr Trp
690                 695                 700

Asp Gln Val Phe Val Trp Val Gly Lys Asp Ser Gln Glu Glu Glu Lys
705                 710                 715                 720

Thr Glu Ala Leu Thr Ser Ala Lys Arg Tyr Ile Glu Thr Asp Pro Ala
            725                 730                 735

Asn Arg Asp Arg Arg Thr Pro Ile Thr Val Val Lys Gln Gly Phe Glu
        740                 745                 750

Pro Pro Ser Phe Val Gly Trp Phe Leu Gly Trp Asp Asp Asp Tyr Trp
    755                 760                 765

Ser Val Asp Pro Leu Asp Arg Ala Met Ala Glu Leu Ala Ala
770                 775                 780

<210> SEQ ID NO 2
<211> LENGTH: 10
<212> TYPE: PRT
<213> ORGANISM: Artificial sequence
<220> FEATURE:
<223> OTHER INFORMATION: Synthetic peptide

<400> SEQUENCE: 2

Phe Ala Gln Gly Ala Leu Lys Ser Glu Asp
1               5                   10

<210> SEQ ID NO 3
<211> LENGTH: 10
<212> TYPE: PRT
<213> ORGANISM: Artificial sequence
<220> FEATURE:
<223> OTHER INFORMATION: Synthetic peptide

<400> SEQUENCE: 3

Ser Glu Pro Asp Gly Phe Trp Glu Ala Leu
1               5                   10

<210> SEQ ID NO 4
<211> LENGTH: 10
<212> TYPE: PRT
<213> ORGANISM: Artificial sequence
<220> FEATURE:
<223> OTHER INFORMATION: Synthetic peptide
```

<400> SEQUENCE: 4

Ala Cys Ser Asn Lys Ile Gly Arg Phe Val
1               5                   10

<210> SEQ ID NO 5
<211> LENGTH: 31
<212> TYPE: DNA
<213> ORGANISM: Artificial sequence
<220> FEATURE:
<223> OTHER INFORMATION: Synthetic primer

<400> SEQUENCE: 5
caccggatcc ctgctttgcg cgctgtccct g                          31

<210> SEQ ID NO 6
<211> LENGTH: 27
<212> TYPE: DNA
<213> ORGANISM: Artificial sequence
<220> FEATURE:
<223> OTHER INFORMATION: Synthetic primer

<400> SEQUENCE: 6
ctcgagtcag gcagccagct cagccat                               27

<210> SEQ ID NO 7
<211> LENGTH: 31
<212> TYPE: DNA
<213> ORGANISM: Artificial sequence
<220> FEATURE:
<223> OTHER INFORMATION: Synthetic primer

<400> SEQUENCE: 7
caccggatcc ctgctttgcg cgctgtccct g                          31

<210> SEQ ID NO 8
<211> LENGTH: 30
<212> TYPE: DNA
<213> ORGANISM: Artificial sequence
<220> FEATURE:
<223> OTHER INFORMATION: Synthetic primer

<400> SEQUENCE: 8
ttactcgagt ccatatgtgg cagggtccac                            30

<210> SEQ ID NO 9
<211> LENGTH: 29
<212> TYPE: DNA
<213> ORGANISM: Artificial sequence
<220> FEATURE:
<223> OTHER INFORMATION: Synthetic primer

<400> SEQUENCE: 9
caccggatcc gccacatatg gacagttct                             29

<210> SEQ ID NO 10
<211> LENGTH: 27
<212> TYPE: DNA
<213> ORGANISM: Artificial sequence
<220> FEATURE:
<223> OTHER INFORMATION: Synthetic primer

<400> SEQUENCE: 10
ctcgagtcag gcagccagct cagccat                               27

<210> SEQ ID NO 11
<211> LENGTH: 31

```
<212> TYPE: DNA
<213> ORGANISM: Artificial sequence
<220> FEATURE:
<223> OTHER INFORMATION: Synthetic primer

<400> SEQUENCE: 11
caccggatcc ctgctttgcg cgctgtccct g                              31

<210> SEQ ID NO 12
<211> LENGTH: 27
<212> TYPE: DNA
<213> ORGANISM: Artificial sequence
<220> FEATURE:
<223> OTHER INFORMATION: Synthetic primer

<400> SEQUENCE: 12
ggatccctat ccatatgtgg cagggtc                                   27

<210> SEQ ID NO 13
<211> LENGTH: 31
<212> TYPE: DNA
<213> ORGANISM: Artificial sequence
<220> FEATURE:
<223> OTHER INFORMATION: Synthetic primer

<400> SEQUENCE: 13
caccggatcc ctgctttgcg cgctgtccct g                              31

<210> SEQ ID NO 14
<211> LENGTH: 27
<212> TYPE: DNA
<213> ORGANISM: Artificial sequence
<220> FEATURE:
<223> OTHER INFORMATION: Synthetic primer

<400> SEQUENCE: 14
ggatccctag ttggcgatat ggctgga                                   27

<210> SEQ ID NO 15
<211> LENGTH: 31
<212> TYPE: DNA
<213> ORGANISM: Artificial sequence
<220> FEATURE:
<223> OTHER INFORMATION: Synthetic primer

<400> SEQUENCE: 15
caccggatcc ctgctttgcg cgctgtccct g                              31

<210> SEQ ID NO 16
<211> LENGTH: 27
<212> TYPE: DNA
<213> ORGANISM: Artificial sequence
<220> FEATURE:
<223> OTHER INFORMATION: Synthetic primer

<400> SEQUENCE: 16
ggatccctag atgaagtcag aggctgt                                   27

<210> SEQ ID NO 17
<211> LENGTH: 31
<212> TYPE: DNA
<213> ORGANISM: Artificial sequence
<220> FEATURE:
<223> OTHER INFORMATION: Synthetic primer

<400> SEQUENCE: 17
caccggatcc ctgctttgcg cgctgtccct g                              31
```

<210> SEQ ID NO 18
<211> LENGTH: 26
<212> TYPE: DNA
<213> ORGANISM: Artificial sequence
<220> FEATURE:
<223> OTHER INFORMATION: Synthetic primer

<400> SEQUENCE: 18
ggatccctaa gccacgaggg agacgg                                          26

<210> SEQ ID NO 19
<211> LENGTH: 31
<212> TYPE: DNA
<213> ORGANISM: Artificial sequence
<220> FEATURE:
<223> OTHER INFORMATION: Synthetic primer

<400> SEQUENCE: 19
caccggatcc ctgctttgcg cgctgtccct g                                    31

<210> SEQ ID NO 20
<211> LENGTH: 27
<212> TYPE: DNA
<213> ORGANISM: Artificial sequence
<220> FEATURE:
<223> OTHER INFORMATION: Synthetic primer

<400> SEQUENCE: 20
ggatccctac tcagtgccct cctcaga                                         27

<210> SEQ ID NO 21
<211> LENGTH: 31
<212> TYPE: DNA
<213> ORGANISM: Artificial sequence
<220> FEATURE:
<223> OTHER INFORMATION: Synthetic primer

<400> SEQUENCE: 21
caccggatcc ctgctttgcg cgctgtccct g                                    31

<210> SEQ ID NO 22
<211> LENGTH: 27
<212> TYPE: DNA
<213> ORGANISM: Artificial sequence
<220> FEATURE:
<223> OTHER INFORMATION: Synthetic primer

<400> SEQUENCE: 22
ggatccctag aagcagtcgc cattgtt                                         27

<210> SEQ ID NO 23
<211> LENGTH: 31
<212> TYPE: DNA
<213> ORGANISM: Artificial sequence
<220> FEATURE:
<223> OTHER INFORMATION: Synthetic primer

<400> SEQUENCE: 23
caccggatcc ctgctttgcg cgctgtccct g                                    31

<210> SEQ ID NO 24
<211> LENGTH: 27
<212> TYPE: DNA
<213> ORGANISM: Artificial sequence
<220> FEATURE:
<223> OTHER INFORMATION: Synthetic primer

<400> SEQUENCE: 24
ggatccctac ttcaggccag acttgaa                                27

<210> SEQ ID NO 25
<211> LENGTH: 31
<212> TYPE: DNA
<213> ORGANISM: Artificial sequence
<220> FEATURE:
<223> OTHER INFORMATION: Synthetic primer

<400> SEQUENCE: 25
caccggatcc ctgctttgcg cgctgtccct g                           31

<210> SEQ ID NO 26
<211> LENGTH: 27
<212> TYPE: DNA
<213> ORGANISM: Artificial sequence
<220> FEATURE:
<223> OTHER INFORMATION: Synthetic primer

<400> SEQUENCE: 26
ggatccctac agccagtagt ggaggtc                                27

<210> SEQ ID NO 27
<211> LENGTH: 29
<212> TYPE: DNA
<213> ORGANISM: Artificial sequence
<220> FEATURE:
<223> OTHER INFORMATION: Synthetic primer

<400> SEQUENCE: 27
caccggatcc gccacatatg gacagttct                              29

<210> SEQ ID NO 28
<211> LENGTH: 27
<212> TYPE: DNA
<213> ORGANISM: Artificial sequence
<220> FEATURE:
<223> OTHER INFORMATION: Synthetic primer

<400> SEQUENCE: 28
ggatccctat caggcagcca gctcagc                                27

<210> SEQ ID NO 29
<211> LENGTH: 29
<212> TYPE: DNA
<213> ORGANISM: Artificial sequence
<220> FEATURE:
<223> OTHER INFORMATION: Synthetic primer

<400> SEQUENCE: 29
caccggatcc gccacatatg gacagttct                              29

<210> SEQ ID NO 30
<211> LENGTH: 27
<212> TYPE: DNA
<213> ORGANISM: Artificial sequence
<220> FEATURE:
<223> OTHER INFORMATION: Synthetic primer

<400> SEQUENCE: 30
ggatccctac gtctcgatgt accgctt                                27

<210> SEQ ID NO 31
<211> LENGTH: 29

```
<212> TYPE: DNA
<213> ORGANISM: Artificial sequence
<220> FEATURE:
<223> OTHER INFORMATION: Synthetic primer

<400> SEQUENCE: 31
caccggatcc gccacatatg gacagttct                                    29

<210> SEQ ID NO 32
<211> LENGTH: 27
<212> TYPE: DNA
<213> ORGANISM: Artificial sequence
<220> FEATURE:
<223> OTHER INFORMATION: Synthetic primer

<400> SEQUENCE: 32
ggatccctac tcttcgatca caaaacg                                      27

<210> SEQ ID NO 33
<211> LENGTH: 29
<212> TYPE: DNA
<213> ORGANISM: Artificial sequence
<220> FEATURE:
<223> OTHER INFORMATION: Synthetic primer

<400> SEQUENCE: 33
caccggatcc gccacatatg gacagttct                                    29

<210> SEQ ID NO 34
<211> LENGTH: 27
<212> TYPE: DNA
<213> ORGANISM: Artificial sequence
<220> FEATURE:
<223> OTHER INFORMATION: Synthetic primer

<400> SEQUENCE: 34
ggatccctat gccacctgca caggttg                                      27

<210> SEQ ID NO 35
<211> LENGTH: 29
<212> TYPE: DNA
<213> ORGANISM: Artificial sequence
<220> FEATURE:
<223> OTHER INFORMATION: Synthetic primer

<400> SEQUENCE: 35
caccggatcc gccacatatg gacagttct                                    29

<210> SEQ ID NO 36
<211> LENGTH: 27
<212> TYPE: DNA
<213> ORGANISM: Artificial sequence
<220> FEATURE:
<223> OTHER INFORMATION: Synthetic primer

<400> SEQUENCE: 36
ggatccctaa ggcaatacct caacagc                                      27

<210> SEQ ID NO 37
<211> LENGTH: 10
<212> TYPE: PRT
<213> ORGANISM: Artificial sequence
<220> FEATURE:
<223> OTHER INFORMATION: Synthetic peptide

<400> SEQUENCE: 37

Phe Ala Gln Gly Ala Leu Arg Ser Glu Asp
```

<210> SEQ ID NO 38
<211> LENGTH: 10
<212> TYPE: PRT
<213> ORGANISM: Artificial sequence
<220> FEATURE:
<223> OTHER INFORMATION: Synthetic peptide

<400> SEQUENCE: 38

Ala Cys Ser Asn Arg Ile Gly Arg Phe Val
1               5                   10

<210> SEQ ID NO 39
<211> LENGTH: 10
<212> TYPE: PRT
<213> ORGANISM: Artificial sequence
<220> FEATURE:
<223> OTHER INFORMATION: Synthetic peptide

<400> SEQUENCE: 39

Ser Glu Pro Asp Ser Phe Trp Glu Ala Leu
1               5                   10

<210> SEQ ID NO 40
<211> LENGTH: 10
<212> TYPE: PRT
<213> ORGANISM: Artificial sequence
<220> FEATURE:
<223> OTHER INFORMATION: Synthetic peptide

<400> SEQUENCE: 40

Ser Glu Pro Asp Ala Phe Trp Glu Ala Leu
1               5                   10

<210> SEQ ID NO 41
<211> LENGTH: 10
<212> TYPE: PRT
<213> ORGANISM: Artificial sequence
<220> FEATURE:
<223> OTHER INFORMATION: Synthetic peptide

<400> SEQUENCE: 41

Gly Gly Lys Ala Ala Tyr Arg Thr Ser Pro
1               5                   10

<210> SEQ ID NO 42
<211> LENGTH: 10
<212> TYPE: PRT
<213> ORGANISM: Artificial sequence
<220> FEATURE:
<223> OTHER INFORMATION: Synthetic peptide

<400> SEQUENCE: 42

Gly Gly Lys Ala Thr Tyr Arg Thr Ser Pro
1               5                   10

<210> SEQ ID NO 43
<211> LENGTH: 10
<212> TYPE: PRT
<213> ORGANISM: Artificial sequence
<220> FEATURE:
<223> OTHER INFORMATION: Synthetic peptide

<400> SEQUENCE: 43

Gly Gly Lys Thr Ala Tyr Arg Thr Ser Pro
1               5                   10

```
<210> SEQ ID NO 44
<211> LENGTH: 18
<212> TYPE: PRT
<213> ORGANISM: Artificial sequence
<220> FEATURE:
<223> OTHER INFORMATION: Synthetic peptide

<400> SEQUENCE: 44

Asp Ile Val Met Thr Gln Ser Pro Ala Thr Leu Ser Val Thr Pro Gly
1               5                   10                  15

Asp Arg

<210> SEQ ID NO 45
<211> LENGTH: 15
<212> TYPE: PRT
<213> ORGANISM: Artificial sequence
<220> FEATURE:
<223> OTHER INFORMATION: Synthetic peptide

<400> SEQUENCE: 45

Glu Val Gln Leu Val Glu Ser Gly Gly Gly Leu Val Lys Pro Gly
1               5                   10                  15

<210> SEQ ID NO 46
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 46

Asp Val Gln Met Thr Ser Pro Ser Xaa Leu Thr
1               5                   10

<210> SEQ ID NO 47
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X is G or S

<400> SEQUENCE: 47

Ser Glu Pro Asp Xaa Phe Trp Glu Ala Leu
1               5                   10
```

GELSOLIN BINDING AGENT COMPOSITIONS AND USES OF SAME

CROSS-REFERENCE TO RELATED APPLICATIONS

The present application claims priority as a national stage application of International Application No. PCT/CN2007/002467 filed on Aug. 15, 2007, the entire contents of which are incorporated herein by reference in its entirety.

FIELD OF THE INVENTION

This invention relates generally to the preparation of gelsolin binding agents and uses of the same. In particular, the present invention relates to the preparation of anti-gelsolin antibodies that recognize an antigen determinant (i.e., epitope) of human plasma gelsolin and their use for gelsolin detection.

BACKGROUND OF THE INVENTION

The following description is provided to assist the understanding of the reader. None of the information provided or references cited is admitted to be prior art to the present invention.

Actin is the most abundant protein in animal cells and constitutes 10-20% of the protein of many nucleated cells and 30% of the protein of muscle cells. Actin molecules each bind an ATP molecule and self-assemble into long filaments during which the ATP is hydrolyzed into ADP.

Injury to animal tissues results in the release of actin into the extracellular space, including the bloodstream. Although approximately half of nonmuscle cell actin is F-actin, (the double-helical, rodlike, filament form of actin which is assembled from G-actin monomers), the ionic conditions of extracellular fluids favor actin polymerization, so that virtually all the actin released into the blood from dying cells would be expected to polymerize into filaments (Lind, S. E. et al., *Am. Rev. Respir. Dis.* 138:429-434 (1988)). In purified solutions, in the absence of filament-shortening proteins, actin filaments can easily attain lengths of several microns. Were some fraction of actin released from injured cells to be irreversibly denatured, however, or else bound to one of the intracellular actin-binding proteins discussed below, this actin would remain monomeric.

There are many proteins which naturally associate with actin (for a review of actin-binding proteins, see Stossel et al., *Ann. Rev. Cell Biol.* 1: 353-402 (1985); Pollard et al., *Ann. Rev. Biochem.* 55:987-1035 (1986)). However, two proteins, gelsolin and DBP (vitamin D binding protein) are thought to be primarily responsible for binding extracellular actin. (Janmey et al., *Blood* 70:529-530 (1987)). Gelsolin is an actin-binding protein that is a key regulator of actin filament assembly and disassembly. Gelsolin is an 82-kDa protein with six homologous subdomains, referred to as S1-S6. Each subdomain is composed of a five-stranded β-sheet, flanked by two α-helices, one positioned perpendicular with respect to the strands and one positioned parallel. The N-terminal (S1-S3) forms an extended β-sheet, as does the C-terminal (S4-S6) (Kiselar et al. *PNAS* 100: 3942-3947 (2003)). The protein is highly conserved and highly homologous among species. Gelsolin is located intracellularly (in cytosol and mitochondria) and extracellularly (in blood plasma). Koya et al., *J Biol Chem* 275 (20): 15343-15349 (2000).

Gelsolin has several functions in regulating actin polymerization. First, gelsolin is involved in monomeric actin binding. In the presence of $Ca^{2+}$, gelsolin binds two actin monomers. Gelsolin can also bind actin filaments by a another actin binding site. Second, gelsolin binds two actin monomers to form a nucleus for actin polymerization and caps the barbed end of actin filaments. Thus, gelsolin is capable of both serving as a nucleus for actin polymerization and capping the ends of the nascent microfilaments. Finally, gelsolin has actin severing activity.

Because of the large amounts of actin in cells, the release of actin from dying cells provides sufficient actin to have a significant affect on the microenvironment, either by increasing the viscosity of extracellular fluids of plasma and/or by entrapping cells or by other, as yet unidentified toxic effects. Infusion of extracellular free actin is toxic to animal tissues, and especially to renal and cardiopulmonary systems (Harper et al., *Clin. Res.* 36:625 A (1988); Haddad et al., *PNAS* 87: 1381-1385 (1990)). Acute renal failure is a complication of muscle injury and actin infusions in rats causes transient elevations of the blood urea nitrogen (BUN) and creatinine levels, consistent with renal failure. Free actin in the plasma may form filaments which may lead to multiple organ dysfunction syndrome (Dahl et al., *Shock* 12(2): 102-4 (1999)). Moreover, since each extracellular actin molecule in a filament has an ADP molecule associated with it, the presence of extracellular actin in the blood may tend to induce or augment platelet aggregation in a manner which may not be advantageous to the host (Lind et al., *Am. Rev. Respir. Dis.* 138:429-434 (1988); Scarborough et al., *Biochem. Biophy. Res. Commun.* 100:1314-1319 (1981)). Consequently, plasma gelsolin has a vital function of scavenging actin released from dead and dying cells and plasma gelsolin levels appear to be an early prognostic marker in patients experiencing trauma (Mounzer et al., *Am. J. Respir. Crit. Care Med.* 160: 1673-81 (1999)).

SUMMARY OF THE INVENTION

This invention relates generally to the preparation of gelsolin binding agents and uses of the same. In particular, the present invention relates to the preparation of anti-gelsolin antibodies that recognize an antigen determinant (i.e., epitope) of human plasma gelsolin and their use for gelsolin detection. In one aspect, the invention provides an antibody or antigen-binding fragment thereof having the same antigen-binding specificity of antibodies produced by a deposited cell line selected from the group consisting of CGMCC Accession Nos: 2114, 2115, and 2116. In one embodiment, the invention provides, an antibody or an antigen-binding fragment thereof, comprising at least heavy chain CDR3 amino acid sequence selected from the group consisting of: FAQGALKSED (SEQ ID NO.: 2), SEPDGFWEAL (SEQ ID NO.: 3), and ACSNKI-GRFV (SEQ ID NO.: 4) or a variant thereof having one or more conservative amino acid substitutions, wherein the antibody or the fragment thereof specifically binds gelsolin. In one embodiment, the invention provides nucleic acids compositions encoding an antibody or an antigen-binding fragments of the invention. In one embodiment, the invention provides a vector comprising nucleic acids composition encoding an antibody or an antigen-binding fragment of the invention. The vector may further comprise a promoter operably-linked to the nucleic acid molecule. In one embodiment, the invention provides a host cell that comprises a vector comprising nucleic acids composition encoding an antibody or an antigen-binding fragment of the invention. In one embodiment, the invention provides a continuous cell line which produces a monoclonal antibody, wherein the monoclonal antibody binds to the same antigenic determinant as an antibody produced by a hybridoma cell line selected from the group consisting of: CGMCC Accession Nos: 2114, 2115, and 2116, wherein the cell line is produced by the process of fusing a lymphocyte derived from a mouse immunized with carcinoma cells or an immunogenic determinant thereof and a mouse myeloma cell.

In another aspect, the invention provides a method for preparing an antibody or fragment thereof that binds immuno specifically to a polypeptide of SEQ ID NO.:1, the method comprising the steps of: (a) culturing a cell containing a nucleic acid according to claim 4 under conditions that provide for expression of the antibody or fragment thereof; and (b) recovering the expressed antibody or fragment thereof.

In another aspect, the invention provides an isolated epitope of gelsolin comprising an amino acid sequence selected from the group consisting of: FAQGALKSED (SEQ ID NO.: 2), SEPDGFWEAL (SEQ ID NO.: 3), and ACSNKI-GRFV (SEQ ID NO.: 4), wherein the epitope is recognized by an antibody capable of binding full-length human gelsolin. In one embodiment, invention provides an antibody or an antigen-binding fragment thereof generated by preparation of an immunogen containing an epitope of gelsolin comprising an amino acid sequence selected from the group consisting of: FAQGALKSED (SEQ ID NO.: 2), SEPDGFWEAL (SEQ ID NO.: 3), and ACSNKIGRFV (SEQ ID NO.: 4).

In one aspect, the invention provides a method for determining the presence or amount of gelsolin in a biological sample comprising the steps of: (a) contacting a biological sample with one or more of the antibodies or antigen-binding fragments thereof having the same antigen-binding specificity produced by a deposited cell line selected from the group consisting of: CGMCC Accession Nos: 2114, 2115, and 2116 under conditions wherein the antibody or fragment thereof specifically binds to gelsol in; and (b) detecting the presence or amount of antibody or fragment thereof bound to the gelsolin, thereby determining the presence or amount of the gelsolin in the sample. In one embodiment of the method, the sample is contacted with said antibody or an antigen-binding fragment in an ELISA. In one embodiment of the method, the step of contacting comprises binding a first antibody to a substrate and contacting the sample and binding a second antibody to the substrate, wherein the second antibody comprises a detectable label. In one embodiment of the method, the first antibody binds to the same antigenic determinant as an antibody produced by a hybridoma cell line CGMCC Accession No: 2115 and the second antibody binds to the same antigenic determinant as an antibody produced by a hybridoma cell line selected from the group consisting of CGMCC Accession No. 2114 and 2116.

In one aspect, the invention provides a method for monitoring septic shock in a mammalian subject, the method comprising the steps of: (a) measuring the level of gelsolin in a mammalian subject according to a method of the invention for determining the presence or amount of gelsolin in a biological sample; (b) comparing the level of gelsolin in the first subject to a reference standard, wherein the reference standard comprises a control subject not having septic shock, and wherein a decrease in the level of gelsolin of the first subject compared to the reference standard indicates that the mammalian subject has septic shock.

In another aspect, the invention provides a method of selecting a mammalian subject for inclusion in a clinical trial for determining the efficacy of a compound to prevent or treat a medical condition, comprising the steps of: (a) measuring the level of gelsolin in the mammalian subject according to a method of the invention for determining the presence or amount of gelsolin in a biological sample; (b) comparing the level of gelsolin in the first subject to a reference standard, wherein the reference standard comprises a control mammalian subject not having a disease or condition affecting gelsolin levels, and (c) selecting to include the mammalian subject in the clinical trial, wherein a similarity in the gelsolin level of the mammalian subject is similar to the gelsolin level of the reference standard.

In another aspect, the invention provides a method for determining the presence of, or predisposition to, a disease or condition associated with altered levels of a gelsolin polypeptide in a first mammalian subject, the method comprising the steps of: (a) providing a test sample from the first mammalian subject; (b) contacting the test sample from the first mammalian subject with one or more compounds that bind the gelsolin polypeptide to form a compound/gelsolin polypeptide complex, wherein the compound is an antibody or antigen-binding fragment thereof having the same antigen-binding specificity produced by a hybridoma cell line selected from the group consisting of CGMCC Accession No. 2114, 2115, and 2116; (c) detecting the level of compound/gelsolin polypeptide complex; (d) quantifying the level of expression of the gelsolin polypeptide in the sample from the first mammalian subject; and (e) comparing the amount of the gelsolin polypeptide in the sample of step (a) to the amount of polypeptide present in a control sample from a second mammalian subject known not to have, or not to be predisposed to, the disease or condition, wherein an alteration in the expression level of the gelsolin polypeptide in the first subject as compared to the control sample indicates the presence of, or predisposition to, the disease or condition. In one embodiment of the method, sample is contacted with the compound in an ELISA. In one embodiment of the method, the step of contacting comprises binding a first antibody to a substrate and contacting the sample and a second antibody to the substrate, wherein the second antibody comprises a detectable label. In one embodiment of the method, the first antibody binds to the same antigenic determinant as an antibody produced by a hybridoma cell line CGMCC Accession No: 2115 and the second antibody binds to the same antigenic determinant as an antibody produced by a hybridoma cell line selected from the group consisting of CGMCC Accession No. 2114 and 2116. In one embodiment of the method, the disease or condition associated with altered levels of gelsolin is selected from the group consisting of: septic shock, multiple organ dysfunction syndrome rheumatoid arthritis, stroke, heart infarction, cancer, systemic autoimmune disease, chronic hepatitis, side-effects of chemotherapy, and side-effects of radiation therapy.

In one aspect, the invention provides a method for selecting a prophylactic or therapeutic treatment for a subject, comprising the steps of: (a) measuring the level of gelsolin in the mammalian subject according to a method of the invention for determining the presence or amount of gelsolin in a biological sample; (b) assigning the subject to a subject class based on the level of gelsolin of the subject; and (c) selecting a prophylactic or therapeutic treatment based on the subject class.

In one aspect, the invention provides a method of purifying gelsolin, the method comprising the steps of (a) contacting a biological sample comprising gelsolin with at least one immobilized antibody or antigen-binding fragment thereof to form an immobilized gelsolin antibody complex under conditions wherein the antibody or fragment thereof specifically binds to gelsolin, wherein the antibodies or antigen-binding fragments thereof have the same antigen-binding specificity produced by a deposited cell line selected from the group consisting of: CGMCC Accession Nos: 2114, 2115, and 2116; and (b) recovering the gelsolin from the immobilized gelsolin antibody complex. In one embodiment of the method, the biological sample comprises human serum.

In one aspect, the invention provides a kit comprising one or more containers, one or more antibodies, or antigen-binding fragments thereof, having the same antigen-binding specificity produced by a deposited cell line selected from the group consisting of: CGMCC Accession Nos: 2114, 2115, and 2116 and instructions for using the contents therein.

In one aspect, the invention provides a kit comprising: (a) an ELISA plate coated with a first antibody; and (b) a second antibody in a container, wherein the first and second antibodies are antibodies produced by a deposited cell line selected from the group consisting of: CGMCC Accession Nos: 2114, 2115, and 2116. In one embodiment, the kit further comprising one or more of the following components: a human plasma gelsolin standard, human plasma dilution buffer, washing buffer, and substrate buffer.

BRIEF DESCRIPTION OF THE DRAWINGS

FIG. 3 is a western blot analysis of SDS-PAGE of two human plasma samples probed with anti-gelsolin monoclonal antibodies.

FIG. 4 is a SDS-PAGE analysis of human plasma gelsolin immunoprecipitated with anti-gelsolin antibodies. The samples in each lane were as follows: lane 1: blank control (no plasma); lane 2: GC1C10; lane 3: GF2D6; lane 4 GN3E9; and lane 5: GS2C4.

FIG. 8 is a standard curve of human plasma gelsolin generated by a chemiluminescence ELISA using a pair of antibodies, GN3E9/GC1C10 (FIG. 8A) or GN3E9/GF2D6 (FIG. 8B), showing plasma gelsolin concentration (ng/mL) as a function of detection signal (relative light units, RLU).

FIG. 15 is a western blot analysis of the effect of chemotherapy on plasma gelsolin levels.

FIG. 16 is a western blot analysis of the time-dependent depletion of plasma gelsolin after chemotherapy. FIG. 16A is a photograph of a western blot of serum samples of mice at various time points after receiving adriamycin. FIG. 16D is a quantitative analysis of the western blot in FIG. 16C by densitometry.

FIG. 18 is a graph showing the therapeutic efficacy of full-length recombinant gelsolin in reduction of chemotherapy-induced body weight loss (FIG. 18A) and mortality (FIG. 18B) in an in vivo murine model.

FIG. 19 is a SDS-PAGE of affinity-purified human plasma gelsolin by the GC1C10, GN3E9, and GC2D6 antibodies of the invention.

DETAILED DESCRIPTION

Figure 1:
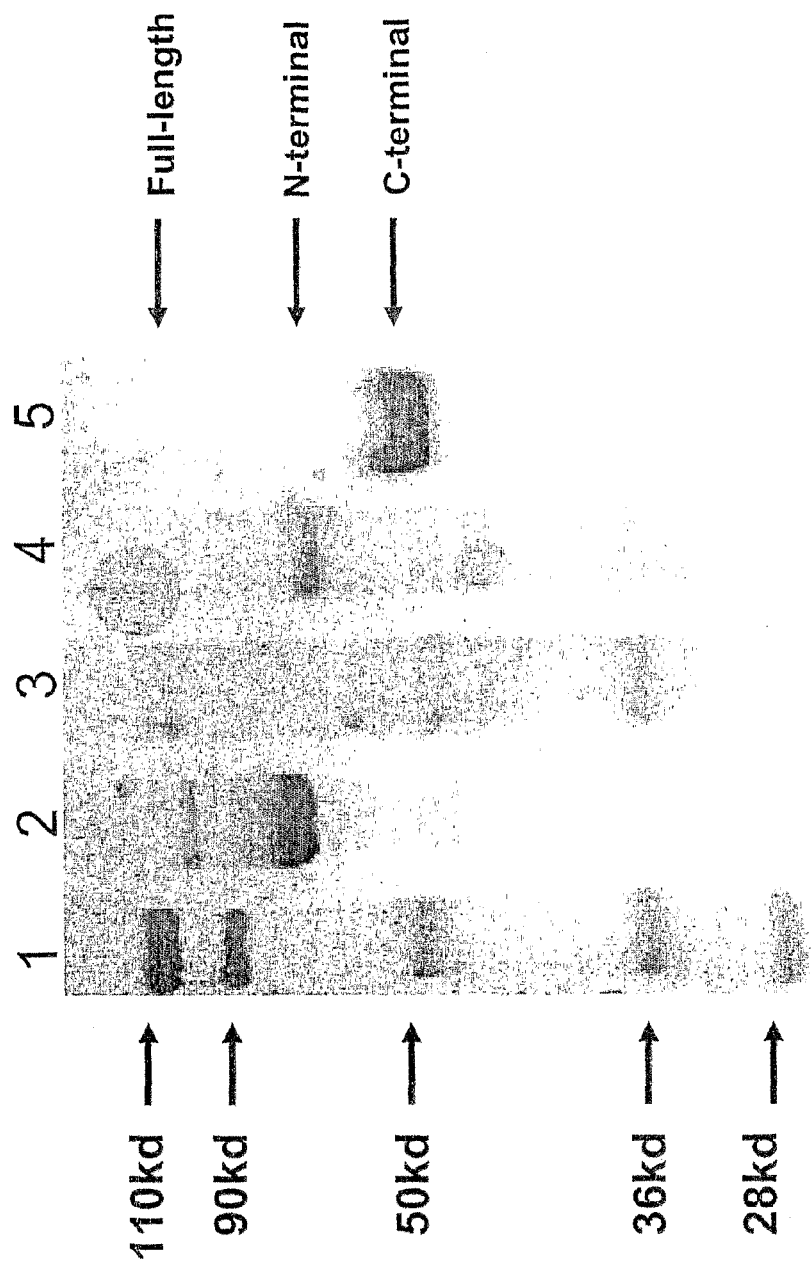
FIG. 1 is a SDS-PAGE analysis of human plasma gelsolin proteins used as immunogens for generation of mouse anti-human gelsolin monoclonal antibodies: native plasma gelsolin (Lane 2), and recombinant full-length gelsolin (Lane 3), a recombinant N-terminal gelsolin fragment (Lane 4), and a recombinant C-terminal gelsolin fragment (Lane 5). A molecular weight marker is shown in Lane 1.

General. It is to be appreciated that certain aspects, modes, embodiments, variations and features of the invention are described below in various levels of detail in order to provide a substantial understanding of the present invention.

The invention generally provides gelsolin binding agents (e.g., antibodies) which can bind to gelsolin polypeptides. Accordingly, the various aspects of the present invention relate to the preparation, expression and characterization of gelsolin binding agents. Gelsolin binding agents of the invention are useful, alone or in combination, to detect a gelsolin polypeptide (a.k.a., the target polypeptide) in a test sample as well as in methods to purify native gelsolin proteins, including native gelsolin polypeptides from a biological sample. Gelsolin binding agents are useful to diagnose a gelsolin-related medical condition in subjects in need thereof. An amino acid sequence of a human gelsolin polypeptide (SEQ ID NO.: 1) is shown in Table 1.

TABLE 1

Human Gelsolin Polypeptide Sequence (SEQ ID NO.: 1)
MAPHRPAPALLCALSLALCALSLPVRAATASRGASQAGAPQGRVPEARPN

SMVVEHPEFLKAGKEPGLQIWRVEKFDLVPVPTNLYGDFFTGDAYVILKT

VQLRNGNLQYDLHYWLGNECSQDESGAAAIFTVQLDDYLNGRAVQHREVQ

GFESATFLGYFKSGLKYKKGGVASGFKHVVPNEVVVQRLFQVKGRRVVRA

TEVPVSWESFNNGDCFILDLGNNIHQWCGSNSNRYERLKATQVSKGIRDN

ERSGRARVHVSEEGTEPEAMLQVLGPKPALPAGTEDTAKEDAANRKLAKL

YKVSNGAGTMSVSLVADENPFAQGALKSEDCFILDHGKDGKIFVWKGKQA

NTEERKAALKTASDFITKMDYPKQTQVSVLPEGGETPLFKQFFKNWRDPD

QTDGLGLSYLSSHIANVERVPFDAATLHTSTAMAAQHGMDDDGTGQKQIW

RIEGSNKVPVDPATYGQFYGGDSYIILYNYRHGGRQGQIIYNWQGAQSTQ

DEVAASAILTAQLDEELGGTPVQSRVVQGKEPAHLMSLFGGKPMIIYKGG

TSREGGQTAPASTRLFQVRANSAGATRAVEVLPKAGALNSNDAFVLKTPS

AAYLWVGTGASEAEKTGAQELLRVLRAQPVQVAEGSEPDGFWEALGGKAA

YRTSPRLKDKKMDAHPPRLFACSNKIGRFVIEEVPGELMQEDLATDDVML

LDTWDQVFVWVGKDSQEEEKTEALTSAKRYIETDPANRDRRTPITVVKQG

FEPPSFVGWFLGWDDDYWSVDPLDRAMAELAA

In some embodiments, the gelsolin binding agents (e.g. anti-gelsolin or anti-gelsolin like antibodies) of the present invention detect the active, or unbound, form of gelsolin. While not wishing to be limited by theory, free and complexed (to actin) gelsolin molecules differ in their functional properties. Although free gelsolin can sever actin filaments, actin-gelsol in complexes cannot. Gelsolin's severing activity is activated by micromolar $Ca^{2+}$ and has been shown to be inhibited by phosphatidyl inositol bisphosphate ($PIP_2$) and phosphatidyl inositol monophosphate (PIP). Since extracellular $Ca^{2+}$ concentrations are at millimolar levels and extracellular fluids do not normally contain PIP or $PIP_2$ in a form that inhibits gelsolin, plasma gelsolin is constitutively active in extracellular fluids.

The various aspects of the present invention further relate to diagnostic methods and kits that use the gelsolin binding agents of the invention to identify individuals predisposed to a medical condition or to classify individuals with regard to drug responsiveness, side effects, or optimal drug dose. In other aspects, the invention provides methods for purifying gelsolin or gelsolin-like polypeptides from a biological sample, including, for example, native human gelsolin from plasma. Accordingly, various particular embodiments that illustrate these aspects follow.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and the claims. Generally, enzymatic reactions and purification steps are performed according to the manufacturer's specifications.

In practicing the present invention, many conventional techniques in molecular biology, protein biochemistry, cell biology, immunology, microbiology and recombinant DNA are used.

These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonuchotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzymol.*, Vols. 154 and 155, Wu & Grossman, and Wu, Eds., respectively. Methods to detect and measure levels of polypeptide gene expression products (i.e., gene translation level) are well-known in the art and include the use polypeptide detection methods such as antibody detection and quantification techniques. (See also, Strachan & Read, *Human Molecular Genetics*, Second Edition. (John Wiley and Sons, Inc., NY, 1999)).

Unless defined otherwise, all technical and scientific terms used herein generally have the same meaning as commonly understood by one of ordinary skill in the art to which this invention belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well known and commonly employed in the art. All references cited herein are incorporated herein by reference in their entireties and for all purposes to the same extent as if each individual publication, patent, or patent application was specifically and individually incorporated by reference in its entirety for all purposes.

Definitions. The definitions of certain terms as used in this specification are provided below. Definitions of other terms may be found in the *Illustrated Dictionary of Immunology*, 2nd Edition (Cruse, J. M. and Lewis, R. E., Eds., Boca Raton, Fla.: CRC Press, 1995). Unless indicated otherwise, the term "gelsolin" when used herein refer to human protein and gene.

As used herein, the "administration" of an agent or drug to a subject or subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

As used herein, the term "antibody" means a polypeptide comprising a framework region from an immunoglobulin gene or fragments thereof that specifically binds and recognizes an antigen, e.g., a gelsolin polypeptide. Use of the term antibody is meant to include whole antibodies, including single-chain whole antibodies, and antigen-binding fragments thereof. The term "antibody" includes bispecific antibodies and multispecific antibodies so long as they exhibit the desired biological activity or function.

As used herein, the term "antibody-related polypeptide" means antigen-binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included in the invention are any combinations of variable region(s) and hinge region, $CH_1$, $CH_2$, and $CH_3$ domains. Antibody-related molecules useful as binding agents of the invention include, e.g., but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Examples include: (i) a Fab fragment, a monovalent fragment consisting of the $V_L$, $V_H$, $C_L$ and $CH_1$ domains; (ii) a F(ab')$_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., *Nature* 341: 544-546, 1989), which consists of a $V_H$ domain; and (vi) an isolated complementarity determining region (CDR). As such "antibody fragments" can comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments. Single-chain antibody molecules may comprise a polymer with a number of individual molecules, for example, dimmer, trimer or other polymers.

As used herein, the term "biological sample" means sample material derived from or contacted by living cells. The term "biological sample" is intended to include tissues, cells and biological fluids isolated from a subject, as well as tissues, cells and fluids present within a subject. Biological samples of the invention include, e.g., but are not limited to, whole blood, plasma, semen, saliva, tears, urine, fecal material, sweat, buccal, skin, cerebrospinal fluid, and hair. Biological samples can also be obtained from biopsies of internal organs or from cancers. Biological samples can be obtained from subjects for diagnosis or research or can be obtained from undiseased individuals, as controls or for basic research.

As used herein, the term "CDR-grafted antibody" means an antibody in which at least one CDR of an "acceptor" antibody is replaced by a CDR "graft" from a "donor" antibody possessing a desirable antigen specificity.

As used herein, the term "chimeric antibody" means an antibody in which the Fc constant region of a monoclonal antibody from one species (e.g., a mouse Fc constant region) is replaced, using recombinant DNA techniques, with an Fc constant region from an antibody of another species (e.g., a human Fc constant region). See generally, Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 125, 023; Better et al., *Science* 240: 1041-1043, 1988; Liu et al., *Proc. Natl. Acad. Sci. USA* 84: 3439-3443, 1987; Liu et al., *J. Immunol.* 139: 3521-3526, 1987; Sun et al., *Proc. Natl. Acad. Sci. USA* 84: 214-218, 1987; Nishimura et al., *Cancer Res* 47: 999-1005, 1987; Wood et al., *Nature* 314: 446-449, 1885; and Shaw et al., *J. Natl. Cancer Inst.* 80: 1553-1559, 1988.

As used herein, the term "clinical response" means any or all of the following: a quantitative measure of the response, no response, and adverse response (i.e., side effects).

As used here, in the term "clinical trial" means any research study designed to collect clinical data on responses to a particular treatment, and includes, but is not limited to phase I, phase II, and phase III clinical trials. Standard methods are used to define the patient population and to enroll subjects.

As used herein, the term "consensus FR" means a framework (FR) antibody region in a consensus immunoglobulin sequence. The FR regions of an antibody do not contact the antigen.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen binding sites. Diabodies are described more fully in, e.g., EP 404,097; WO 93/11161; and 30 Hollinger et al., *Proc. Natl. Acad. Sci. USA*, 90: 6444-6448 (1993).

As used herein, the term "effector cell" means an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens. An effector cell can also phagocytose a target antigen, target cell, metastatic cancer cell, or microorganism.

As used herein, the term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. In one embodiment, an "epitope" of gelsolin is a region in the gelsolin protein to which the gelsolin binding agent of the invention binds. In select embodiments of the invention, this epitope is in the domain spanning amino acid residues from about 321 to about 330, from about 636 to about 645, or from about 661 to 670 of SEQ ID NO.: 1.

To screen for gelsolin binding agents which bind to an epitope, a routine cross-blocking assay such as that described in Antibodies, *A Laboratory Manual*, Cold Spring Harbor Laboratory, Ed Harlow and David Lane (1988), can be performed. This assay can be used to determine if a gelsolin binding agent binds the same site or epitope as a gelsolin antibody of the invention. Alternatively, or additionally, epitope mapping can be performed by methods known in the art. For example, the antibody sequence can be mutagenized such as by alanine scanning, to identify contact residues. In a different method, peptides corresponding to different regions of gelsolin can be used in competition assays with the test antibodies or with a test antibody and an antibody with a characterized or known epitope.

As used herein, the term "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated, e.g., the diseases or medical conditions associated with target polypeptide (e.g. gelsolin or gelsolin-like polypeptides). The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds. In the methods of the present invention, gelsolin may be administered to a subject having decreased gelsolin levels caused by a disease or traumatic condition, thereby increasing the level of plasma gelsolin in the subject. For example, a "therapeutically effective amount" of gelsolin is meant levels in which the toxic effects of free extracellular actin are, at a minimum, ameliorated.

As used herein, "expression" includes but is not limited to one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gelsolin" refers to a multifunctional actin binding protein. In mammals, gelsolin is comprises two isoforms: cytoplasmic and extracellular variants. Human plasma gelsolin differs from cellular gelsolin only by the addition of about 25 amino acids to the N-terminus of the molecule and both gelsolins are the product of a single gene. Plasma gelsolin has three actin-binding sites and binds with high affinity to either G-actin or F-actin. "Gelsolin" also refers to recombinant forms of the mammalian polypeptide.

As used herein, the term "gene" means a segment of DNA that contains all the information for the regulated biosynthesis of an RNA product, including promoters, exons, introns, and other untranslated regions that control expression.

As used herein, the term "human sequence antibody" includes antibodies having variable and constant regions (if present) derived from human germline immunoglobulin sequences. The human sequence antibodies of the invention can include amino acid residues not encoded by human germline immunoglobulin sequences (e.g., mutations introduced by random or site-specific mutagenesis in vitro or by somatic mutation in vivo). Such antibodies can be generated in non-human transgenic animals, e.g., as described in PCT Publication Nos. WO 01/14424 and WO 00/37504. However, the term "human sequence antibody", as used herein, is not intended to include antibodies in which CDR sequences derived from the germline of another mammalian species, such as a mouse, have been grafted onto human framework sequences (e.g., humanized antibodies).

As used herein, the term "humanized" forms of non-human (e.g., murine) antibodies are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR are typically no more than 6 in the H chain, and in the L chain, no more than 3. The humanized antibody optionally also will comprise at least a portion of an immunoglobulin constant region (Fc), typically that of a human immunoglobulin. For further details, see Jones et al., *Nature* 321:522-525 (1986); Reichmann et al., *Nature* 332:323-329 (1988); and Presta, Curr. Op. Struct. Biol. 2:593-596 (1992).

"Amino acid sequence modification(s)" of the gelsolin antibodies described herein are contemplated. For example, it may be desirable to improve the binding affinity and/or other biological properties of the antibody. Amino acid sequence variants of a gelsolin antibody are prepared by introducing appropriate nucleotide changes into the antibody nucleic acid, or by peptide synthesis. Such modifications include, for example, deletions from, and/or insertions into and/or substitutions of, residues within the amino acid sequences of the gelsolin antibody. Any combination of deletion, insertion, and substitution is made to obtain the antibody of interest, as long as the obtained antibody possesses the desired properties. The modification also includes the change of the pattern of glycosylation of the protein. A useful method for identification of preferred locations for mutagenesis is called "alanine scanning mutagenesis" as described by Cunningham and Wells in Science, 244: 1081-1085 (1989). The mutated antibody is then screened for the desired activity, The invention includes antibody variants with one or more amino acid addition, deletion and/or substitution of the amino acid sequence defined by hybridomas GC1C10, GN3E9, or GF2D6 having CGMCC Accession Numbers 2114, 2115, 2116, respectively, provided that the antibody variant possesses the desired properties.

As used herein, the term "hypervariable region" refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 52A-55 (H2) and 96-101 (H3) in the $V_H$ (Chothia and Lesk *J. Mol. Biol.* 196: 901-917 (1987)).

As used herein, the terms "identical" or percent "identity", when used in the context of two or more nucleic acids or polypeptide sequences, refers to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." This term also refers to, or can be applied to, the complement of a test sequence. The term also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An "isolated" or "purified" polypeptide or biologically-active portion thereof is substantially free of cellular material or other contaminating polypeptides from the cell or tissue source from which the gelsolin binding agent is derived, or substantially free from chemical precursors or other chemicals when chemically synthesized. For example, an isolated gelsolin binding agent which is an anti-gelsolin or anti-gelsolin-like antibody would be free of materials that would interfere with diagnostic or therapeutic uses of the agent. Such interfering materials may include enzymes, hormones and other proteinaceous and nonproteinaceous solutes. Alternatively, an isolated gelsolin or gelsolin-like polypeptide, which is immunoractive with a gelsolin binding agent of the invention, would be substantially free of materials that would interfere with diagnostic or therapeutic uses of the polypeptide.

As used herein, the term "intact antibody" means an antibody that has at least two heavy (H) chain polypeptides and two light (L) chain polypeptides interconnected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: $FR_1$, $CDR_1$, $FR_2$, $CDR_2$, $FR_3$, $CDR_3$, $FR_4$. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

As used herein, the term "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, malignant melanoma, invading pathogens, cells or tissues infected with pathogens, or, in cases of autoimmunity or pathological inflammation, normal human cells or tissues.

As used herein, the terms "immunologically cross-reactive" and "immunologically-reactive" are used interchangeably to mean an antigen which is specifically reactive with an antibody which was generated using the same ("immunologically-reactive") or different ("immunologically cross-reactive") antigen. Generally, the antigen is gelsolin polypeptide, a variant or subsequence thereof.

As used herein, the term "immunologically-reactive conditions" means conditions which allow an antibody, generated to a particular epitope of an antigen, to bind to that epitope to a detectably greater degree than the antibody binds to substantially all other epitopes, generally at least two times above background binding, preferably at least five times above background. Immunologically-reactive conditions are dependent upon the format of the antibody binding reaction and typically are those utilized in immunoassay protocols. See, Harlow & Lane, *Antibodies, A Laboratory Manual* (Cold Spring Harbor Publications, New York, 1988) for a description of immunoassay formats and conditions.

As used herein, the term "lymphocyte" means any of the mononuclear, nonphagocytic leukocytes, found in the blood, lymph, and lymphoid tissues, e.g., B and T lymphocytes.

As used herein, the term "medical condition" includes, but is not limited to, any condition or disease manifested as one or more physical and/or psychological symptoms for which treatment and/or prevention is desirable, and includes previously and newly identified diseases and other disorders. For example, a medical condition may be hepatitis, SLE, cancer, septic shock, stroke, heart infarction, and side effects of chemotherapy and radiation therapy.

The term "monoclonal antibody" as used herein refers to an antibody obtained from a population of substantially homogeneous antibodies, i.e., the individual antibodies comprising the population are identical except for possible naturally occurring mutations that may be present in minor amounts. For example, a monoclonal antibody can be an antibody that is derived from a single clone, including any eukaryotic, prokaryotic, or phage clone, and not the method by which it is produced. A monoclonal antibody composition displays a single binding specificity and affinity for a particular epitope. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibodies can be prepared using a wide variety of techniques known in the art including, e.g., but not limited to, hybridoma, recombinant, and phage display technologies. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration.

As used herein, the term "polyclonal antibody" means a preparation of antibodies derived from at least two (2) different antibody-producing cell lines. The use of this term includes preparations of at least two (2) antibodies that contain antibodies that specifically bind to different epitopes or regions of an antigen.

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons. In a particular embodiment, the polynucleotide contains polynucleotide sequences from a gelsolin gene.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature. In a particular embodiment, the polypeptide contains polypeptide sequences from a gelsolin protein.

As used herein, the term "population" may be any group of at least two individuals. A population may include, e.g. but is not limited to, a reference population, a population group, a family population, a clinical population, and a same sex population.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, e.g., recombinant cells express genes that are not found within the native (non-recombinant) form of the cell or express native genes that are otherwise abnormally expressed, under expressed or not expressed at all.

As used herein, the term "reference standard" is the pattern of expression of one or more genes or proteins observed in either a reference standard population or a single subject prior to administration of a compound.

As used herein, the phrase "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule To increase the serum half life of the antibody, one may incorporate a salvage receptor binding epitope into the antibody (especially an antibody fragment) as described in U.S. Pat. No. 5,739,277, for example.

As used herein, the terms "single chain antibodies" or "single chain Fv (scFv)" refer to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv). See, e.g., Bird et al., *Science* 242: 423-426, 1988; and Huston et al., *Proc. Natl. Acad. Sci. USA*, 85: 5879-5883, 1988). Such single chain antibodies are included by reference to the term "antibody" fragments, and can be prepared by recombinant techniques or enzymatic or chemical cleavage of intact antibodies.

As used herein, the term "small molecule" means a composition that has a molecular weight of less than about 5 kDa and more preferably less than about 2 kDa. Small molecules can be, e.g., nucleic acids, peptides, polypeptides, glycopeptides, peptidomimetics, carbohydrates, lipids, lipopolysaccharides, combinations of these, or other organic or inorganic molecules.

As used herein, the term "specific binding" means the contact between a gelsolin binding agent and an antigen with a binding affinity of at least $10^{-6}$ M. Preferred binding agents bind with affinities of at least about $10^{-7}$ M, and preferably $10^{-8}$ M to $10^{-9}$ M, $10^{-10}$ M, $10^{-11}$ M, or $10^{-12}$ M.

As used herein, the term "subject" means that preferably the subject is a mammal, such as a human, but can also be an animal, e.g., domestic animals (e.g., dogs, cats and the like), farm animals (e.g., cows, sheep, pigs, horses and the like) and laboratory animals (e.g., monkey, rats, mice, rabbits, guinea pigs and the like).

As used herein, the term "substitution" is one of mutations that is generally used in the art. Those substitution variants have at least one amino acid residue in the gelsolin binding antibody molecule replaced by a different residue. The sites of greatest interest for substitutional mutagenesis include the hypervariable regions, but FR alterations are also contemplated. "Conservative substitutions" are shown in the Table below under the heading of "preferred substitutions". If such substitutions result in a change in biological activity, then more substantial changes, denominated "exemplary substitutions" in Table 2, or as further described below in reference to amino acid classes, may be introduced and the products screened.

As used herein, the term "reference standard population" means a population characterized by one or more biological characteristics, e.g., drug responsiveness, genotype, haplotype, phenotype, etc.

As used herein, a "test sample" means a biological sample obtained from a subject of interest. For example, a test sample can be a biological fluid (e.g., serum), cell or tissue sample, sample from culture or growth media, or isolated nucleic acid or polypeptide derived therefrom.

TABLE 2

Amino Acid Substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

A particularly preferred type of substitutional variant involves substituting one or more hypervariable region residues of a parent antibody. A convenient way for generating such substitutional variants involves affinity maturation using phage display. Specifically, several hypervariable region sites (e.g. 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding gelsolin. Alternatively, or additionally, it may be beneficial to analyze a crystal structure of the antigen-antibody complex to identify contact points between the antibody and gelsolin. Such contact residues and neighboring residues are candidates for substitution according to the techniques elaborated herein. Once such variants are generated, the panel of variants is subjected to screening as described herein and antibodies with similar or superior properties in one or more relevant assays may be selected for further development. The invention includes antibody variants with one or more amino acid substitution(s), especially conservative substitutions, to the hypervariable domains of the immunoglobulin heavy or light chain defined by hybridomas GC1C10, GN3E9, GF2D6, having CGMCC Accession Numbers 2114, 2115, and 2116, respectively, provided that the antibody variant possesses the desired properties.

As used herein, the term "therapeutic agent" is intended to mean a compound that, when present in an effective amount, produces a desired therapeutic effect on a subject in need thereof.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for a disorder characterized by decreased gelsolin levels if, after receiving a therapeutic amount of native or recombinant gelsolin according to the methods of the present invention, the subject shows observable and/or measurable reduction in or absence of one or more signs and symptoms of a particular disease or condition. For example, for cancer, reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues.

As used herein, the term "variable" refers to the fact that certain segments of the variable domains differ extensively in sequence among antibodies. The V domain mediates antigen binding and define specificity of a particular antibody for its particular antigen. However, the variability is not evenly distributed across the amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Compositions of the Invention

Gelsolin Binding Agents. In one aspect, the present invention provides gelsolin binding agent compositions, a.k.a., the binding agent. In one embodiment, the binding agent of the invention is an intact antibody directed to a gelsolin polypeptide, homolog, fragment, or derivative thereof. The binding agents of interest may be ones which bind specifically to free, full-length, active gelsolin, but do not "substantively" (or "substantially") bind gelsolin which are bound to actin. In such embodiments, the extent of binding of the binding agent of the invention to these proteins will be less than about 10%, preferably, or less than about 5%, or less than about 1%, as determined by fluorescence activated cell sorting (FACS) analysis, ELISA, Western blot, or radioimmunoassay.

Prior efforts to generate monoclonal antibodies with defined epitopes (in particular, eptiopes associated with functional gelsolin) have been largely unsuccessful. Gelsolin is a highly conserved protein and highly homologous among species. Gelsolin is also abundant in plasma, which requires that it be well-tolerated by the immune system. Furthermore, due to the fact that gelsolin is a major actin binding protein, the exposed epitopes are limited by the complexing of gelsolin with actin and other plasma proteins. Although some monoclonal antibodies to gelsolin have been produced (see Hiyoshi et al., *Biochem Mol Biol Int*. 32:755-62 (1994)), there is no immunoassay for quantitative measurement of plasma gelsolin.

The present inventors have discovered a strategy to design gelsolin binding agents using various forms of human gelsolin proteins for both immunization and screening, including native gelsolin, recombinant full-length gelsolin, and N- and C-terminal gelsolin fragments. Moreover, the inventors' strategy is designed to break the immune tolerance to common epitopes of human gelsolin using modulators of the immune response. The result of this strategy are gelsolin binding agents with defined epitopes that allow for rapid, accurate, and quantitative assays for plasma gelsolin which can be used in a clinical setting.

Binding agents of the present invention can be described or specified in terms of the epitope(s) or portion(s) of a polypeptide of the present invention which are recognized or specifically bound by the binding agent, e.g., a region of the gelsolin polypeptide that is located on the surface of the polypeptide (e.g., a hydrophilic region). In one embodiment, the invention provides gelsolin binding agents, e.g., antibodies or antibody-related polypeptides directed to a gelsolin polypeptide (a.k.a., a target polypeptide) comprising one or more amino acid sequences selected from the group consisting of: FAQGALKSED (SEQ ID NO.: 2), SEPDGFWEAL (SEQ ID NO.: 3), ACSNKIGRFV (SEQ ID NO.: 4).

In select embodiments, the invention provides the gelsolin binding agents summarized in Table 3.

TABLE 3

Select Gelsolin Receptor-Binding Agents

| Binding Agent | Type | Description |
|---|---|---|
| GN3E9 | Murine Monoclonal Antibody | Murine monoclonal antibody directed to an epitope comprising a polypeptide sequence of FAQGALKSED (SEQ ID NO.: 2). |
| GC1C10 | Murine Monoclonal Antibody | Murine monoclonal antibody directed to an epitope comprising a polypeptide sequence of SEPDGFWEAL (SEQ ID NO.: 3). |
| GF2D6 | Murine Monoclonal Antibody | Murine monoclonal antibody directed to a epitope with a polypeptide sequence of ACSNKIGRFV (SEQ ID NO.: 4). |

Deposits of biological materials associated with the gelsolin binding agents summarized in Table 5 (above) were made with the China General Microbiological Culture Collection Center (CGMCC), China Committee for Culture Collection of Microorganisms, P.O. Box 2714, Beijing 100080, The People's Republic of China as detailed in Table 4 below.

TABLE 4

Biological Deposits

| Name of Deposit | Materials | Date | Accession Number |
|---|---|---|---|
| GN3E9 | Mouse-mouse hybridoma | Jul. 20, 2007 | 2115 |
| GC1C10 | Mouse-mouse hybridoma | Jul. 20, 2007 | 2114 |
| GF2D6 | Mouse-mouse hybridoma | Jul. 20, 2007 | 2116 |

In another embodiment, the present invention affords a method of elucidating other epitopes of gelsolin, which can be used for generation of an antibody having the desired characteristics of binding to active gelsolin, but not gelsolin bound to actin. The binding agents directed against the epitope may have a differing variable or CDR region but should have the binding and functional characteristics of the antibodies of the present invention. As a means for targeting antibody production, hydropathy plots showing regions of hydrophilicity and hydrophobicity can be generated by any method well known in the art, including, e.g., the Kyte Doolittle or the Hopp Woods methods, either with or without Fourier transformation (see, e.g., Hopp and Woods, *Proc. Nat. Acad. Sci. USA* 78: 3824-3828 (1981); Kyte and Doolittle, *J. Mol. Biol.* 157: 105-142 (1982)). The epitope(s) or polypeptide portion(s) can be specified as described herein, e.g., by N-terminal and C-terminal positions, by size in contiguous amino acid residues. The present invention includes binding agents that specifically bind polypeptides of the present invention, and allows for the exclusion of the same.

The present invention includes binding agents that specifically bind epitopes which are conformational epitopes or nonconformational epitopes. As noted above, conformational epitopes or nonconformational epitopes are distinguished in that the binding to the former but not the latter is lost in the presence of denaturing solvents.

Binding agents of the present invention can also be described or specified in terms of their cross-reactivity. Binding agents that do not bind any other analog, ortholog, or homolog of the target polypeptide of the present invention are included. Binding agents that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are binding agents which only bind polypeptides encoded by polynucleotides which hybridize to a polynucleotide of the present invention under stringent hybridization conditions (as described herein).

Binding agents of the present invention can also be described or specified in terms of their binding affinity. Preferred binding affinities include those with a dissociation constant or $K_d$ less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $10^{-14}$, $5\times10^{-15}$M, and $10^{-15}$M. In one embodiment, the invention provides gelsolin binding agents that at least bind human gelsolin with a $K_d$ value of no higher than $1\times10^{-8}$, preferably a $K_d$ value no higher than about $1\times10^{-9}$.

Gelsolin binding agents within the scope of the present invention include, e.g., but are not limited to, monoclonal, polyclonal, chimeric, humanized, diabody, and human monoclonal and human polyclonal antibodies which specifically bind the target polypeptide, a homolog, derivative or a fragment thereof. As used herein, a "gelsolin-like polypeptide" means a polypeptide that is different from gelsolin polypeptide but which is immunologically-reactive with a gelsolin binding agent of the invention. A gelsolin-like polypeptide may be derived from the same organism or a different organism as a gelsolin polypeptide. A gelsolin-like polypeptide may be encoded by the same gene or a different gene as a gelsolin polypeptide. The antibodies useful as binding agents of the present invention include, e.g., but are not limited to, IgG (including $IgG_1$, $IgG_2$, $IgG_3$, and $IgG_4$), IgA (including $IgA_1$ and $IgA_2$), IgD, IgE, or IgM, and IgY.

In another embodiment, the binding agent of the invention is an antibody-related polypeptide directed to gelsolin polypeptide, homolog or derivative thereof. Typically, the antigen-binding region of a binding agent, e.g., the anti-gelsolin binding region, will be most critical in specificity and affinity of binding of the binding agent of the invention. In some embodiments, the gelsolin binding agent is an anti-gelsolin polypeptide antibody, such as an anti-gelsolin polypeptide monoclonal antibody, an anti-gelsolin polypeptide chimeric antibody, and an anti-gelsolin polypeptide humanized antibody which have been modified by, e.g., deleting, adding, or substituting portions of the antibody. For example, an anti-gelsolin polypeptide antibody intended meant to increase half-life, e.g., serum half-life, stability or affinity of the antibody.

In one embodiment, selection of antibodies that are specific to a particular domain of a gelsolin polypeptide is facilitated by generation of hybridomas that bind to the fragment of a gelsolin polypeptide possessing such a domain. Thus, gelsolin binding agents which are antibodies that are specific for a desired domain within a gelsolin polypeptide, or derivatives, fragments, analogs or homologs thereof, are also provided herein.

The present invention further includes antibodies which are anti-idiotypic to the binding agents of the present invention. The binding agents of the present invention can be monospecific, bispecific, trispecific or of greater multispecificity. Multispecific binding agents can be specific for different epitopes of a gelsolin polypeptide of the present invention or can be specific for both a gelsolin polypeptide of the present invention as well as for heterologous compositions, such as a heterologous polypeptide or solid support material. See, e.g., WO 93/17715; WO 92/08802; WO 91/00360; WO 92/05793; Tutt et al., *J. Immunol.* 147: 60-69 (1991); U.S. Pat. Nos. 5,573,920, 4,474,893, 5,601,819, 4,714,681, 4,925,648; 6,106,835; Kostelny et al., *J. Immunol.* 148: 1547-1553 (1992). The binding agents of the invention can be from any animal origin including birds and mammals. Preferably, the binding agents are human, murine, rabbit, goat, guinea pig, camel, horse, or chicken.

The binding agents of the present invention can be used either alone or in combination with other compositions. For example, the gelsolin binding agents of the invention can be used in combination with one or more anti-gelsolin antibodies known in the art, e.g., but not limited to antibody GS-2C4 (Sigma-Aldrich, Cat. No. G4896; Afify and Werness. *Appl. Immunohistochem.* 6:30, (1998)).

The gelsolin binding agents of the present invention can further be recombinantly fused to a heterologous polypeptide at the N- or C-terminus or chemically conjugated (including covalently and non-covalently conjugations) to polypeptides or other compositions. For example, gelsolin binding agents of the present invention can be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

In certain embodiments, the gelsolin binding agents of the present invention are anti-gelsolin antibodies or anti-gelsolin antibody-related polypeptides that are coupled or conjugated to one or more therapeutic or cytotoxic moieties to yield a gelsolin binding agent conjugate protein of the invention. The gelsolin binding agent conjugate protein of the invention can be used to modify a given biological response or create a biological response (e.g., to recruit effector cells). The therapeutic moiety is not to be construed as limited to classical chemical therapeutic agents. For example, the therapeutic moiety can be a protein or polypeptide possessing a desired biological activity. Such proteins can include, e.g., an enzymatically active toxin, or active fragment thereof, such as abrin, ricin A, *Pseudomonas* exotoxin, or diphtheria toxin; a protein such as tumor necrosis factor or interferon-alpha; or, biological response modifiers such as, e.g., lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Methods of Preparing a Gelsolin-Binding Agents of the Invention

General Overview. Initially, a target polypeptide is chosen to which a binding agent of the invention (e.g., anti-gelsolin receptor antibody) can be raised. Techniques for generating binding agents directed to target polypeptides are well known to those skilled in the art. Examples of such techniques include, e.g., but are not limited to, those involving display libraries, xeno or humab mice, hybridomas, and the like. Target polypeptides within the scope of the present invention include any polypeptide or polypeptide derivative which is capable of exhibiting antigenicity. Examples include, but are not limited to gelsolin, peptides, polypeptides, and fragments thereof.

It should be understood that not only are naturally-occurring antibodies suitable as binding agents for use in accordance with the present disclosure, but recombinantly engineered antibodies and antibody fragments, e.g., antibody-related polypeptides, which are directed to gelsolin polypeptide and fragments thereof are also suitable.

Binding agents, e.g., anti-gelsolin antibodies, that can be subjected to the techniques set forth herein include monoclonal and polyclonal antibodies, and antibody fragments such as Fab, Fab', F(ab')$_2$, Fd, scFv, diabodies, antibody light chains, antibody heavy chains and/or antibody fragments. Methods useful for the high yield production of antibody Fv-containing polypeptides, e.g., Fab' and F(ab')$_2$ antibody fragments have been described. See U.S. Pat. No. 5,648,237.

Generally, a binding agent is obtained from an originating species. More particularly, the nucleic acid or amino acid sequence of the variable portion of the light chain, heavy chain or both, of an originating species antibody having specificity for a target polypeptide antigen is obtained. Originating species is any species which was useful to generate the binding agent of the invention or library of binding agents, e.g., rat, mice, rabbit, chicken, monkey, human, and the like.

In preferred embodiments, gelsolin binding agents are anti-gelsolin antibodies. Phage or phagemid display technologies are useful techniques to derive the binding agents of the present invention. Anti-gelsolin antibodies useful in the present invention are "human antibodies," (e.g., antibodies isolated from a human) or "human sequence antibodies." Human antibodies can be made by a variety of methods known in the art including phage display methods. See also, U.S. Pat. Nos. 4,444,887, 4,716,111, 5,545,806, and 5,814,318; and WO 98/46645, WO 98/50433, WO 98/24893, WO 98/16654, WO 96/34096, WO 96/33735, and WO 91/10741. Methods useful for the identification of nucleic acid sequences encoding members of multimeric polypeptide complex by screening polyphage particles have been described. Rudert et al., U.S. Pat. No. 6,667,150. Also, recombinant immunoglobulins can be produced. Cabilly, U.S. Pat. No. 4,816,567; Cabilly et al., U.S. Pat. No. 6,331,415 and Queen et al., Proc. Natl. Acad. Sci. USA 86: 10029-10033, 1989. Techniques for generating and cloning monoclonal antibodies are well known to those skilled in the art. The gelsolin binding agents of the invention preferably have a high immunoreactivity, that is, percentages of antibodies molecules that are correctly folded so that they can specifically bind their target antigen. Expression of sequences encoding binding agents, e.g., antibodies of the invention, can be carried out in E. coli as described below. Such expression usually results in immunoreactivity of at least 80%, 90%, 95% or 99%.

Certain truncations of these proteins or genes perform the regulatory or enzymatic functions of the full sequence protein or gene. For example, the nucleic acid sequences coding therefore can be altered by substitutions, additions, deletions or multimeric expression that provide for functionally equivalent proteins or genes. Due to the degeneracy of nucleic acid coding sequences, other sequences which encode substantially the same amino acid sequences as those of the naturally occurring proteins may be used in the practice of the present invention. These include, but are not limited to, nucleic acid sequences including all or portions of the nucleic acid sequences encoding the above polypeptides, which are altered by the substitution of different codons that encode a functionally equivalent amino acid residue within the sequence, thus producing a silent change. It is appreciated that the nucleotide sequence of an immunoglobulin according to the present invention tolerates sequence homology variations of up to 25% as calculated by standard methods ("Current Methods in Sequence Comparison and Analysis," Macromolecule Sequencing and Synthesis, Selected Methods and Applications, pp. 127-149, 1998, Alan R. Liss, Inc.) so long as such a variant forms an operative antibody which recognizes gelsolin or gelsolin-like polypeptides. For example, one or more amino acid residues within a polypeptide sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the present invention are proteins or fragments or derivatives thereof which are differentially modified during or after translation, e.g., by glycosolation, protolytic cleavage, linkage to an antibody molecule or other cellular ligands, etc. Additionally, an inhibitor encoding nucleic acid sequence can be mutated in vitro or in vivo to create and/or destroy translation, initiation, and/or termination sequences or to create variations in coding regions and/or form new restriction endonuclease sites or destroy pre-existing ones, to facilitate further in vitro modification. Any technique for mutagenesis known in the art can be used, including but not limited to in vitro site directed mutagenesis, J. Biol. Chem. 253:6551, use of Tab linkers (Pharmacia), and the like.

Preparation of Polyclonal Antisera and Immunogens. Methods of generating antibodies or antibody fragments of the invention typically include immunizing a subject (generally a non-human subject such as a mouse or rabbit) with a purified gelsolin or gelsolin-like polypeptide or homolog or fragment thereof or with a cell expressing the gelsolin or gelsolin-like polypeptide or homolog or fragment thereof. Any immunogenic portion of the gelsolin polypeptide can be employed as the immunogen. An appropriate immunogenic preparation can contain, e.g., a recombinantly-expressed gelsolin polypeptide or a chemically-synthesized gelsolin polypeptide. An isolated gelsolin polypeptide, or a portion or fragment thereof, can be used as an immunogen to generate a gelsolin binding agent that binds to the gelsolin polypeptide, or a portion or fragment using standard techniques for polyclonal and monoclonal antibody preparation. The full-length gelsolin polypeptide can be used or, alternatively, the invention provides for the use of the gelsolin polypeptide fragments as immunogens. The gelsolin polypeptide comprises at least four amino acid residues of the amino acid sequence shown in SEQ ID NO.: 1, and encompasses an epitope of the gelsolin polypeptide such that an antibody raised against the peptide forms a specific immune complex with the gelsolin polypeptide. Preferably, the antigenic peptide comprises at least 5, 8, 10, 15, 20, or 30 amino acid residues. Longer antigenic peptides are sometimes preferable over shorter antigenic peptides, depending on use and according to methods well known to those skilled in the art. Typically, the immunogen will be at least about 8 amino acyl residues in length, and preferably at least about 10 acyl residues in length. Multimers of a given epitope are sometimes more effective than a monomer.

If needed, the immunogenicity of the gelsolin polypeptide (or fragment thereof) can be increased by fusion or conjugation to a hapten such as keyhole limpet hemocyanin (KLH) or ovalbumin (OVA). Many such haptens are known in the art. One can also combine the gelsolin polypeptide with a conventional adjuvant such as Freund's complete or incomplete adjuvant to increase the subject's immune reaction to the polypeptide. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory compounds. These techniques are standard in the art.

For convenience, immune responses are often described in the present invention as being either "primary" or "secondary" immune responses. A primary immune response, which is also described as a "protective" immune response, refers to an immune response produced in an individual as a result of some initial exposure (e.g., the initial "immunization") to a particular antigen, e.g., a gelsolin polypeptide. Such an immunization can occur, e.g., as the result of some natural exposure to the antigen (e.g., from initial infection by some pathogen that exhibits or presents the antigen) or from antigen presented by cancer cells of some tumor in the individual (e.g., malignant melanoma). Alternatively, the immunization can occur as a result of vaccinating the individual with a vaccine containing the antigen. For example, the vaccine can be a gelsolin vaccine comprising one or more antigens from a gelsolin polypeptide or a gelsolin-like polypeptide.

A primary immune response can become weakened or attenuated over time and can even disappear or at least become so attenuated that it cannot be detected. Accordingly, the present invention also relates to a "secondary" immune response, which is also described here as a "memory immune response." The term secondary immune response refers to an immune response elicited in an individual after a primary immune response has already been produced.

Thus, a secondary or immune response can be elicited, e.g., to enhance an existing immune response that has become weakened or attenuated, or to recreate a previous immune response that has either disappeared or can no longer be detected. The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by CD4$^+$ cells. A first exposure to an antigen primes the immune system and additional exposure(s) results in a DTH.

Following appropriate immunization, the gelsolin binding agent, e.g., anti-gelsolin polyclonal antibody can be prepared from the subject's serum. If desired, the antibody molecules directed against the gelsolin polypeptide can be isolated from the mammal (e.g., from the blood) and further purified by well known techniques, such as polypeptide A chromatography to obtain the IgG fraction.

Monoclonal Antibody. In one embodiment of the present invention, the binding agent is an anti-gelsolin monoclonal antibody. For example, in some embodiments, the anti-gelsolin monoclonal antibody may be a human or a mouse anti-gelsolin monoclonal antibody. For preparation of monoclonal antibodies directed towards a particular gelsolin polypeptide, or derivatives, fragments, analogs or homologs thereof, any technique that provides for the production of antibody molecules by continuous cell line culture can be utilized. Such techniques include, but are not limited to, the hybridoma technique (see, e.g., Kohler & Milstein, 1975. Nature 256: 495-497); the trioma technique; the human B-cell hybridoma technique (see, e.g., Kozbor, et al., 1983. Immunol. Today 4: 72) and the EBV hybridoma technique to produce human monoclonal antibodies (see, e.g., Cole, et al., 1985. In: MONOCLONAL ANTIBODIES AND CANCER THERAPY, Alan R. Liss, Inc., pp. 77-96). Human monoclonal antibodies can be utilized in the practice of the invention and can be produced by using human hybridomas (see, e.g., Cote, et al., 1983. Proc. Natl. Acad. Sci. USA 80: 2026-2030) or by transforming human B-cells with Epstein Barr Virus in vitro (see, e.g., Cole, et al., 1985. In: MONOCLONAL ANTIBODIES AND CANCER THERAPY, Alan R. Liss, Inc., pp. 77-96). For example, a population of nucleic acids that encode regions of antibodies can be isolated. PCR utilizing primers derived from sequences encoding conserved regions of antibodies is used to amplify sequences encoding portions of antibodies from the population and then reconstruct DNAs encoding antibodies or fragments thereof, such as variable domains, from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the gelsolin polypeptide. Alternatively, hybridomas expressing anti-gelsolin monoclonal antibodies can be prepared by immunizing a subject and then isolating hybridomas from the subject's spleen using routine methods. See, e.g., Milstein et al., (Galfre and Milstein, *Methods Enzymol* (1981) 73: 3-46). Screening the hybridomas using standard methods will produce monoclonal antibodies of varying specificity (i.e., for different epitopes) and affinity. A selected monoclonal antibody with the desired properties, e.g., gelsolin binding, can be used as expressed by the hybridoma, it can be bound to a molecule such as polyethylene glycol (PEG) to alter its properties, or a cDNA encoding it can be isolated, sequenced and manipulated in various ways. Synthetic dendroineric trees can be added a reactive amino acid side chains, e.g., lysine to enhance the immunogenic properties of the gelsolin polypeptide. Also, CPG-dinucleotide technique can be used to enhance the immunogenic properties of the gelsolin polypeptide. Other manipulations include substituting or deleting particular amino acyl residues that contribute to instability of the antibody during storage or after administration to a subject, and affinity maturation techniques to improve affinity of the antibody of the gelsolin polypeptide.

Hybridoma Technique. In one embodiment, the binding agent of the invention is an anti-gelsolin monoclonal antibody produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al., *Antibodies: A Laboratory Manual* Cold Spring Harbor Laboratory, Cold Spring Harbor, N.Y., 349 (1988); Hammerling et al., *Monoclonal Antibodies And T-Cell Hybridomas,* 563-681 (1981). Other methods for producing hybridomas and monoclonal antibodies are well known to those of skill in the art.

Phage Display Technique. As noted above, the binding agents of the present invention can be produced through the application of recombinant DNA and phage display technology. For example, binding agents of the invention, e.g., anti-gelsolin antibodies, can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g., human or murine) by selecting directly with antigen, typically antigen bound or captured to a solid surface or bead. Phage used in these methods are typically filamentous phage including fd and M13 with Fab, Fv or disulfide stabilized Fv antibody domains are recombinantly fused to either the phage gene III or gene VIII protein. In addition, methods can be adapted for the construction of Fab expression libraries (see, e.g., Huse, et al., Science 246: 1275-1281, 1989) to allow rapid and effective identification of monoclonal Fab fragments with the desired specificity for a gelsolin polypeptide, e.g., a polypeptide or derivatives, fragments, analogs or homologs thereof. Other examples of phage display methods that can be used to make the binding agents of the present invention include those disclosed in Huston et al., *Proc. Natl. Acad. Sci. U.S.A.*, 85: 5879-5883, 1988; Chaudhary et al., *Proc. Natl. Acad. Sci. U.S.A.,* 87: 1066-1070, 1990; Brinkman et al., *J. Immunol. Methods* 182: 41-50, 1995; Ames et al., *J. Immunol. Methods* 184: 177-186, 1995; Kettleborough et al., *Eur. J. Immunol.* 24: 952-958, 1994; Persic et al., *Gene* 187: 9-18, 1997; Burton et al., *Advances in Immunology* 57: 191-280, 1994; PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580, 717, 5,427,908, 5,750,753, 5,821,047, 5,571,698, 5,427,908, 5,516,637, 5,780,225, 5,658,727 and 5,733,743. Methods useful for displaying polypeptides on the surface of bacteriophage particles by attaching the polypeptides via disulfide bonds have been described by Lohning, U.S. Pat. No. 6,753, 136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')$_2$ fragments can also be employed using methods known in the art such as those disclosed in WO 92/22324; Mullinax et al., *BioTechniques* 12: 864-869, 1992; and Sawai et al., *AJRI* 34: 26-34, 1995; and Better et al., *Science* 240: 1041-1043, 1988.

Generally, hybrid antibodies or hybrid antibody fragments that are cloned into a display vector can be selected against the appropriate antigen in order to identify variants that maintained good binding activity, because the antibody or antibody fragment will be present on the surface of the phage or phagemid particle. See e.g. Barbas III et al., *Phage Display, A Laboratory Manual* (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Expression of Recombinant Gelsolin-Binding Agent. As noted above, the binding agents of the present invention can be produced through the application of recombinant DNA technology. Recombinant polynucleotide constructs encoding a gelsolin binding agent of the present invention typically include an expression control sequence operably-linked to the coding sequences of anti-gelsolin antibody chains, including naturally-associated or heterologous promoter regions. As such, another aspect of the invention includes vectors containing one or more nucleic acid sequences encoding a gelsolin binding agent of the present invention. For recombinant expression of one or more the polypeptides of the invention, the nucleic acid containing all or a portion of the nucleotide sequence encoding the gelsolin binding agent is inserted into an appropriate cloning vector, or an expression vector (i.e., a vector that contains the necessary elements for the transcription and translation of the inserted polypeptide coding sequence) by recombinant DNA techniques well known in the art and as detailed below. Methods for producing diverse populations of vectors have been described by Lerner et al., U.S. Pat. Nos. 6,291,160; 6,680,192.

In general, expression vectors useful in recombinant DNA techniques are often in the form of plasmids. In the present specification, "plasmid" and "vector" can be used interchangeably as the plasmid is the most commonly used form of vector. However, the invention is intended to include such other forms of expression vectors that are not technically plasmids, such as viral vectors (e.g., replication defective retroviruses, adenoviruses and adeno-associated viruses), which serve equivalent functions. Such viral vectors permit infection of a subject and expression in that subject of a compound. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences encoding the gelsolin binding agent, and the collection and purification of the gelsolin binding agent, e.g., cross-reacting anti-gelsolin antibodies. See, generally, U.S. Application No. 20020199213. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. Vectors can also encode signal peptide, e.g., pectate lyase, useful to direct the secretion of extracellular antibody fragments. See U.S. Pat. No. 5,576,195.

The recombinant expression vectors of the invention comprise a nucleic acid encoding a compound with gelsolin binding properties in a form suitable for expression of the nucleic acid in a host cell, which means that the recombinant expression vectors include one or more regulatory sequences, selected on the basis of the host cells to be used for expression that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, e.g., in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. Typical regulatory sequences useful as promoters of recombinant polypeptide expression (e.g., gelsolin binding agents), include, e.g., but are not limited to, 3-phosphoglycerate kinase and other glycolytic enzymes. Inducible yeast promoters include, among others, promoters from alcohol dehydrogenase, isocytochrome C, and enzymes responsible for maltose and galactose utilization. In one embodiment, a polynucleotide encoding a gelsolin binding agent of the invention is operably-linked to an ara B promoter and expressible in a host cell. See U.S. Pat. No. 5,028,530. The expression vectors of the invention can be introduced into host cells to thereby produce polypeptides or peptides, including fusion polypeptides, encoded by nucleic acids as described herein (e.g., gelsolin binding agents, etc.).

Another aspect of the invention pertains to gelsolin binding agent-expressing host cells, which contain a nucleic acid encoding one or more gelsolin binding agents. The recombinant expression vectors of the invention can be designed for expression of a gelsolin binding agent in prokaryotic or eukaryotic cells. For example, a gelsolin binding agent can be expressed in bacterial cells such as $Escherichia\ coli$, insect cells (using baculovirus expression vectors), fungal cells, e.g., yeast, yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, e.g. using T7 promoter regulatory sequences and T7 polymerase. Methods useful for the preparation screening of polypeptides having predetermined property, e.g., gelsolin binding agents, via expression of stochastically generated polynucleotide sequences has been described. See U.S. Pat. Nos. 5,763,192; 5,723,323; 5,814,476; 5,817,483; 5,824,514; 5,976,862; 6,492,107; 6,569,641.

Expression of polypeptides in prokaryotes is most often carried out in $E.\ coli$ with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione 5-transferase (GST), maltose E binding polypeptide, or polypeptide A, respectively, to the target recombinant polypeptide.

Examples of suitable inducible non-fusion $E.\ coli$ expression vectors include pTrc (Amrann et al., (1988) Gene 69: 301-315) and pET 11d (Studier et al., GENE EXPRESSION TECHNOLOGY: METHODS IN ENZYMOLOGY 185, Academic Press, San Diego, Calif. (1990) 60-89). Methods for targeted assembly of distinct active peptide or protein domains to yield multifunctional polypeptides via polypeptide fusion has been described by Pack et al., U.S. Pat. Nos. 6,294,353; 6,692,935. One strategy to maximize recombinant polypeptide expression, e.g., a gelsolin binding agent, in $E.\ coli$ is to express the polypeptide in host bacteria with an impaired capacity to proteolytically cleave the recombinant polypeptide. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression host, e.g., $E.\ coli$ (see, e.g., Wada, et al., 1992. Nucl. Acids Res. 20: 2111-2118). Such alteration of nucleic acid sequences of the invention can be carried out by standard DNA synthesis techniques.

In another embodiment, the gelsolin binding agent expression vector is a yeast expression vector. Examples of vectors for expression in yeast $Saccharomyces\ cerivisae$ include pYepSec1 (Baldari, et al., 1987. EMBO J. 6: 229-234), pMFa (Kurjan and Herskowitz, Cell 30: 933-943, 1982), pJRY88 (Schultz et al., Gene 54: 113-123, 1987), pYES2 (Invitrogen Corporation, San Diego, Calif.), and picZ (InVitrogen Corp, San Diego, Calif.). Alternatively, a gelsolin binding agent can be expressed in insect cells using baculovirus expression vectors. Baculovirus vectors available for expression of polypeptides, e.g., gelsolin binding agents, in cultured insect cells (e.g., SF9 cells) include the pAc series (Smith, et al., Mol. Cell. Biol. 3: 2156-2165, 1983) and the pVL series (Lucklow and Summers, 1989. Virology 170: 31-39).

In yet another embodiment, a nucleic acid encoding a gelsolin binding agent of the invention is expressed in mammalian cells using a mammalian expression vector. Examples of mammalian expression vectors include, e.g., but are not limited to, pCDM8 (Seed, Nature 329: 840, 1987) and pMT2PC (Kaufman, et al., EMBO J. 6: 187-195, 1987). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells useful for expression of the gelsolin binding agents of the present invention. See, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., Genes Dev. 1: 268-277, 1987), lymphoid-specific promoters (Calame and Eaton, Adv. Immunol. 43: 235-275, 1988), in particular promoters of T cell receptors (Winoto and Baltimore, EMBO J. 8: 729-733, 1989) and immunoglobulins (Banerji, et al., 1983. Cell 33: 729-740; Queen and Baltimore, Cell 33: 741-748, 1983.), neuron-specific promoters (e.g., the neurofilament promoter; Byrne and Ruddle, Proc. Natl. Acad. Sci. USA 86: 5473-5477, 1989), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, *Science* 249: 374-379, 1990) and the α-fetoprotein promoter (Campes and Tilghman, *Genes Dev.* 3: 537-546, 1989).

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a gelsolin binding agent can be expressed in bacterial cells such as *E. coli*, insect cells, yeast or mammalian cells. Mammalian cells are a preferred host for expressing nucleotide segments encoding immunoglobulins or fragments thereof. See Winnacker, *From Genes To Clones*, (VCH Publishers, NY, 1987). A number of suitable host cell lines capable of secreting intact heterologous proteins have been developed in the art, and include Chinese hamster ovary (CHO) cell lines, various COS cell lines, HeLa cells, L cells and myeloma cell lines. Preferably, the cells are nonhuman. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Queen et al., *Immunol. Rev.* 89: 49, 1986. Preferred expression control sequences are promoters derived from endogenous genes, cytomegalovirus, SV40, adenovirus, bovine papillomavirus, and the like. Co et al., *J Immunol.* 148: 1149, 1992. Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation, biolistics or viral-based transfection can be used for other cellular hosts. Other methods used to transform mammalian cells include the use of polybrene, protoplast fusion, liposomes, electroporation, and microinjection (see generally, Sambrook et al., *Molecular Cloning*). Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals. The vectors containing the DNA segments of interest can be transferred into the host cell by well known methods, depending on the type of cellular host.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the gelsolin binding agent or can be introduced on a separate vector. Cells stably transfected with the introduced nucleic acid can be identified by drug selection (e.g., cells that have incorporated the selectable marker gene will survive, while the other cells die).

A host cell that includes a gelsolin binding agent of the present invention, such as a prokaryotic or eukaryotic host cell in culture, can be used to produce (i.e., express) recombinant gelsolin binding agent. In one embodiment, the method comprises culturing the host cell of invention (into which a recombinant expression vector encoding the gelsolin binding agent has been introduced) in a suitable medium such that the gelsolin binding agent is produced. In another embodiment, the method further comprises the step of isolating the gelsolin binding agent from the medium or the host cell. Once expressed, collections of the gelsolin binding agents, e.g., the anti-gelsolin antibodies or the anti-gelsolin antibody-related polypeptides are purified from culture media and host cells. The gelsolin binding agents can be purified according to standard procedures of the art, including HPLC purification, column chromatography, gel electrophoresis and the like. In one embodiment, the gelsolin binding agent is produced in a host organism by the method of Boss et al., U.S. Pat. No. 4,816,397. Usually, anti-gelsolin antibody chains are expressed with signal sequences and are thus released to the culture media. However, if the anti-gelsolin antibody chains are not naturally secreted by host cells, the anti-gelsolin antibody chains can be released by treatment with mild detergent. Purification of recombinant polypeptides is well known in the art and include ammonium sulfate precipitation, affinity chromatography purification technique, column chromatography, ion exchange purification technique, gel electrophoresis and the like (see generally Scopes, Protein Purification (Springer-Verlag, N.Y., 1982).

Polynucleotides encoding gelsolin binding agents, e.g., the anti-gelsolin antibody coding sequences, can be incorporated in transgenes for introduction into the genome of a transgenic animal and subsequent expression in the milk of the transgenic animal. See, e.g., U.S. Pat. Nos. 5,741,957, 5,304,489, and 5,849,992. Suitable transgenes include coding sequences for light and/or heavy chains in operable linkage with a promoter and enhancer from a mammary gland specific gene, such as casein or β-lactoglobulin. For production of transgenic animals, transgenes can be microinjected into fertilized oocytes, or can be incorporated into the genome of embryonic stem cells, and the nuclei of such cells transferred into enucleated oocytes.

Single Chain Antibodies. In one embodiment, the binding agent of the invention is a single chain anti-gelsolin antibody. According to the invention, techniques can be adapted for the production of single-chain antibodies specific to a gelsolin polypeptide (see, e.g., U.S. Pat. No. 4,946,778). Examples of techniques which can be used to produce single-chain Fvs and antibodies of the invention include those described in U.S. Pat. Nos. 4,946,778 and 5,258,498; Huston et al., *Methods in Enzymology*, 203: 46-88, 1991; Shu, L. et al., *Proc. Natl. Acad. Sci. USA*, 90: 7995-7999, 1993; and Skerra et al., *Science* 240: 1038-1040, 1988.

Chimeric and Humanized Antibodies. In one embodiment, the binding agent of the invention is a chimeric anti-gelsolin antibody. In one embodiment, the binding agent of the invention is a humanized anti-gelsolin antibody. In one embodiment of the invention, the donor and acceptor antibodies are monoclonal antibodies from different species. For example, the acceptor antibody is a human antibody (to minimize its antigenicity in a human), in which case the resulting CDR-grafted antibody is termed a "humanized" antibody.

Recombinant anti-gelsolin antibodies, such as chimeric and humanized monoclonal antibodies, comprising both human and non-human portions, can be made using standard recombinant DNA techniques, and are within the scope of the invention. For some uses, including in vivo use of the binding agent of the invention in humans as well as use of these agents in vitro detection assays, it is preferable to use chimeric, humanized, or human anti-gelsolin antibodies. Such chimeric and humanized monoclonal antibodies can be produced by recombinant DNA techniques known in the art. Such useful methods include, e.g., but are not limited to, methods described in International Application No. PCT/US86/02269; U.S. Pat. No. 5,225,539; European Patent No. 184187, European Patent No. 171496; European Patent No. 173494; PCT International Publication No. WO 86/01533; U.S. Pat. Nos. 4,816,567; 5,225,539; European Patent No. 125023; Better, et al., 1988. *Science* 240: 1041-1043; Liu, et al., 1987. *Proc. Natl. Acad. Sci. USA* 84: 3439-3443; Liu, et al., 1987. *J. Immunol.* 139: 3521-3526; Sun, et al., 1987. *Proc. Natl. Acad. Sci. USA* 84: 214-218; Nishimura, et al., 1987. *Cancer Res.* 47: 999-1005; Wood, et al., 1985. *Nature* 314: 446-449; Shaw, et al., 1988. *J. Natl. Cancer Inst.* 80: 1553-1559); Morrison (1985) Science 229: 1202-1207; Oi, et al. (1986) *BioTechniques* 4: 214; Jones, et al., 1986. *Nature* 321: 552-525; Verhoeyan, et al., 1988. *Science* 239: 1534; Morrison, *Science* 229: 1202, 1985; Oi et al., *BioTechniques* 4: 214, 1986; Gillies et al., *J. Immunol. Methods,* 125: 191-202, 1989; U.S. Pat. No. 5,807,715; and Beidler, et al., 1988. *Jr. Immunol.* 141: 4053-4060. For example, antibodies can be humanized using a variety of techniques including CDR-grafting (EP 0 239 400; WO 91/09967; U.S. Pat. Nos. 5,530, 101; 5,585,089; 5,859,205; 6,248,516; EP460167), veneering or resurfacing (EP 0 592 106; EP 0 519 596; Padlan E. A., *Molecular Immunology,* 28: 489-498, 1991; Studnicka et al., *Protein Engineering* 7: 805-814, 1994; Roguska et al., *PNAS* 91: 969-973, 1994), and chain shuffling (U.S. Pat. No. 5,565, 332). In one embodiment, a cDNA encoding a murine anti-gelsolin monoclonal antibody is digested with a restriction enzyme selected specifically to remove the sequence encoding the Fc constant region, and the equivalent portion of a cDNA encoding a human Fc constant region is substituted (see Robinson et al., PCT/US86/02269; Akira et al., European Patent Application, 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 125,023; Better et al. (1988) Science 240: 1041-1043; Liu et al. (1987) Proc. Natl. Acad. Sci. USA 84: 3439-3443; Liu et al. (1987) J Immunol 139: 3521-3526; Sun et al. (1987) *Proc. Natl. Acad. Sci. USA* 84: 214-218; Nishimura et al. (1987) *Cancer Res* 47: 999-1005; Wood et al. (1985) *Nature* 314: 446-449; and Shaw et al. (1988) *J. Natl. Cancer Inst.* 80: 1553-1559); U.S. Pat. Nos. 6,180,370; 6,300,064; 6,696,248; 6,706,484; 6,828,422.

In one embodiment, the present invention allows the construction of humanized anti-gelsolin antibodies that are unlikely to induce a human anti-mouse antibody (hereinafter referred to as "HAMA") response, while still having an effective antibody effector function. As used herein, the terms "human" and "humanized", in relation to antibodies, relate to any antibody which is expected to elicit a therapeutically tolerable weak immunogenic response in a human subject. In one embodiment, the present invention provides for a humanized gelsolin antibodies, heavy and light chain immunoglobulins.

CDR Antibodies. In one embodiment, the binding agent of the invention is an anti-gelsolin CDR antibody. Generally the donor and acceptor antibodies used to generate the anti-gelsolin CDR antibody are monoclonal antibodies from different species; typically the acceptor antibody is a human antibody (to minimize its antigenicity in a human), in which case the resulting CDR-grafted antibody is termed a "humanized" antibody. The graft may be of a single CDR (or even a portion of a single CDR) within a single $V_H$ or $V_L$ of the acceptor antibody, or can be of multiple CDRs (or portions thereof) within one or both of the $V_H$ and $V_L$. Frequently all three CDRs in all variable domains of the acceptor antibody will be replaced with the corresponding donor CDRs, though one need replace only as many as necessary to permit adequate binding of the resulting CDR-grafted antibody to MetAp3. Methods for generating CDR-grafted and humanized antibodies are taught by Queen et al. U.S. Pat. Nos. 5,585,089, 5,693,761; 5,693,762; and Winter U.S. Pat. No. 5,225,539; and EP 0682040. Methods useful to prepare $V_H$ and $V_L$ polypeptides are taught by Winter et al., U.S. Pat. Nos. 4,816, 397; 6,291,158; 6,291,159; 6,291,161; 6,545,142; EP 0368684; EPO451216; EP0120694.

After selecting suitable framework region candidates from the same family and/or the same family member, either or both the heavy and light chain variable regions are produced by grafting the CDRs from the originating species into the hybrid framework regions. Assembly of hybrid antibodies or hybrid antibody fragments having hybrid variable chain regions with regard to either of the above aspects can be accomplished using conventional methods known to those skilled in the art. For example, DNA sequences encoding the hybrid variable domains described herein (i.e., frameworks based on the target species and CDRs from the originating species) can be produced by oligonucleotide synthesis and/or PCR. The nucleic acid encoding CDR regions can also be isolated from the originating species antibodies using suitable restriction enzymes and ligated into the target species framework by ligating with suitable ligation enzymes. Alternatively, the framework regions of the variable chains of the originating species antibody can be changed by site-directed mutagenesis.

Since the hybrids are constructed from choices among multiple candidates corresponding to each framework region, there exist many combinations of sequences which are amenable to construction in accordance with the principles described herein. Accordingly, libraries of hybrids can be assembled having members with different combinations of individual framework regions. Such libraries can be electronic database collections of sequences or physical collections of hybrids.

This process typically does not alter the acceptor antibody's FRs flanking the grafted CDRs. However, one skilled in the art can sometimes improve antigen binding affinity of the resulting anti-gelsolin CDR grafted antibody by replacing certain residues of a given FR to make the FR more similar to the corresponding FR of the donor antibody. Preferred locations of the substitutions include amino acid residues adjacent to the CDR, or which are capable of interacting with a CDR (see, e.g., U.S. Pat. No. 5,585,089, especially columns 12-16). Or one skilled in the art can start with the donor FR and modify it to be more similar to the acceptor FR or a human consensus FR. Techniques for making these modifications are known in the art. Particularly if the resulting FR fits a human consensus FR for that position, or is at least 90% or more identical to such a consensus FR, doing so may not increase the antigenicity of the resulting modified anti-gelsolin CDR antibody significantly compared to the same antibody with a fully human FR.

Fusion Proteins. In one embodiment, the binding agent of the invention is a fusion protein. The gelsolin binding agents of the present invention, when fused to a second protein, can be used as an antigenic tag. Examples of domains that can be fused to polypeptides include not only heterologous signal sequences, but also other heterologous functional regions. The fusion does not necessarily need to be direct, but can occur through linker sequences. Moreover, fusion proteins of the present invention can also be engineered to improve characteristics of the gelsolin binding agent. For instance, a region of additional amino acids, particularly charged amino acids, can be added to the N-terminus of the gelsolin binding agent to improve stability and persistence during purification from the host cell or subsequent handling and storage. Also, peptide moieties can be added to the gelsolin binding agent to facilitate purification. Such regions can be removed prior to final preparation of the gelsolin binding agent. The addition of peptide moieties to facilitate handling of polypeptides are familiar and routine techniques in the art. The gelsolin binding agent of the invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., *Cell* 37: 767, 1984.

Thus, any of these above fusions can be engineered using the polynucleotides or the polypeptides of the present invention. Also, the fusion protein can show an increased half-life in vivo.

Fusion proteins having disulfide-linked dimeric structures (due to the IgG) can be more efficient in binding and neutralizing other molecules, than the monomeric secreted protein or protein fragment alone. Fountoulakis et al., *J. Biochem.* 270: 3958-3964, 1995.

Similarly, EP-A-0 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, e.g., improved pharmacokinetic properties. See EP-A 0232 262. Alternatively, deleting the Fc part after the fusion protein has been expressed, detected, and purified, would be desired. For example, the Fc portion can hinder therapy and diagnosis if the fusion protein is used as an antigen for immunizations. In drug discovery, e.g., human proteins, such as hIL-5, have been fused with Fc portions for the purpose of high-throughput screening assays to identify antagonists of hIL-5. Bennett et al., *J. Molecular Recognition* 8: 52-58, 1995; Johanson et al., *J. Biol. Chem.*, 270: 9459-9471, 1995.

Labeled Gelsolin-Binding Agent. In one embodiment, the gelsolin binding agent of the present invention is coupled with a label moiety, i.e., detectable group. The particular label or detectable group conjugated to the gelsolin binding agent of the invention is not a critical aspect of the invention, so long as it does not significantly interfere with the specific binding of the gelsolin binding agent of the present invention to the gelsolin polypeptide or the gelsolin-like polypeptide. The detectable group can be any material having a detectable physical or chemical property. Such detectable labels have been well-developed in the field of immunoassays and imaging, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^3$H, $^{14}$C, $^{35}$S, $^{125}$I, $^{121}$I, $^{131}$I, $^{112}$In, $^{99}$mTc), other imaging agents such as microbubbles for ultrasound imaging), $^{18}$F, $^{11}$C, $^{15}$O, (for Positron emission tomography), $^{99m}$TC, $^{111}$In (for Single photon emission tomography), enzymes (e.g., horse radish peroxidase, alkaline phosphatase and others commonly used in an ELISA), and calorimetric labels such as colloidal gold or colored glass or plastic (e.g., polystyrene, polypropylene, latex, and the like) beads. Patents that described the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also Handbook of Fluorescent Probes and Research Chemicals (6$^{th}$ Ed., Molecular Probes, Inc., Eugene Oreg.).

The label can be coupled directly or indirectly to the desired component of an assay according to methods well known in the art. As indicated above, a wide variety of labels can be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, e.g., biotin, thyroxine, and cortisol, it can be used in conjunction with the labeled, naturally-occurring anti-ligands. Alternatively, any haptenic or antigenic compound can be used in combination with an antibody, e.g., an anti-gelsolin antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds useful as labelling moieties, include, but are not limited to, e.g., fluorescein and its derivatives, rhodamine and its derivatives, dansyl, umbelliferone, and the like. Chemiluminescent compounds useful as labelling moieties, include, but are not limited to, e.g., luciferin, and 2,3-dihydrophthalazinediones, e.g., luminol. For a review of various labeling or signal-producing systems which can be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally simple colorimetric labels can be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies, e.g., the anti-gelsolin antibodies. In this case, antigen-coated particles are agglutinated by samples comprising the target antibodies. In this format, none of the components need be labeled and the presence of the target antibody is detected by simple visual inspection.

Identifying and Characterizing the Gelsolin-Binding Agents of the Invention

Methods for identifying and/or screening the binding agents of the invention. Methods useful to identify and screen the binding agents, e.g., anti-gelsolin antibodies and anti-gelsolin antibody-related polypeptides, that possess the desired specificity to the gelsolin polypeptide include any immunologically-mediated techniques known within the art. Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity; (2) helper T lymphocytes can be incubated with antigens and antigen presenting cells and the synthesis and secretion of cytokines measured by standard methods (Windhagen A; et al., *Immunity*, 2: 373-80, 1995); (3) antigen presenting cells can be incubated with whole protein antigen and the presentation of that antigen on MHC detected by either T lymphocyte activation assays or biophysical methods (Harding et al., *Proc. Natl. Acad. Sci.*, 86: 4230-4, 1989); (4) mast cells can be incubated with reagents that cross-link their Fc-epsilon receptors and histamine release measured by enzyme immunoassay (Siraganian et al., *TIPS*, 4: 432-437, 1983); and (5) enzyme-linked immunosorbent assay (ELISA).

Similarly, products of an immune response in either a model organism (e.g., mouse) or a human subject can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., *Blood,* 72: 1310-5, 1988); (3) the proliferation of peripheral blood mononuclear cells in response to mitogens or mixed lymphocyte reaction can be measured using $^3$H-thymidine; (4) the phagocytic capacity of granulocytes, macrophages, and other phagocytes in PBMCs can be measured by placing PMBCs in wells together with labeled particles (Peters et al., *Blood,* 72: 1310-5, 1988); and (5) the differentiation of immune system cells can be measured by labeling PBMCs with antibodies to CD molecules such as CD4 and CD8 and measuring the fraction of the PBMCs expressing these markers.

In one embodiment, gelsolin binding agents of the invention are selected using display of candidate binding agents on the surface of replicable genetic packages. See, e.g., U.S. Pat. Nos. 5,514,548; 5,837,500; 5,871,907; 5,885,793; 5,969,108; 6,225,447; 6,291,650; 6,492,160; EP 585 287; EP 605522; EP 616640; EP 1024191; EP 589 877; EP 774 511; EP 844 306. Methods useful for producing/selecting a filamentous bacteriophage particle containing a phagemid genome encoding for a binding molecule with a desired specificity has been described. See, e.g., EP 774 511; U.S. Pat. Nos. 5,871,907; 5,969,108; 6,225,447; 6,291,650; 6,492,160.

In one embodiment, gelsolin binding agents of the invention are selected using display of candidate binding agents on the surface of a yeast host cell. Methods useful for the isolation of scFv polypeptides by yeast surface display have been described by Kieke et al., *Protein Eng.* 1997 November; 10(11): 1303-10.

In one embodiment, gelsolin binding agents of the invention are selected using ribosome display. Methods useful for identifying ligands in peptide libraries using ribosome display have been described by Mattheakis et al., *Proc: Natl. Acad. Sci. USA* 91: 9022-26, 1994; and Hanes et al., *Proc. Natl. Acad. Sci. USA* 94: 4937-42, 1997.

In one embodiment, gelsolin binding agents of the invention are selected using tRNA display of candidate binding agents. Methods useful for in vitro selection of ligands using tRNA display have been described by Merryman et al., *Chem. Biol.*, 9: 741-46, 2002.

In one embodiment, gelsolin binding agents of the invention are selected using RNA display. Methods useful for selecting peptides and proteins using RNA display libraries have been described by Roberts et al. *Proc. Natl. Acad. Sci. USA*, 94: 12297-302, 1997; and Nemoto et al., *FEBS Lett.,* 414: 405-8, 1997. Methods useful for selecting peptides and proteins using unnatural RNA display libraries have been described by Frankel et al., *Curr. Opin. Struct. Biol.,* 13: 506-12, 2003.

In one embodiment, gelsolin binding agents of the invention are expressed in the periplasm of gram negative bacteria and mixed with labeled gelsolin polypeptide. See WO 02/34886. In clones expressing recombinant polypeptides with affinity for the gelsolin polypeptide, the concentration of the labeled gelsolin polypeptide bound to the binding agents is increased and allows the cells to be isolated from the rest of the library as described in Harvey et al., *Proc. Natl. Acad. Sci.* 22: 9193-98 2004 and U.S. Pat. Publication No. 2004/0058403.

After selection of the desired gelsolin binding agent, it is contemplated that it can be produced in large volume by any technique known to those skilled in the art, e.g., prokaryotic or eukaryotic cell expression and the like. The gelsolin binding agents which are, e.g., but not limited to, anti-gelsolin hybrid antibodies or fragments can be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which can be manipulated as described herein, thereby producing a vector for the expression of a hybrid antibody heavy chain.

Measurement of Gelsolin Binding. In one embodiment, a gelsolin binding assay refers to an assay format wherein a gelsolin polypeptide and a gelsolin binding agent are mixed under conditions suitable for binding between the gelsolin or gelsolin-like polypeptide and the gelsolin binding agent and assessing the amount of binding between the gelsolin or gelsolin-like polypeptide and the gelsolin binding agent. The amount of binding is compared with a suitable control, which can be the amount of binding in the absence of the gelsolin polypeptide, the amount of the binding in the presence of non-specific immunoglobulin composition, or both. The amount of binding can be assessed by any suitable method. Binding assay methods include, e.g., ELISA, radioimmunoassays, scintillation proximity assays, fluorescence energy transfer assays, liquid chromatography, membrane filtration assays, and the like. Biophysical assays for the direct measurement of gelsolin polypeptide binding to gelsolin binding agents are, e.g., nuclear magnetic resonance, fluorescence, fluorescence polarization, surface plasmon resonance (BIA-COR chips) and the like. Specific binding is determined by standard assays known in the art, e.g., radioligand binding assays, ELISA, FRET, immunoprecipitation, SPR, NMR (2D-NMR), mass spectroscopy and the like. If the specific binding of a candidate gelsolin binding agent is at least 1 percent greater than the binding observed in the absence of the candidate gelsolin binding agent, the candidate gelsolin binding agent is useful as a gelsolin binding agent of the invention.

Co-crystals of the gelsolin polypeptides and the gelsolin binding agents are also provided by the present invention as a method of determining molecular interactions. Conditions suitable for binding between the gelsolin binding agent and a gelsolin polypeptide will depend on the compound and its ligand and can be readily determined by one of ordinary skill in the art.

Uses of the Gelsolin-Binding Agents of the Invention

General. The binding agents of the invention are useful in methods known in the art relating to the localization and/or quantitation of a gelsolin polypeptide (e.g., for use in measuring levels of the gelsolin polypeptide within appropriate physiological samples, for use in diagnostic methods, for use in imaging the polypeptide, and the like). Binding agents of the invention are useful to isolate a gelsolin polypeptide by standard techniques, such as affinity chromatography or immunoprecipitation. A gelsolin binding agent of the invention can facilitate the purification of natural immunoreactive gelsolin polypeptides or gelsolin-like polypeptides from biological samples, e.g., mammalian sera or cells as well as recombinantly-produced immunoreactive gelsolin polypeptides or gelsolin-like polypeptides expressed in a host system. Moreover, gelsolin binding agent can be used to detect an immunoreactive gelsolin polypeptide or a gelsolin-like polypeptide (e.g., in plasma, a cellular lysate or cell supernatant) in order to evaluate the abundance and pattern of expression of the immunoreactive polypeptide. The gelsolin binding agents of the invention can be used diagnostically to monitor immunoreactive gelsolin and/or gelsolin-like polypeptide levels in tissue as part of a clinical testing procedure, e.g., to determine the efficacy of a given treatment regimen. As noted above, the detection can be facilitated by coupling (i.e., physically linking) the gelsolin binding agent of the invention to a detectable substance.

Detection of Gelsolin Polypeptide. An exemplary method for detecting the presence or absence of a gelsolin polypeptide or a gelsolin-like polypeptide in a biological sample involves obtaining a biological sample from a test subject and contacting the biological sample with a gelsolin binding agent of the invention capable of detecting a gelsolin polypeptide or a gelsolin-like polypeptide such that the presence of a gelsolin polypeptide or a gelsolin-like polypeptide is detected in the biological sample. An example of a gelsolin binding agent is an antibody raised against SEQ ID NO.: 1 or a homlog or fragment thereof, capable of binding to a gelsolin polypeptide or a gelsolin-like polypeptide, preferably an antibody with a detectable label. The term "labeled", with regard to the binding agent, is intended to encompass direct labeling of the binding agent by coupling (i.e., physically linking) a detectable substance to the binding agent, as well as indirect labeling of the binding agent by reactivity with another compound that is directly labeled. Examples of indirect labeling include detection of a primary antibody using a fluorescently-labeled secondary antibody and end-labeling of a DNA probe with biotin such that it can be detected with fluorescently-labeled streptavidin.

The detection method of the invention can be used to detect a gelsolin polypeptide or a gelsolin-like polypeptide in a biological sample in vitro as well as in vivo. In vitro techniques for detection of a gelsolin polypeptide or a gelsolin-like polypeptide include enzyme linked immunosorbent assays (ELISAs), Western blots, immunoprecipitations, radioimmunoassay, and immunofluorescence. Furthermore, in vivo techniques for detection of a gelsolin polypeptide or a gelsolin-like polypeptide include introducing into a subject a labeled gelsolin binding agent, e.g., an anti-gelsolin antibody. For example, the antibody can be labeled with a radioactive marker whose presence and location in a subject can be detected by standard imaging techniques. In one embodiment, the biological sample contains polypeptide molecules from the test subject.

Immunoassay and Imaging. A gelsolin binding agent of the present invention can be used to assay gelsolin polypeptide levels or gelsolin-like polypeptide levels in a biological sample (e.g. human plasma) using antibody-based techniques. For example, protein expression in tissues can be studied with classical immunohistological methods. Jalkanen, M. et al., *J. Cell. Biol.* 101: 976-985, 1985; Jalkanen, M. et al., *J. Cell. Biol.* 105: 3087-3096, 1987. Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes or other radioactive agent, such as iodine ($^{125}$I, $^{121}$I, $^{131}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying secreted gelsolin polypeptide levels or gelsolin-like polypeptide levels in a biological sample, secreted gelsolin polypeptide levels or gelsolin-like polypeptide levels can also be detected in vivo by imaging. A gelsolin binding agent, e.g., an anti-gelsolin antibody labels or markers for in vivo imaging of the gelsolin polypeptide levels or the gelsolin-like polypeptide include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the gelsolin binding agent by labeling of nutrients for the relevant scFv clone.

A gelsolin binding agent which has been labeled with an appropriate detectable imaging moiety, such as a radioisotope (e.g., $^{131}$I, $^{112}$In, $^{99m}$Tc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled gelsolin binding agent will then preferentially accumulate at the location of cells which contain the specific target polypeptide. For example, in vivo tumor imaging is described in S. W. Burchiel et al., *Tumor Imaging: The Radiochemical Detection of Cancer* 13 (1982).

Thus, the invention provides a diagnostic method of a medical condition, which involves: (a) assaying the expression of a polypeptide by measuring binding of a gelsolin binding agent of the present invention in cells or body fluid of an individual; (b) comparing the amount of protein with a standard, whereby an increase or decrease in the assayed polypeptide compared to the standard level is indicative of a medical condition.

Affinity Purification. The gelsolin binding agents of the present invention may be used to purify immunoreacitve gelsolin (e.g., native plasma gelsolin) from a sample. In some embodiments, antibodies (e.g. GN3E9, GC1C10, and/or GF2D6) may be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., *Meth. Enzym.* 34 Academic Press, N.Y. (1974)).

The simplest method to bind the antigen to the antibody-support matrix is to collect the beads in a column and pass the antigen solution down the column. The efficiency of this method depends on the contact time between the immobilized antibody and the antigen, which can be extended by using low flow rates. The immobilized antibody captures the antigen as it flows past. Alternatively, an antigen can be contacted with the antibody-support matrix by mixing the antigen solution with the support (e.g. beads) and rotating or rocking the slurry, allowing maximum contact between the antigen and the immobilized antibody. After the binding reaction has been completed, the slurry is passed into a column for collection of the beads. The beads are washed using a suitable washing buffer and then the pure or substantially pure antigen is eluted.

An antibody or polypeptide of interest can be conjugated to a solid support, such as a bead. In addition, a first solid support such as a bead can also be conjugated, if desired, to a second solid support, which can be a second bead or other support, by any suitable means, including those disclosed herein for conjugation of a polypeptide to a support. Accordingly, any of the conjugation methods and means disclosed herein with reference to conjugation of a polypeptide to a solid support can also be applied for conjugation of a first support to a second support, where the first and second solid support can be the same or different.

Appropriate linkers, which can be cross-linking agents, for use for conjugating a polypeptide to a solid support include a variety of agents that can react with a functional group present on a surface of the support, or with the polypeptide, or both. Reagents useful as cross-linking agents include homo-bi-functional and, in particular, hetero-bi-functional reagents. Useful bi-functional cross-linking agents include, but are not limited to, N-SIAB, dimaleimide, DTNB, N-SATA, N-SPDP, SMCC and 6-HYNIC. A cross-linking agent can be selected to provide a selectively cleavable bond between a polypeptide and the solid support. For example, a photolabile cross-linker, such as 3-amino-(2-nitrophenyl)propionic acid can be employed as a means for cleaving a polypeptide from a solid support. (Brown et al., *Mol. Divers*, pp, 4-12 (1995); Rothschild et al., *Nucl. Acids Res.*, 24:351-66 (1996); and U.S. Pat. No. 5,643,722). Other cross-linking reagents are well-known in the art. (See, e.g., Wong (1991), supra; and Hermanson (1996), supra).

An antibody or polypeptide can be immobilized on a solid support, such as a bead, through a covalent amide bond formed between a carboxyl group functionalized bead and the amino terminus of the polypeptide or, conversely, through a covalent amide bond formed between an amino group functionalized bead and the carboxyl terminus of the polypeptide. In addition, a bi-functional trityl linker can be attached to the support, e.g, to the 4-nitrophenyl active ester on a resin, such as a Wang resin, through an amino group or a carboxyl group on the resin via an amino resin. Using a bi-functional trityl approach, the solid support can require treatment with a volatile acid, such as formic acid or trifluoracetic acid to ensure that the polypeptide is cleaved and can be removed. In such a case, the polypeptide can be deposited as a beadless patch at the bottom of a well of a solid support or on the flat surface of a solid support. After addition of a matrix solution, the polypeptide can be desorbed into a MS.

Hydrophobic trityl linkers can also be exploited as acid-labile linkers by using a volatile acid or an appropriate matrix solution, e.g., a matrix solution containing 3-HPA, to cleave an amino linked trityl group from the polypeptide. Acid lability can also be changed. For example, trityl, monomethoxytrityl, dimethoxytrityl or trimethoxytrityl can be changed to the appropriate p-substituted, or more acid-labile tritylamine derivatives, of the polypeptide, i.e., trityl ether and tritylamine bonds can be made to the polypeptide. Accordingly, a polypeptide can be removed from a hydrophobic linker, e.g., by disrupting the hydrophobic attraction or by cleaving tritylether or tritylamine bonds under acidic conditions, including, if desired, under typical MS conditions, where a matrix, such as 3-HPA acts as an acid.

Orthogonally cleavable linkers can also be useful for binding a first solid support, e.g., a bead to a second solid support, or for binding a polypeptide of interest to a solid support. Using such linkers, a first solid support, e.g., a bead, can be selectively cleaved from a second solid support, without cleaving the polypeptide from the support; the polypeptide then can be cleaved from the bead at a later time. For example, a disulfide linker, which can be cleaved using a reducing agent, such as DTT, can be employed to bind a bead to a second solid support, and an acid cleavable bi-functional trityl group could be used to immobilize a polypeptide to the support. As desired, the linkage of the polypeptide to the solid support can be cleaved first, e.g., leaving the linkage between the first and second support intact. Trityl linkers can provide a covalent or hydrophobic conjugation and, regardless of the nature of the conjugation, the trityl group is readily cleaved in acidic conditions.

For example, a bead can be bound to a second support through a linking group which can be selected to have a length and a chemical nature such that high density binding of the beads to the solid support, or high density binding of the polypeptides to the beads, is promoted. Such a linking group can have, e.g., "tree-like" structure, thereby providing a multiplicity of functional groups per attachment site on a solid support. Examples of such linking group; include polylysine, polyglutamic acid, penta-erythrole and tris-hydroxy-aminomethane.

Noncovalent Binding Association. An antibody or polypeptide can be conjugated to a solid support, or a first solid support can also be conjugated to a second solid support, through a noncovalent interaction. For example, a magnetic bead made of a ferromagnetic material, which is capable of being magnetized, can be attracted to a magnetic solid support, and can be released from the support by removal of the magnetic field. Alternatively, the solid support can be provided with an ionic or hydrophobic moiety, which can allow the interaction of an ionic or hydrophobic moiety, respectively, with a polypeptide, e.g., a polypeptide containing an attached trityl group or with a second solid support having hydrophobic character.

A solid support can also be provided with a member of a specific binding pair and, therefore, can be conjugated to a polypeptide or a second solid support containing a complementary binding moiety. For example, a bead coated with avidin or with streptavidin can be bound to a polypeptide having a biotin moiety incorporated therein, or to a second solid support coated with biotin or derivative of biotin, such as imino-biotin.

It should be recognized that any of the binding members disclosed herein or otherwise known in the art can be reversed. Thus, biotin, e.g., can be incorporated into either a polypeptide or a solid support and, conversely, avidin or other biotin binding moiety would be incorporated into the support or the polypeptide, respectively. Other specific binding pairs contemplated for use herein include, but are not limited to, hormones and their receptors, enzyme, and their substrates, a nucleotide sequence and its complementary sequence, an antibody and the antigen to which it interacts specifically, and other such pairs knows to those skilled in the art.

Diagnostic Uses of Gelsolin Binding Agents

General. The gelsolin binding compositions of the invention are useful in diagnostic methods. As such, the present invention provides methods using the binding agents of the invention useful in the diagnosis of gelsolin-related medical conditions in a subject. Binding agents of the invention may be selected such that they have any level of epitope binding specificity and very high binding affinity to the gelsolin polypeptide. In general, the higher the binding affinity of an binding agent the more stringent wash conditions can be performed in an immunoassay to remove nonspecifically bound material without removing target polypeptide. Accordingly, gelsolin binding agents of the invention useful in diagnostic assays usually have binding affinities of at least $10^8$, $10^9$, $10^{10}$, $10^{11}$, or $10^{12} M^{-1}$. Further, it is desirable that gelsolin binding agents used as diagnostic reagents have a sufficient kinetic on-rate to reach equilibrium under standard conditions in at least 12 h, preferably at least five (5) h and more preferably at least one (1) hour.

Some methods of the invention employ polyclonal preparations of anti-gelsolin antibodies and anti-gelsolin antibody compositions of the invention as diagnostic reagents, and other methods employ monoclonal isolates. The use of polyclonal mixtures has a number of advantages compared to compositions made of one monoclonal anti-gelsolin antibody. By binding to multiple sites on a gelsolin polypeptide, polyclonal anti-gelsolin antibodies or other polypeptides, one can generate a stronger signal (for diagnostics) than a monoclonal that binds to a single site on the gelsolin polypeptide or the gelsolin-like polypeptide. Further, a polyclonal preparation can bind to numerous variants of a prototypical target sequence (e.g., allelic variants, species variants, strain variants, drug-induced escape variants) whereas a monoclonal antibody can bind only to the prototypical sequence or a narrower range of variants thereto. However, monoclonal anti-gelsolin antibodies are advantageous for detecting a single antigen in the presence or potential presence of closely related antigens.

In methods employing polyclonal human anti-gelsolin antibodies prepared in accordance with the methods described above, the preparation typically contains an assortment of gelsolin binding agents, e.g., antibodies, with different epitope specificities to the target polypeptide. In some methods employing monoclonal antibodies, it is desirable to have two antibodies of different epitope binding specificities. A difference in epitope binding specificities can be determined by a competition binding assay.

Although gelsolin binding agents which are human antibodies can be used as diagnostic reagents for any kind of sample, they are most useful as diagnostic reagents for human biological samples. Gelsolin binding agents can be used to detect a given gelsolin or gelsolin-like polypeptide in a variety of standard assay formats. Such formats include immunoprecipitation, Western blotting, ELISA, radioimmunoassay, and immunometric assays. See Harlow & Lane, *Antibodies, A Laboratory Manual* (Cold Spring Harbor Publications, New York, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Biological samples can be obtained from any tissue or body fluid of a subject.

Immunometric or sandwich assays are a preferred format for the diagnostic methods of the present invention. See U.S. Pat. Nos. 4,376,110, 4,486,530, 5,914,241, and 5,965,375. Such assays use one gelsolin binding agent, e.g., an anti-gelsolin antibody or a population of anti-gelsolin antibodies immobilized to a solid phase, and another anti-gelsolin antibody or a population of anti-gelsolin antibodies in solution. Typically, the solution anti-gelsolin antibody or population of anti-gelsolin antibodies is labeled. If an antibody population is used, the population can contain antibodies binding to different epitope specificities within the target polypeptide. Accordingly, the same population can be used for both solid phase and solution antibody. If anti-gelsolin monoclonal antibodies are used, first and second gelsolin monoclonal antibodies having different binding specificities are used for the solid and solution phase. Solid phase (also referred to as "capture") and solution (also referred to as "detection") antibodies can be contacted with target antigen in either order or simultaneously. If the solid phase antibody is contacted first, the assay is referred to as being a forward assay. Conversely, if the solution antibody is contacted first, the assay is referred to as being a reverse assay. If the target is contacted with both antibodies simultaneously, the assay is referred to as a simultaneous assay. After contacting the gelsolin polypeptide with the anti-gelsolin antibody, a sample is incubated for a period that usually varies from about 10 min to about 24 hr and is usually about 1 hr. A wash step is then performed to remove components of the sample not specifically bound to the anti-gelsolin antibody being used as a diagnostic reagent. When solid phase and solution antibodies are bound in separate steps, a wash can be performed after either or both binding steps. After washing, binding is quantified, typically by detecting a label linked to the solid phase through binding of labeled solution antibody. Usually for a given pair of antibodies or populations of antibodies and given reaction conditions, a calibration curve is prepared from samples containing known concentrations of target antigen. Concentrations of the gelsolin polypeptide in samples being tested are then read by interpolation from the calibration curve. Analyte can be measured either from the amount of labeled solution antibody bound at equilibrium or by kinetic measurements of bound labeled solution antibody at a series of time points before equilibrium is reached. The slope of such a curve is a measure of the concentration of the gelsolin polypeptide in a sample Suitable supports for use in the above methods include, e.g., nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™ (Amersham Pharmacia Biotech, Piscataway N.J.), and the like. Immobilization can be by absorption or by covalent attachment. Optionally, anti-gelsolin antibodies can be joined to a linker molecule, such as biotin for attachment to a surface bound linker, such as avidin.

The invention also provides for prognostic (or predictive) assays for determining whether an individual is at risk of developing a disorder associated with gelsolin polypeptide expression or activity. Such assays can be used for prognostic or predictive purpose to thereby prophylactically treat an individual prior to the onset of a disorder characterized by or associated with a gelsolin polypeptide. Furthermore, the methods of the present invention can also be used to assess whether an individual expresses a gelsolin polypeptide or a polymorphic form of the gelsolin polypeptide in instances where a gelsolin binding agent of the present invention has greater affinity for the gelsolin polypeptide for its polymorphic form (or vice versa).

The levels of certain polypeptides in a particular tissue (or in the blood) of a subject may be indicative of the toxicity, efficacy, rate of clearance or rate of metabolism of a given drug when administered to the subject. The methods described herein can also be used to determine the levels of such polypeptide(s) (e.g. gelsolin or gelsolin-like polypeptides) in subjects to aid in predicting the response of such subjects to these drugs. Another aspect of the invention provides methods for determining gelsolin or gelsolin-like polypeptide expression in an individual to thereby select appropriate therapeutic or prophylactic compounds for that individual.

The binding of a gelsolin binding agent of the invention to a gelsolin polypeptide or a gelsolin-like polypeptide, e.g., can be utilized to identify a subject having or at risk of developing a disorder associated with the gelsolin polypeptide or gelsolin-like polypeptide expression or activity. Alternatively, the prognostic assays can be utilized to identify a subject having or at risk for developing the disease or disorder. Thus, the invention provides a method for identifying a disease or condition associated with an aberrant gelsolin polypeptide or gelsolin-like polypeptide expression or activity in which a test sample is obtained from a subject and the gelsolin or gelsolin-like polypeptide detected, wherein the presence of an alteration of gelsolin or gelsolin-like polypeptide is diagnostic for a subject having or at risk of developing a disease or condition associated with an aberrant gelsolin polypeptide or gelsolin-like polypeptide expression or activity.

Furthermore, the prognostic assays described herein can be used to determine whether a subject can be administered a compound (e.g., an agonist, antagonist, peptidomimetic, polypeptide, peptide, nucleic acid, small molecule, or other drug candidate) to treat a disease or disorder associated with an aberrant gelsolin polypeptide or gelsolin-like polypeptide expression or activity. For example, such methods can be used to determine whether a subject can be effectively treated with a compound affecting gelsolin polypeptide levels (e.g., a chemotherapeutic agent). Thus, the invention provides methods for determining whether a subject can be effectively treated with a compound for a disorder or condition associated with an aberrant gelsolin polypeptide or gelsolin-like polypeptide expression or activity in which a test sample is obtained and the gelsolin polypeptide or the gelsolin-like polypeptide is detected using the gelsolin binding agent (e.g., wherein the presence or absence of the gelsolin polypeptide or the gelsolin-like polypeptide is diagnostic for a subject that can be administered the compound to treat a disorder associated with an aberrant gelsolin polypeptide or gelsolin-like polypeptide expression or activity).

The level of the gelsolin polypeptide or the gelsolin-like polypeptide in a blood or tissue sample obtained from a subject is determined and compared with the level found in a blood sample or a sample from the same tissue type obtained from an individual who is free of the disease. An underabundance (or overabundance) of the gelsolin polypeptide or gelsolin-like polypeptide in the sample obtained from the subject suspected of having the disease or condition affecting gelsolin levels compared with the sample obtained from the healthy subject is indicative of the gelsolin polypeptide or gelsolin-like polypeptide-associated disease or condition in the subject being tested. Further testing may be required to make a positive diagnosis.

There are a number of diseases in which the degree of underabundance (or overabundance) of certain gelsolin polypeptide or gelsolin-like polypeptide molecules known to be indicative of whether a subject with the disease is likely to respond to a particular type of therapy or treatment. Thus, the method of detecting a gelsolin polypeptide or gelsolin-like polypeptide in a sample can be used as a method of prognosis, e.g., to evaluate the likelihood that the subject will respond to the therapy or treatment. The level of the relevant prognostic polypeptide in a suitable tissue or blood sample from the subject is determined and compared with a suitable control, e.g., the level in subjects with the same disease but who have responded favorably to the treatment. The degree to which the prognostic polypeptide is underexpressed in the sample compared with the control may be predictive of likelihood that the subject will not respond favorably to the treatment or therapy, e.g. tolerate chemotherapy treatment. The greater the overexpression (or underexpression) relative to the control, the less likely the subject will respond to the treatment. Examples of conditions in which plasma gelsolin levels are decreased compared to control subjects include, but are not limited to, septic shock, multiple organ dysfunction syndrome, rheumatoid arthritis, trauma, stroke, heart infarction, cancer, chemotherapy and radiation therapy, systemic autoimmune disease, and chronic hepatitis.

The methods described herein can be performed, e.g., by utilizing pre-packaged diagnostic kits comprising at least one probe reagent, e.g., gelsolin binding agent described herein, which can be conveniently used, e.g., in clinical settings to diagnose subjects exhibiting symptoms or family history of a disease or illness involving a gelsolin polypeptide or gelsolin-like polypeptide. Furthermore, any cell type or tissue in which gelsolin polypeptide or gelsolin-like polypeptide is expressed can be utilized in the prognostic assays described herein.

Correlating a Subject to a Standard Reference Population. To deduce a correlation between clinical response to a treatment and a particular level of plasma gelsolin, it is necessary to obtain data on the clinical responses exhibited by a population of individuals who received the treatment, i.e., a clinical population. This clinical data maybe obtained by retrospective analysis of the results of a clinical trial(s). Alternatively, the clinical data may be obtained by designing and carrying out one or more new clinical trials. The analysis of clinical population data is useful to define a standard reference population(s) which, in turn, are useful to classify subjects for clinical trial enrollment or for selection of therapeutic treatment. In a preferred embodiment, the subjects included in the clinical population have been graded for the existence of the medical condition of interest. Grading of potential subjects can include, e.g., a standard physical exam or one or more lab tests. Alternatively, grading of subjects can include use of a gene expression pattern. For example, plasma gelsolin level is a useful as grading criteria where there is a strong correlation between expression pattern and susceptibility or severity to a disease or condition. In one embodiment, a subject is classified or assigned to a particular group or class based on similarity between the measured levels of a one or more biomarkers in the subject and the level of the one or more biomarkers observed in a standard reference population.

In one embodiment of the invention, a therapeutic treatment of interest is administered to each subject in a trial population, and each subject's response to the treatment is measured using one or more predetermined criteria. It is contemplated that in many cases, the trial population will exhibit a range of responses, and that the investigator will choose the number of responder groups (e.g., low, medium, high) made up by the various responses. In addition, the expression level of a biomarker (e.g. plasma gelsolin) is quantified, which may be done before and/or after administering the treatment. These results are then analyzed to determine if any observed variation in clinical response between groups is statistically significant. Statistical analysis methods, which may be used, are described in L.D. Fisher & G. vanBelle, *Biostatistics: A Methodology for the Health Sciences* (Wiley-Interscience, New York, 1993).

The skilled artisan can construct a mathematical model that predicts clinical response as a function of expression level from the analyses described above. The identification of an association between a clinical response and an expression level for the biomarker may be the basis for designing a diagnostic method to determine those individuals who will or will not respond to the treatment, or alternatively, will respond at a lower level and thus may require more treatment, i.e., a greater dose of a drug. The diagnostic method may take one of several forms: for example, a ELISA or antibody-based test, a serological test, or a physical exam measurement. The only requirement is that there be a good correlation between the diagnostic test results and the underlying condition. In a preferred embodiment, this diagnostic method uses an antibody assay for serum gelsolin described above.

Predictive Medicine. The invention also pertains to the field of predictive medicine in which diagnostic assays, prognostic assays, and monitoring clinical trials are used for prognostic (predictive) purposes to treat prophylactically a subject. Accordingly, one aspect of the invention relates to diagnostic assays for determining plasma gelsolin levels in the context of a biological sample (e.g., blood, serum, cells, tissue) to thereby determine whether an individual is afflicted with a disease or disorder, or is at risk of developing a disorder, associated with aberrant plasma gelsolin level.

Prognostic Assays. The binding of a prognostic compound to a biomarker molecule, e.g., biomarker polypeptide or nucleic acid encoding a biomarker polypeptide, can be utilized to identify a subject having or at risk of developing a disorder associated with biomarker polypeptide expression or activity (which are described above). A prognostic compound is any compound which binds to or associates with a biomarker molecule, including, but not limited to, e.g., anti-biomarker polypeptide antibody, small molecule, nucleic acid, polypeptide, oligosaccharide, lipid, or combination thereof. Alternatively, the prognostic assays can be utilized to identify a subject having or at risk for developing the disease or disorder. Thus, the invention provides a method for identifying a disease or disorder associated with biomarker expression or activity in which a test sample is obtained from a subject and prognostic compound binding or activity is detected, wherein the presence of an alteration of prognostic compound binding or activity is diagnostic for a subject having, or at risk of developing, a disease or disorder associated with biomarker expression or activity. As used herein, a "test sample" refers to a biological sample obtained from a subject of interest. For example, a test sample can be a biological fluid (e.g., serum), cell sample, or tissue, or isolated nucleic acid or polypeptide derived therefrom.

Furthermore, the prognostic assays described herein can be used to determine whether a subject can be administered a compound (e.g., an agonist, antagonist, peptidomimetic, polypeptide, peptide, nucleic acid, small molecule, or other drug candidate) to treat a biomarker-associated disease or disorder. As used herein, the administration of a compound to a subject or patient includes self-administration and the administration by another. In one embodiment, the prognostic assays described herein are used to determine if a subject will be responsive to a compound. For example, such methods can be used to determine whether a subject can be effectively treated with a therapeutic compound for a biomarker-associated disorder (i.e., biomarker-associated medical condition). Thus, the invention provides methods for determining whether a subject can be effectively treated with a compound for a disorder associated with biomarker expression or activity in which a test sample is obtained and biomarker molecule is detected using prognostic compound (e.g., wherein the presence, or altered level of expression of, the biomarker molecule compared with the level of expression of the biomarker in a reference is diagnostic for a subject that can be administered the compound to treat a biomarker-associated disorder.

In one embodiment, the level of the biomarker molecule in a blood or tissue sample obtained from a first subject is determined and compared with the level found in a blood sample or a sample from the same tissue type obtained from an second subject free of the biomarker-associated disease. An overabundance (or underabundance) of the biomarker molecule in the sample obtained from the first subject suspected of having the biomarker associated disease compared with the sample obtained from the healthy (second) subject is indicative of the biomarker-associated disease in the subject being tested. Further testing may be required to make a positive diagnosis.

In one embodiment, the level of the biomarker molecule (e.g., serum gelsolin) in a blood or tissue sample obtained from a subject at a first time point is determined and compared with the level found in a blood sample or a sample from the same tissue type obtained from the subject at a later time point. An overabundance (or underabundance) of the biomarker molecule in the sample obtained from the subject at the first time point can be compared with the sample obtained from the subject at the second time point wherein the decrease (underabundance) of the biomarker level between the first time point compared with the biomarker level at the second time point is indicative of a subject who is in need of gelsolin replacement therapy. Further testing may be required to make a positive diagnosis.

There are a number of diseases in which the degree of overexpression (or underexpression) of certain biomarker molecules is known to be indicative of whether a subject with the disease is likely to respond to a particular type of therapy or treatment. Thus, the method of detecting a biomarker molecule in a sample can be used as a method of prognosis, e.g., to evaluate the likelihood that the subject will respond to the therapy or treatment. Accordingly, in another embodiment, the level of at least one biomarker molecules in a blood or tissue sample obtained from a first subject is determined and compared with the level of the at least one biomarker molecules found in a blood sample or a sample from the: same tissue type obtained from a second subject, or standard reference population, responsive to a compound, e.g., a therapeutic compound of interest. Similarity in the level or pattern of expression of the at least one biomarker molecules in a blood or tissue sample obtained from a first subject compared with the level of the at least one biomarker molecules found in a blood sample or a sample from the same tissue type obtained from the second subject, or standard reference population, indicates that the first subject will be responsive to the compound, e.g., therapeutic compound of interest. That is, the level of the relevant biomarker in a suitable tissue or biological sample from the subject is determined and compared with a suitable control, e.g., the level in subjects with the same disease but who have responded favorably to the treatment. The degree to which the biomarker is overexpressed (or underexpressed) in the sample compared with the control may be predictive of likelihood that the subject will not respond favorably to the treatment or therapy (e.g. tolerate chemotherapy). The greater the overexpression (or underexpression) relative to the control, the less likely the subject will respond to the treatment.

There are a number of diseases in which the degree of overexpression (or underexpression) of certain biomarker molecules, i.e., biomarker-associated disease or medical condition, is known to be indicative of whether a subject will develop a disease. Thus, the method of detecting a biomarker in a sample can be used as a method of predicting whether a subject will develop a disease. The level of a one or more biomarkers in a suitable tissue or blood sample from a subject at risk of developing the disease is determined and compared with a suitable control, e.g., the level in subjects who are not at risk of developing the disease. The degree to which the one or more biomarkers is overexpressed (or underexpressed) in the sample compared with the control may be predictive of likelihood that the subject will develop the disease. The greater the overexpression (or underexpression) relative to the control, the more likely the subject will development the disease.

The methods described herein can be performed, for example, by utilizing pre-packaged diagnostic kits comprising at least one probe reagent, e.g., anti-gelsolin polypeptide antibody described herein, which can be conveniently used, e.g., in clinical setting to diagnose patients exhibiting symptoms or family history of a disease or illness involving a biomarker of the invention. Furthermore, any cell type or tissue in which a biomarker of the invention is expressed can be utilized in the prognostic assays described herein.

Monitoring Clinical Efficacy. In one embodiment, the present invention provides for monitoring the influence of agents (e.g., drugs, compounds, or small molecule) on the expression of gelsolin or gelsolin-like polypeptides. Such assays can be applied in basic drug screening and in clinical trials. For example, the effectiveness of an agent to increase (or decrease) gelsolin or gelsolin-like polypeptide levels can be monitored in clinical trials of subjects exhibiting decreased expression of gelsolin. An agent that affects the expression of gelsolin or gelsolin-like polypeptides can be identified by administering the agent and observing a response. In this way, the expression pattern of the gelsolin or gelsolin-like polypeptide can serve as a marker, indicative of the physiological response of the subject to the agent. Accordingly, this response state may be determined before, and at various points during, treatment of the individual with the agent.

Subject Classification. Standard control levels of a gelsolin or gelsolin-like polypeptide are determined by measuring levels in different control groups. The control levels are then compared with the measured level of a gelsolin or gelsolin-like polypeptide in a given subject. The subject can be classified or assigned to a particular group based on how similar the measured levels were compared to the control levels for a given group.

As one of skill in the art will understand, there will be a certain degree of uncertainty involved in making this determination. Therefore, the standard deviations of the control group levels can be used to make a probabilistic determination and the method of this invention are applicable over a wide range of probability-based genotype group determinations. Thus, for example, and not by way of limitation, in one embodiment, if the measured level of the gelsolin polypeptide falls within 2.5 standard deviations of the mean of any of the control groups, then that individual may be assigned to that group. In another embodiment if the measured level of the gene expression product falls within 2.0 standard deviations of the mean of any of the control groups then that individual may be assigned to that group. In still another embodiment, if the measured level of the gene expression product falls within 1.5 standard deviations of the mean of any of the control groups then that individual may be assigned to that group. In yet another embodiment, if the measured level of the gelsolin polypeptide is 1.0 or less standard deviations of the mean of any of the control groups levels then that individual may be assigned to that group.

Thus, this process allows determination, with various degrees of probability, which group a specific subject should be placed in, and such assignment would then determine the risk category into which the individual should be placed.

Kits

Also within the scope of the invention are kits comprising the gelsolin binding agent compositions (e.g., monoclonal antibodies) of the invention and instructions for use. The kits are useful for detecting the presence of a gelsolin polypeptide or a gelsolin-like polypeptide in a biological sample e.g., any body fluid including, but not limited to, e.g., serum, plasma, lymph, cystic fluid, urine, stool, cerebrospinal fluid, acitic fluid or blood and including biopsy samples of body tissue. For example, the kit can comprise: one or more gelsolin binding agents capable of binding a gelsolin polypeptide or a gelsolin-like polypeptide in a biological sample (e.g. an antibody or antigen-binding fragment thereof having the same antigen-binding specificity of antibodies produced by a deposited cell line selected from the group consisting of: CGMCC Accession Nos: 2114, 2115, and 2116); means for determining the amount of the gelsolin polypeptide or gelsolin-like polypeptide in the sample; and means for comparing the amount of the gelsolin polypeptide or the gelsolin-like polypeptide in the sample with a standard. One or more of the gelsolin binding agents may be labeled. The kit components, (e.g., reagents) can be packaged in a suitable container. The kit can further comprise instructions for using the kit to detect the gelsolin polypeptide or the gelsolin-like polypeptide.

For antibody-based kits, the kit can comprise, e.g., 1) a first antibody, e.g., attached to a solid support, which binds to a polypeptide corresponding to a marker or the invention; and, optionally; 2) a second, different antibody which binds to either the polypeptide or the first antibody and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the invention may contain a written product on or in the kit container. The written product describes how to use the reagents contained in the kit, e.g., to use the biomarkers of the present invention in determining a strategy for preventing or treating a medical condition in a subject. In several embodiments, the use of the reagents can be according to the methods of the invention.

Prophylactic and Therapeutic Use of Gelsolin Replacement Therapy

General. The gelsolin binding agents and methods of the present invention can be used in conjunction with gelsolin replacement therapy. Specifically, the invention provides for both prophylactic and therapeutic methods of treating a subject at risk of (or susceptible to) a disorder or having a disorder associated with an aberrant gelsolin expression or activity. The gelsolin binding agents and methods are used, for example, to ascertain the suitability of gelsolin replacement therapy for a subject or monitor the efficacy of gelsolin replacement therapy in a subject receiving such therapy. In one embodiment, a therapeutically effective amount of recombinant or purified, native gelsolin compounds are administered so as to provide therapeutic benefits against the secondary toxic effects of excessive extracellular actin. By "excessive" extracellular actin is meant an amount of extracellular actin which exceeds the ability of the plasma proteins to bind and clear the actin from extracellular fluids without secondary tissue damage or toxic effects. By "secondary" tissue damage or toxic effects is meant the tissue damage or toxic effects which occur to otherwise healthy tissues, organs, and the cells therein, due to the presence of excessive extracellular actin in the plasma, usually as a result of a "primary" tissue injury elsewhere in the body. While not wishing to be limited by theory, infusion of gelsolin, results in a) binding to actin monomers so as to prevent their condensation into actin filaments, and/or b) cleavage of actin filaments to the monomeric state, and/or c) enhanced clearance of such actin complexed to actin-binding proteins or fragments thereof from the circulation or extracellular tissue environment.

Optionally, the administration is made during the course of adjunct therapy such as combined cycles of radiation, chemotherapeutic treatment, or administration of other cytoprotective or immunomodulatory agent. As such the binding agents of the present invention and a compound useful in adjunct therapy may be administrated simultaneously and sequentially to a subject in need of administration thereof.

In one aspect, the invention provides a method for preventing, in a subject, a disease or condition associated with an aberrant gelsolin expression or activity, by administering to the subject gelsolin. Administration of a prophylactic gelsolin binding agent can occur prior to the manifestation of symptoms characteristic of the aberrancy, such that a disease or disorder is prevented or, alternatively, delayed in its progression. In therapeutic applications, gelsolin is administered to a subject suspected of, or already suffering from, reduced serum gelsolin levels. An amount adequate to accomplish therapeutic or prophylactic treatment is defined as a therapeutically- or prophylactically-effective dose.

Determination of the Biological Effect of the gelsolin-Binding Agent-Based Therapeutic. In various embodiments of the invention, suitable in vitro or in vivo assays are performed to determine the effect of gelsolin replacement therapy and whether its administration is indicated for treatment of the affected tissue in a subject.

Typically, an effective amount of the compositions of the present invention, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. For administration of gelsolin, the dosage ranges from about 0.0001 to 100 mg/kg, and more usually 0.01 to 5 mg/kg every week, every two weeks or every three weeks, of the host body weight. For example dosages can be 1 mg/kg body weight or 10 mg/kg body weight every week, every two weeks or every three weeks or within the range of 1-10 mg/kg every week, every two weeks or every three weeks. In one embodiment, a single dosage of antibody range from 0.1-10,000 micrograms per kg body weight. In one embodiment, antibody concentrations in a carrier range from 0.2 to 2000 micrograms per delivered milliliter. An exemplary treatment regime entails administration once per every two weeks or once a month or once every 3 to 6 months. Gelsolin is usually administered on multiple occasions. Intervals between single dosages can be daily, weekly, monthly or yearly. Intervals can also be irregular as indicated by measuring blood levels of antibody in the subject. In some methods, dosage is adjusted to achieve a serum gelsolin concentration in the subject of from about 75 µg/mL to about 125 µg/mL, 100 µg/mL to about 150 µg/mL, from about 125 µg/mL to about 175 µg/mL, or from about 150 µg/mL to about 200 µg/mL. Alternatively, gelsolin can be administered as a sustained release formulation, in which case less frequent administration is required. Dosage and frequency vary depending on the half-life of the gelsolin binding agent in the subject. The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the patent can be administered a prophylactic regime.

Toxicity. Preferably, an effective amount (e.g., dose) of gelsolin described herein will provide therapeutic benefit without causing substantial toxicity to the subject. Toxicity of the gelsolin described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the gelsolin described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

Formulations of Pharmaceutical Compositions. According to the methods of the present invention, the gelsolin can be incorporated into pharmaceutical compositions suitable for administration. The pharmaceutical compositions generally comprise recombinant or substantially purified native gelsolin and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (see, e.g., *Remington's Pharmaceutical Sciences*, Mack Publishing Co., Easton, Pa. 18$^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the gelsolin binding agent are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically-acceptable esters include esters formed from carboxy, sulfonyloxy, and phosphonoxy groups present in the gelsolin binding agent, e.g., $C_{1-6}$ alkyl esters. When there are two acidic groups present, a pharmaceutically-acceptable salt or ester can be a mono-acid-mono-salt or ester or a di-salt or ester; and similarly where there are more than two acidic groups present, some or all of such groups can be salified or esterified. The gelsolin binding agent named in this invention can be present in unsalified or unesterified form, or in salified and/or esterified form, and the naming of such gelsolin binding agent is intended to include both the original (unsalified and unesterified) compound and its pharmaceutically-acceptable salts and esters. Also, certain gelsolin binding agent named in this invention can be present in more than one stereoisomeric form, and the naming of such gelsolin binding agent is intended to include all single stereoisomers and all mixtures (whether racemic or otherwise) of such stereoisomers. A person of ordinary skill in the art, would have no difficulty determining the appropriate timing, sequence and dosages of administration for particular drugs and compositions of the present invention.

Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the gelsolin binding agent, use thereof in the compositions is contemplated. Supplementary active compounds can also be incorporated into the compositions.

A pharmaceutical composition of the invention is formulated to be compatible with its intended route of administration. The gelsolin compositions of the present invention can be administered by parenteral, topical, intravenous, oral, subcutaneous, intraarterial, intradermal, transdermal, rectal, intracranial, intraperitoneal, intranasal; intramuscular route or as inhalants. The gelsolin can optionally be administered in combination with other agents that are at least partly effective in treating various diseases including various actin- or microfilament-related diseases.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfate; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the gelsolin binding agent in the required amount in an appropriate solvent with one or a combination of ingredients enumerated above, as required, followed by filtered sterilization. Generally, dispersions are prepared by incorporating the binding agent into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The agents of this invention can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the binding agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the gelsolin binding agent are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the gelsolin binding agent is formulated into ointments, salves, gels, or creams as generally known in the art.

The gelsolin an also be prepared as pharmaceutical compositions in the form of suppositories (e.g., with conventional suppository bases such as cocoa butter and other glycerides) or retention enemas for rectal delivery.

In one embodiment, the gelsolin is prepared with carriers that will protect the gelsolin against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

Preparation of Recombinant Gelsolin. Most of the Discussion Below Pertains to production of gelsolin by culturing cells transformed with a vector containing gelsolin nucleic acid and recovering the polypeptide from the cell culture. It is further envisioned that the gelsolin of this invention may be produced by purifying native gelsolin from plasma using affinity purification (described above). The proteins and DNA sequences encoding the proteins may be produced using standard methods. Purification can also be accomplished using standard procedures such as isolating proteins using chromatography, using antibodies directed against the polypeptides, or by producing the polypeptides in a form in which they are fused to a moiety (or tag) that aids in purification and which can then be cleaved.

A polynucleotide encoding a gelsolin or gelsolin-like polypeptide (for example, the polypeptide of SEQ ID NO.: 1) may be inserted into any of the many commercially available expression vectors using reagents and techniques that are well known in the art. In preparing the recombinant expression constructs, the various polynucleotides of the present invention may be inserted or substituted into a bacterial plasmid-vector. Any convenient plasmid may be employed, which will be characterized by having a bacterial replication system, a marker which allows for selection in a bacterium and generally one or more unique, conveniently located cloning sites. Numerous plasmids, also referred to as vectors, are available for transformation. Suitable vectors include, but are not limited to, the following: viral vectors, such as lambda vector system gt11, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK+/−. or KS+/− (Stratagene, La Jolla, Calif.), and any derivatives thereof. Also suitable are yeast expression vectors, which may be highly useful for cloning and expression. Exemplary yeast plasmids include, without limitation, pPICZ, and pFLD. (Invitrogen, Carlsbad, Calif.). The selection of a vector will depend on the preferred transformation technique and target host cells.

The nucleic acid molecule encoding gelsolin is inserted into a vector in the 5' to 3' direction, such that the open reading frame is properly oriented for the expression of the encoded protein under the control of a promoter of choice. In this way, the gelsolin structural gene is said to be "operably linked" to the promoter. Single or multiple nucleic acids may be inserted into an appropriate vector in this way, each under the control of suitable promoters, to prepare a nucleic acid construct of the present invention.

Certain regulatory sequences may also be incorporated into the expression constructs of the present invention. These include non-transcribed regions of the vector, which interact with host cellular proteins to carry out transcription and translation. Such elements may vary in their strength and specificity. Depending on the vector system and host utilized, any number of suitable transcription and/or translation elements, including constitutive, inducible, and repressible promoters, as well as minimal 5' promoter elements may be used.

A constitutive promoter is a promoter that directs constant expression of a gene in a cell. Examples of some constitutive promoters that are widely used for inducing expression of heterologous polynucleotides include the ADH1 promoter for expression in yeast, those derived from any of the several actin genes, which are known to be expressed in most eukaryotic cell types, and the ubiquitin promoter, which is the promoter of a gene product known to accumulate in many cell types. Examples of constitutive promoters for use in mammalian cells include the RSV promoter derived from Rous sarcoma virus, the CMV promoter derived from cytomegalovirus, β-actin and other actin promoters, and the EF1α promoter.

Also suitable as a promoter in the plasmids of the present invention is a promoter that allows for external control over the regulation of gene expression. One way to regulate the amount and the timing of gene expression is to use an inducible promoter. Unlike a constitutive promoter, an inducible promoter is not always optimally active. An inducible promoter is capable of directly or indirectly activating transcription of one or more DNA sequences or genes in response to an inducing agent (or inducer). Some inducible promoters are activated by physical means, such as the heat shock promoter (HSP), which is activated at certain temperatures. Other promoters are activated by a chemical means, for example, IPTG. Other examples of inducible promoters include the metallothionine promoter, which is activated by heavy metal ions, and hormone-responsive promoters, which are activated by treatment of certain hormones. In the absence of an inducer, the nucleic acid sequences or genes under the control of the inducible promoter will not be transcribed or will only be minimally transcribed. Promoters of the nucleic acid construct of the present invention may be either homologous (derived from the same species as the host cell) or heterologous (derived from a different species than the host cell).

Once the nucleic acid construct of the present invention has been prepared, it may be incorporated into a host cell. This is carried out by transforming or transfecting a host or cell with a plasmid construct of the present invention, using standard procedures known in the art, such as described by Sambrook et al., *Molecular Cloning: A Laboratory Manual, Third Edition*, Cold Spring Harbor: Cold Spring Harbor Laboratory Press, New York (2001). Suitable hosts and cells for the present invention include, without limitation, bacterial cells, virus, yeast cells, insect cells, plant cells, and mammalian cells, including human cells, as well as any other cell system that is suitable for producing a recombinant protein. Exemplary bacterial cells include, without limitation, *E. coli* and *Mycobacterium* sp. Exemplary yeast hosts include without limitation, *Pischia pastoris, Saccharomyces cerevisiae*, and *Schizosaccharomyces pombe*. Methods of transformation or transfection may result in transient or stable expression of the genes of interest contained in the plasmids. After transformation, the transformed host cells can be selected and expanded in suitable culture. Transformed cells are first identified using a selection marker simultaneously introduced into the host cells along with the nucleic acid construct of the present invention. Suitable markers include markers encoding for antibiotic resistance, such as resistance to kanamycin, gentamycin, ampicillin, hygromycin, streptomycin, spectinomycin, tetracycline, chloramphenicol, and the like. Any known antibiotic-resistance marker can be used to transform and select transformed host cells in accordance with the present invention. Cells or tissues are grown on a selection medium containing an antibiotic, whereby generally only those transformants expressing the antibiotic resistance marker continue to grow. Additionally, or in the alternative, reporter genes, including, but not limited to, β-galactosidase, β-glucuronidase, luciferase, green fluorescent protein (GFP) or enhanced green fluorescent protein (EGFP), may be used for selection of transformed cells. The selection marker employed will depend on the target species.

Recombinant gelsolin may be purified using standard anion exchange chromatography. Oberley, R. E. et al., Am J Physiol Lung Cell Mol Physiol 287: L296-306 (2004).

To obtain the gelsolin protein, expression is induced if the coding sequences is under the control of an inducible promoter. To isolate the protein, the host cell carrying an expression vector is propagated, homogenized, and the homogenate is centrifuged to remove bacterial debris. The supernatant is then subjected to sequential ammonium sulfate precipitation. The fraction containing the protein of the present invention is subjected to gel filtration in an appropriately sized dextran or polyacrylamide column to separate the proteins. If necessary, the protein fraction may be further purified by HPLC. Alternative methods of protein purification may be used as suitable. See J. E. Coligan et al., eds., *Current Protocols in Protein Science* (John Wiley & Sons, 2003). Upon obtaining the substantially purified recombinant protein, the protein may be administered to a subject as described herein.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of binding agent calculated to produce the desired therapeutic effect in association with the required pharmaceutical carrier. The specification for the dosage unit forms of the invention are dictated by and directly dependent on the unique characteristics of the binding agent and the particular therapeutic effect to be achieved, and the limitations inherent in the art of compounding such gelsolin binding agent for the treatment of a subject.

The following EXAMPLES are presented in order to more fully illustrate the preferred embodiments of the invention. These EXAMPLES should in no way be construed as limiting the scope of the invention, as defined by the appended claims.

EXAMPLES

The present invention is further illustrated by the following examples, which should not be construed as limiting in any way.

Example 1

Preparation of Gelsolin Antigens

1. Cloning of Gelsolin and Gelsolin Fragments

The cDNAs encoding the full-length, N-terminal, and C-terminal fragments of human gelsolin were cloned by the following RT-PCR method using:

a. Template

Total RNA was isolated from a HELA human cancer cell line. cDNA was synthesized using a reverse transcription kit (Promega, Madison, Wis., cat. no. A3500), according to the manufacturer's instructions. The cDNA was used as a template for PCR.

b. PCR Primers

The following paired PCR primers for cloning full length human gelsolin, and the N- and C-terminal fragments are shown in Table 5:

TABLE 5

PCR Primers for Cloning Gelsolin Fragments.

| Gelsolin Protein | Primers | | SEQ ID NO | Amino acid range |
|---|---|---|---|---|
| Full-length (GF) | 5' | CACCGGATCCCTGCTTTGCGCGCTGTCCCTG | SEQ ID NO.: 5 | 13-782 |
| | 3' | CTCGAGTCAGGCAGCCAGCTCAGCCAT | SEQ ID NO.: 6 | |

TABLE 5-continued

PCR Primers for Cloning Gelsolin Fragments.

| Gelsolin Protein | Primers | | SEQ ID NO | Amino acid range |
|---|---|---|---|---|
| N-terminus (GN) | 5' | CACCGGATCCCTGCTTTGCGCGCTGTCCCTG | SEQ ID NO.: 7 | 13-440 |
| | 3' | TTACTCGAGTCCATATGTGGCAGGGTCCAC | SEQ ID NO.: 8 | |
| C-terminus (GC) | 5' | CACCGGATCCGCCACATATGGACAGTTCT | SEQ ID NO.: 9 | 440-782 |
| | 3' | CTCGAGTCAGGCAGCCAGCTCAGCCAT | SEQ ID NO.: 10 | | c. PCR Reaction

The following reagents were combined in the PCR reaction (100 μl final volume): template cDNA, 5 μl of total 33 μl reaction; 10 μmol of each 5' and 3' primer; 10×PCR buffer, 10 μl; dNTPs (2.5 mM each), 4 μl; and Taq polymerase (Promega), 5 units.

The PCR reaction was conducted as follows. The solution was first heated at 94° C. for 2 min, followed by 40 cycles of 94° C. for 30 s, 52° C. for 1 min, and 72° C. for 3 min. The reaction was then incubated at 72° C. for 10 min for a final extension. The amplified DNA fragments, thus obtained, were separated on a 1% agarose gel containing 0.25 μg/ml ethidium bromide. The PCR products were visualized using UV light and the bands corresponding to the expected size of the amplification product were recovered using the Gene Clean kit (BIO101, Irvine, Calif.).

d. Cloning of PCR Products

The DNA fragment was cloned using the TOPO100 expression Cloning Kit (Invitrogen, Carlsbad, Calif.). This was performed as follows. The DNA fragment recovered from the PCR reaction solution, together with 50 ng of TOPO vector which was provided with the cloning kit, was mixed with 1 μl of 10× ligase reaction buffer (6 mM Tris-HCl (pH 7.5), 6 mM magnesium chloride, 5 mM sodium chloride, 7 mM β-mercaptoethanol, 0.1 mM ATP, 2 mM DTT, 1 mM spermidine, and 0.1 mg/ml bovine serum albumin), to which 4 units of T4 DNA ligase (1 μl) had been added. The total volume of the mixture was adjusted to 10 μl with sterile deionized water, and the resulting ligase solution was incubated at 14° C. for 15 h. After this time, 2 μl of the ligase reaction solution was added to 50 μl of competent E. coli strain TOP10F, which was provided with the TA cloning kit and brought to competence in accordance with the instruction manual, and the resulting mixture was kept on ice for 30 min, then heated at 42° C. for 30 s, and then again chilled on ice for 5 min. Next, 500 μl of medium containing 2% (w/v) tryptone, 0.5% (w/v) yeast extract, 0.05% (w/v) sodium chloride, 2.5 mM potassium chloride, 1 mM magnesium chloride, and 20 mM glucose (hereinafter referred to as "SOC" medium) was added to the culture, and the mixture was incubated for 1 h at 37° C. with shaking. After this time, the culture was spread on an L-broth agar plate (1% (w/v) tryptone, 0.5% (w/v) yeast extract, 0.5% (w/v) sodium chloride, 0.1% (w/v) glucose, and 0.6% (w/v) bacto-agar (Difco, Detroit, Mich.)), containing 100 μg/ml ampicillin Ampicillin resistant colonies appearing on the plate were selected and scraped off with a platinum transfer loop, and cultured in L-broth medium containing 100 μg/ml ampicillin at 37° C., overnight, with shaking at 200 r.p.m. After incubation, the cells were harvested by centrifugation, from which plasmid DNA was prepared by the alkali method as described in Sambrook et al., *Molecular Cloning: A Laboratory Manual*, Second Ed. (Cold Spring Harbor Laboratory Press, Cold Spring Harbor, N.Y., 1989).

2. Expression and Purification of Gelsolin Proteins

The cDNA encoding the full-length, the N-terminal or the C-terminal fragment of human gelsolin was inserted into the TOPO100 vector (Invitrogen, Carlsbad, Calif.). The resulting plasmids were transformed into the E. coli strain BL21 (DE3), which was grown in LB media to exponential phases and induced with 0.4 mM isopropyl-1-thio-β-D-galactopyranoside for 3 h. Cells were pelleted by centrifugation and the supernatant removed. The pelleted cells were resuspended in lysis buffer (8 M urea, 20 mM Tris-HCl), and further disrupted by sonication. This mixture was clarified by centrifugation (14,000×g for 15 min) and the supernatant recovered. The expressed recombinant human gelsolin polypeptide was purified from the clarified supernatant using a Ni-NTA superflow column (Qiagen, Valencia, Calif.) according to manufacturer's instructions. The purified gelsolin protein preparation was dialyzed against PBS at 4° C. overnight. The protein concentration was determined by BCA assay (Pierce, Woburn, Mass.), and aliquots were stored at −80° C. until use for immunization.

Purified gelsolin protein preparations (1 μg) were characterized by separation on 10% SDS-PAGE and staining with Coomassie Blue. After destain, the gel was scanned using an HP photographic scanner. The results are shown in FIG. 1 (Lane 1: molecular weight marker; Lane 2: purified human plasma gelsolin purchased from Cytoskeleton, Inc. (Denver, Colo.); Lane 3: recombinant full-length ("FL") gelsolin; Lane 4: recombinant N-terminal gelsolin fragment; Lane 5: recombinant C-terminal gelsolin fragment).

Example 2

Generation of Monoclonal Antibodies Against Human Gelsolin

1. Immunization

Female, Balb/c mice (Jackson Laboratory, Bar Harbor, Me.) of 6-8 weeks of age, were immunized with one of: (1) native plasma gelsolin (NG, available from Cytoskeleton, Inc.); (2) recombinant full-length gelsolin (GF, amino acids 23-782 of SEQ ID NO.: 1), (3) recombinant N-terminal gelsolin (GN, amino acids 23-440 of SEQ ID NO.: 1), or (4) recombinant C-terminal gelsolin (GC, amino acids 440-782 of SEQ ID NO.: 1). For the initial foot-pad immunization, 1 mg/mL of each immunogen was emulsified with an equal volume of Freund's complete adjuvant (Difco, Detroit, Mich.). The mixture (100 μL) was injected into the foot pads of the mice. Seven days later, the foot pads of the mice were injected with 100 μL of each immunogen emulsified with an equal volume of adjuvant. Mice were further boosted weekly (for 3 weeks) with foot pad injection of 250 μg immunogen in 100 μL PBS in combination with i.p. injection of 100 μg murine recombinant B Lymphocyte Stimulator polypeptide (BLyS) in 0.5 mL PBS. Three days after the last injection, lymphocytes from the local lymph nodes of the immunized mice were collected.

2. Cell Fusion

Single cell suspension was prepared from lymph nodes, and mixed with NS1 myeloma cells at a ratio of 2:1. The resulting mix was washed three times with PRMI-1640. One milliliter, 37° C. pre-warmed, of 50% (v/v) polyethylene glycol 1500 (Boehringer Mannheim, Basel, Switzerland) was then slowly added to the tube, while stirring the pellet using the tip of a pipette. Subsequently, 50 mL of serum-free RPMI medium, pre-warmed to 37° C., was slowly added. The resulting mix was then centrifuged, the supernatant discarded and 50 mL of HAT medium containing 12% (v/v) FCS was added while stirring gently with the tip of a pipette. The suspension was dispensed into 96-well cell culture microplates at 100 µL/well. The plate was then incubated at 37° C. in an atmosphere of 5% (v/v) $CO_2$ for 7-10 days.

3. Screening of Monoclonal Antibody

The screening was conducted according to Table 6. ELISA plates were coated with 1 µg/mL of the gelsolin immunogen protein at 4° C. overnight. Unbound gelsolin immunogen was rinsed from the wells by washing three times with PBS. Non-specific binding sites in the wells were blocked by incubating the wells with 3% (w/v) BSA PBS at room temperature for 1 h. The blocking buffer was removed prior to addition of hybridoma supernants without washing. One hundred microliters (100 µL) of hybridoma culture supernatant was then added to appropriate wells and the plate was incubated for 1 h at 37° C. to allow binding of anti-gelsolin antibody. Unbound material was removed by rinsing the wells three times with PBS (5 min each). Bound anti-gelsolin antibody was detected by incubating wells (30 min; 37° C.) with HRP-conjugated anti-mouse IgG antibody (1:10,000). Unbound HRP-conjugated anti-mouse IgG antibody was removed by rinsing the wells three times with PBS (5 min each). Anti-gelsolin antibody-HRP-conjugated anti-mouse IgG antibody complexes were measured using SureBlue TMB 1-Component Microwell Peroxidase Substrate (KPL, Gaithersburg, Md.). Specifically, SureBlue TMB 1-Component Microwell Peroxidase Substrate (KPL, Gaithersburg, Md.) was added to the wells and the plate was incubated for 10 min to allow HRP-mediated conversion of the substrate. The enzymatic reaction was stopped with the addition of 100 µl $2NH_2SO_4$. The optical density of the sample wells was then measured at 450 nm/650 nm using an ELISA plate reader.

TABLE 6

Screening Strategy

| Group | Immunogen | First Screening | Second Screening |
|---|---|---|---|
| 1 | Native Gelsolin (NG) | NG | GF |
|   |   |   | GN |
|   |   |   | GC |
| 2 | Full-Length Recombinant Gelsolin (FL) | GF | NG |
|   |   |   | GN |
|   |   |   | GC |
| 3 | N-terminal Recombinant Gelsolin (GN) | GN | NG |
|   |   |   | GF |
|   |   |   | GC |
| 4 | C-terminal Recombinant Gelsolin (GC) | GC | NG |
|   |   |   | GF |
|   |   |   | GN |

A second confirmatory screening procedure was used to further define the binding specificity of positive clones. All positive clones were subjected to a secondary confirmatory ELISA screening (as detailed above) using "secondary screening" polypeptides defined in Table 6. The results of the screening are shown in Table 7. The number of positive clones compared with the total clones tested for each screen are indicated in Table 7. The primary screening tested 480 clones for binding to each gelsolin immunogen. Those clones which were positive for binding to the gelsolin immunogen were tested for binding to the other gelsolin immunogens of the study.

TABLE 7

Primary and Secondary Screening Results

| | Screening Protein | | | |
|---|---|---|---|---|
| Immunogen | NG | GF | GN | GC |
| NG | 34/480 | 2/34 | 1/34 | 1/34 |
| GF | 31/85 | 85/480 | 31/85 | 25/85 |
| GN | 4/37 | 19/37 | 37/480 | 0/37 |
| GC | 30/76 | 30/76 | 6/76 | 76/480 |

Three clones GN3E9, GC1C10, and GF2D6 were found to specifically bind to native gelsolin (NG) and/or recombinant gelsolin (GF) as well as either N- or C-terminal fragments (GN or GC), with high binding affinity. Therefore, these clones were selected as exemplary antibodies useful in the gelsolin detection methods of the invention (described below).

4. Cloning by Limiting Dilution

The original GN3E9, GC1C10, and GF2D6 hybridoma cells were diluted to 0.3 cells per mL with RPMI-1640 containing 12% (v/v) FCS and cultured in two 96-well plates in the presence of $10^5$ thymocytes of Balb/c mice as feeder cells. Seven to ten days later (7-10 days), Culture supernatants (100 µL) were collected seven to ten days (7-10 days) later and antibody production was determined by ELISA as described above. The positive clones were subsequently subcloned three times by limiting dilution.

5. Analysis of Isotypes of Anti-Gelsolin Antibodies

The isotype of selected anti-gelsolin antibodies was determined by goat anti-murine isotype specific antibodies (SouthernBiotech, Birmingham, Ala.). Isotype of GN3E9 was determined as murine IgG2b kappa, and the isotype of GC1C10 and GF2D6 were determined as murine IgG1 kappa.

6. Purification of GN3E9, GC1C10, and GF2D6 Monoclonal Antibodies

GN3E9 was purified by affinity chromatography using Sepharose GL-4B affinity purification medium (Pharmacia, Uppsala, Sweden). The GC and GF2D6 antibodies were purified by affinity chromatograpy using Protein G-Sepharose CL-4B affinity purification medium (Pharmacia, Uppsala, Sweden). The culture supernatants were applied to the column with a flow rate of 2 ml per min. After the culture supernatant was passed through the column, it was washed with 50 ml PBS. The protein was eluted with elution buffer (0.1 M glycine (pH 2.4), 0.15 M NaCl). The optical density of each eluted fraction (1 ml) was measured at OD280 nm. The fractions with OD280>0.1 units were collected. After addition of 100 µl of neutralization buffer (1M Tris-HCl pH 8.5) to the fraction, the eluates were placed separately in dialysis tubing, and the eluates dialyzed against 1 L of PBS (pH 7.5) at 4° C. The dialysis buffer was changed twice. Each affinity purified antibody was concentrated to 1 mg/ml, sterilized and stored at 4° C. until use.

Example 3

Characterization of Selected Gelsolin Binding Agents of the Present Invention

Three selected antibodies (e.g., GN3E9, GF2D6, and GC1C10) as well as commercial anti-human gelsolin antibody GS2C4 (Sigma Chemical Co., St. Louis, Mo.), were characterized using ELISA, western blot, and immunoprecipitation techniques. Using the methods described below, it would also be possible for the skilled artisan to generate and/or compare additional gelsolin binding agents to the antibodies shown in these examples.

1. Determination of Binding Characteristics of Gelsolin Binding Agents by ELISA

Studies were performed to determine the binding characteristics of select gelsolin binding agents as detailed below. An ELISA plate was coated with 1 µg/mL of native human plasma gelsolin purified from human plasma (purchased from Cytoskeleton, Inc., Denver, Colo.), the recombinant full-length gelsolin (GF), the recombinant N-terminal fragment (GN), the recombinant C-terminal fragment (GC), or BSA as a background control in PBS at 4° C. overnight. Unbound gelsolin polypeptide was rinsed from the wells by washing the plate three times with PBS (5 min each). Non-specific binding sites in the wells were blocked by incubating the wells with 3% (w/v) BSA PBS at room temperature for 1 h. A varying amount of antibody (0.001 µg/mL-10 µg/mL) was added at 37° C. for 30 min. Unbound antibody was removed from the wells by rinsing three times with PBS (5 min each). Bound anti-gelsolin antibody was detected by incubating wells (30 min; 37° C.) with HRP-conjugated anti-mouse IgG antibody (1:10,000, 100 µl). Unbound HRP-conjugated anti-mouse IgG antibody was removed by rinsing the wells three times with PBS (5 min each). Anti-gelsolin antibody-HRP-conjugated anti-mouse IgG antibody complexes were measured using SureBlue TMB 1-Component Microwell Peroxidase Substrate (KPL, Gaithersburg, Md.). Specifically, SureBlue TMB 1-Component Microwell Peroxidase Substrate (KPL, Gaithersburg, Md.) was added to the wells and the plate was incubated for 10 min to allow HRP-mediated conversion of the substrate. The enzymatic reaction was stopped with the addition of 100 µl $2NH_2SO_4$. The optical density of the sample wells was then measured at 450 nm/650 nm using an ELISA plate reader.

Figure 2:
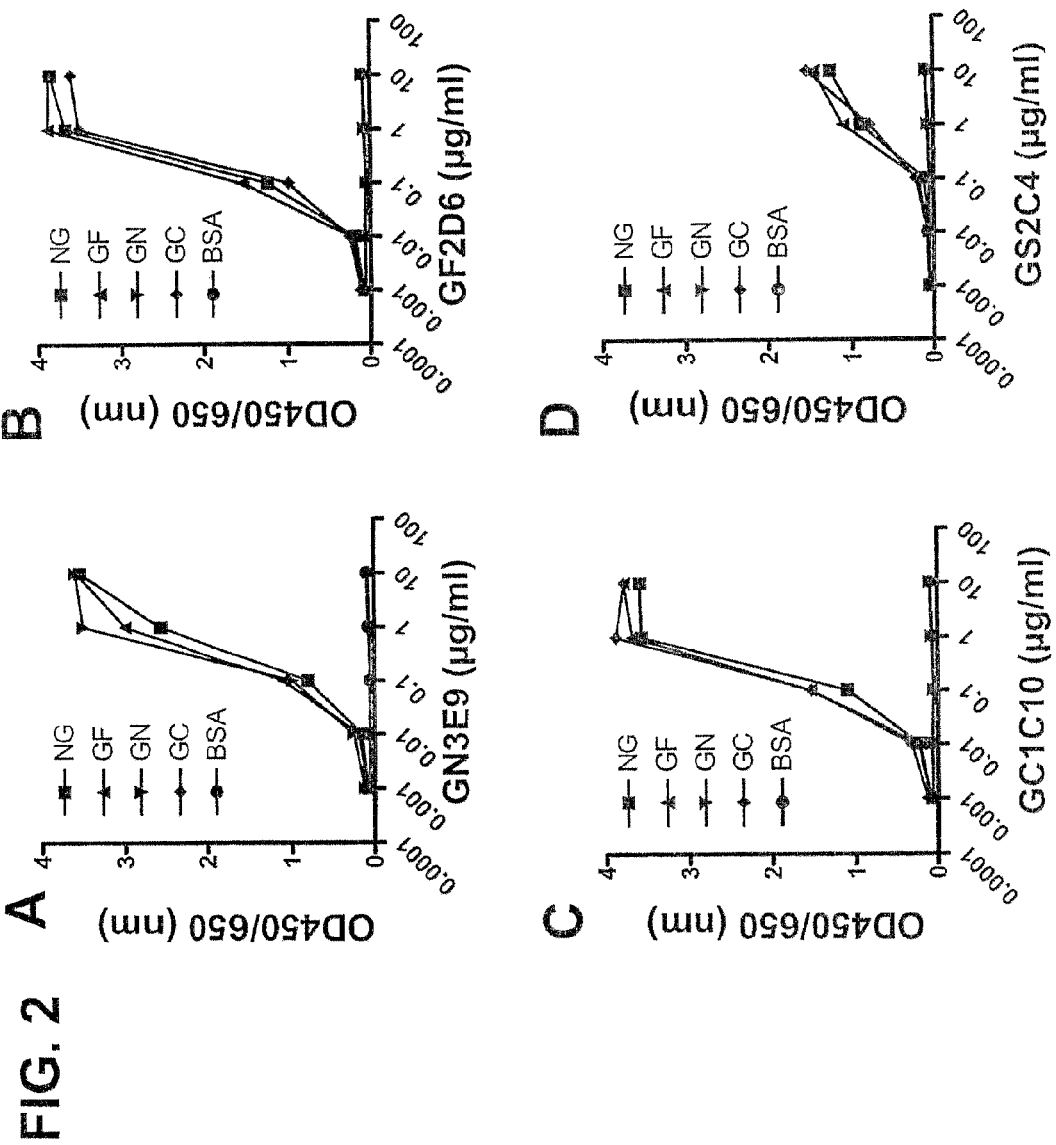
FIG. 2 is an ELISA analysis of the binding charateriscs of anti-gelsolin monoclonal antibodies to different forms of human gelsolin (NG: native gelsolin; GF: full-length recombinant gelsolin; GN: recombinant N-terminal gelsolin fragment; GC: recombinant C-terminal gelsolin fragment) and BSA control. Each panel presents data from a different antibody: Panel A. GN3E9 (FIG. 2A); Panel B. GF2D6 (FIG. 2B); Panel C. GC1C10 (FIG. 2C); and Panel D. GS2C4 (FIG. 2D).

A summary of the results of studies performed to determine the binding characteristics of select gelsolin binding agents as detailed below are shown in FIG. 2. In panel A, GN3E9 showed a dose-dependent response to native gelsolin, recombinant full-length, and recombinant N-terminal gelsolin fragment, but not to the C-terminal fragment or BSA, indicating that GN3E9 is an antibody directed against the N-terminal portion of gelsolin. In panels B and C, GF2D6 and GC1C10, respectively, showed a dose-dependent response to native gelsolin, recombinant full-length, and recombinant C-terminal gelsolin fragment, but not to the N-terminal fragment or BSA, indicating that both GF2D6 and GC1C10 are antibodies directed against the C-terminal portion of gelsolin. The commercial anti-gelsolin antibody, GS2C4 (Panel D), showed a similar binding specificity to GF2D6 and GC1C 10, but the binding reactivity is much weaker compared to GF2D6 and GC1C10. The GF2D6 antibody appeared significantly less sensitive to detect immunoreactive gelsolin as judged by the lack of signal at 0.1 µg/ml concentration in GS2C4 (panel D) compared with signal observed for GN3E9 (panel A), GF2D6 (panel B), and GC1C10 (panel D) at the same concentration (0.1 µg/ml). As such, the gelsolin binding agent of the invention have the advantage of greater sensitivity to detect gelsolin and gelsolin related polypeptides when compared to commercial anti-gelsolin antibody GS2C4. The higher sensitivity of the gelsolin binding agents of the invention is advantageous for use of these binding agents in methods of the present invention.

2. Western Blot Analysis

Western blot analysis technique was used to assess the binding characteristics of the gelsolin binding agents of the invention in biological samples. That is, to further determine the binding specificity of anti-gelsolin antibodies, western blot analysis of human serum samples with anti-gelsolin antibodies was performed. The serum samples of two normal human subjects (20 µl of 1:20 dilution of serum in PBS) was fractionated by 10% SDS-PAGE and western blotted onto nitrocellulose membrane using standard techniques. After blocking the with electroblotted nitrocellulose membrane (blot) using 5% (w/v) non-fat milk at room temperature for 1 h. Each of four (4) replicate blots was probed with a purified anti-gelsolin antibody (1 µg/ml), i.e., GN3E9; GC1C10; GF2D5; or GS2C4, at room temperature for 2 h. Unbound anti-gelsolin antibody was rinsed from the blots by washing with PBS containing 0.02% Tween 20 at room temperature for 10 min with shaking. The bound anti-gelsolin antibody was detected by probing each blot with HRP-conjugated goat anti-murine IgG at room temperature for 1 h. Unbound HRP-conjugated goat anti-murine IgG was rinsed from the blots by washing with PBS containing 0.02% Tween20 at room temperature for 10 min with shaking. The anti-gelsolin-HRP-conjugated goat anti-murine IgG complexes were visualized using HRP-mediated chemiluminescence. Specifically, the blots were incubated with LumiGLO® Peroxidase Chemiluminescent Substrate (KPL, Gaithersburg, Md.) for 3 min, and exposed to X-ray films. The results are shown in FIG. 3. As shown in FIG. 3, GN3E9, GF2D6 and GS2C4, GC1C10 all bound a 90 kDa protein corresponding to the full-length plasma gelsolin. The GC1C10 antibody also bound other gelsolin-related polypeptides present in human serum including a 50 kDa protein(s). The 50 kDa gelsolin-like polypeptide is recognized by some antibodies which are directed to an epitope in the C-terminus of full-length gelsolin polypeptide.

3. Immunoprecipitation

To determine the ability of gelsolin binding agents of the invention to immunoprecipitate the native form of plasma gelsolin, GN3E9, GF2D6, GC1C10 and GS2C4 antibodies were conjugated to CNBr-activated Sepharose 4B (Amersham Pharmacia Biotech (Piscataway, N.J.), at a concentration of 2 mg/ml beads. The conjugation procedure was performed according to the manufacturer's instructions. Briefly, the pre-activated beads (660 mg; equal to approximately 2 mL final bead volume) were suspended in 15 volumes of 1 mM HCl and allowed to swell for 30 min. The beads were then washed with 15 gel volumes of cold (4° C.) 1 mM HCl followed by a wash with 15 volumes of coupling buffer (0.1M $NaHCO_3$ pH 8.3 containing 0.5M NaCl) to yield beads that are referred to as "washed gel". Each anti-gelsolin antibody (GC1C10; GF2D6; GN3E9; and GS2C4) was diluted in coupling buffer to 0.5 to 1.0 mg/ml and the pH was adjusted to pH 8.3. The washed gel was added to each anti-gelsolin antibody solution and the mixtures were incubated overnight at 4° C. to yield "coupled gels". The coupled gels were resuspended in 15 volumes of 1 M ethanolamine for 2-4 h at room temperature to block unused activated chemical conjugation sites on the activated beads. The blocked gels were then washed 8 times in 15 volumes with alternating 50 mM Tris, 1 M NaCl pH 8.0 and 50 mM glycine, 1 M NaCl pH 3.5 buffers followed by a final wash with 10 gel volumes of PBS to remove any unbound material.

To measure the gelsolin binding agents ability to immunoprecipitate human gelsolin from human serum, one milliliter (1 mL) human serum samples from normal subjects were incubated with 10 µl anti-gelsolin antibody-conjugated beads (i.e., GC1C10; GF2D6; GN3E9; or GS2C4 conjugated beads) or blank beads (i.e., beads without anti-gelsolin antibody conjugated to them) as a control at room temperature for 2 h. Unbound material was rinsed from the anti-gelsolin antibody-conjugated beads or blank beads by pelleting the bead by centrifugation (14,000 rpm, 3 min), removing the supernatant and then washing the pelleted beads by resuspension in PBS. Following five (5) wash cycles, materials bound to the anti-gelsolin antibody-conjugated beads or blank beads was removed under denaturing conditions by adding 40 µl SDS-PAGE loading buffer (SDS-PAGE loading buffer prepared by mixing 3× stock: 1M Tris-Cl pH 6.8 2.4 ml; 20% SDS 3 ml; Glycerol (100%) 3 ml; B-mercaptoethanol 1.6 ml; Bromophenol blue 0.006 g, 10 ml) to the pelleted beads and boiling the sample for 5 min. The immunoprecipitated proteins were fractionated on a 10% SDS-PAGE and visualized stained with Coomassie blue stain using standard techniques. The results are shown in FIG. 4. The lanes of the SDS-PAGE shown in FIG. 4 are as follows: Lane 1, blank beads (no antibody); lane 2, GC1C10; lane 3, GF2D6; lane 4, GN3E9; and lane 5, GS2C4. The anti-gelsolin antibodies of the invention (i.e., GC1C10, GF2D6 and GN3E9) shown in lanes 2-4, respectively, were able to immunoprecipitate ~90 kDa polypeptide consistent with the expected migration of full-length plasma gelsolin from human serum. In contrast, neither the commercial anti-gelsolin antibody, GS2C4 (Lane 5), nor the blank (no antibody control; Lane 1), exhibited the ability to precipitate a detectable ~90 kDa polypeptide from human serum sample. As such, the gelsolin binding agents of the invention tested in the present studies are distinct from the commercial anti-gelsolin antibody GS2C4 as they can precipitate immunoreactive ~90 kDa polypeptide consistent with the expected migration of full-length gelsolin polypeptide from human serum sample. The identity of this ~90 kDa polypeptide was confirmed to be full-length gelsolin polypeptide by mass spectroscopy analysis (See Example 4).

The ability of the select gelsolin binding agents of the invention tested to immunoprecipitate is advantageous for use of these binding agents in methods of the present invention. Specifically, gelsolin binding agents of the invention which can precipitate immunoreactive ~90 kDa polypeptide (i.e., native gelsolin) are likely superior to bind native gelsolin in biological sample and, consequently, prove to be more useful in the methods of the present invention when compared with other anti-gelsolin antibody (e.g., GS2C4) which cannot precipitate immunoreactive ~90 kDa polypeptide from human serum sample under the conditions like those employed in the present studies.

Example 4

Characterization of the Immunoreactive Polypeptide Bound by Gelsolin Binding Agents To confirm that the 90 kDa protein immunoprecipitated by anti-gelsolin antibodies is human gelsolin, the protein band was cut from SDS-PAGE and the contents subjected to analysis by mass spectroscopy at the National Center of Biomedical Analysis (Beijing, China) using standard techniques (see Lewis et al., Identification of Viral Mutants by Mass Spectrometry, Proc Nat Acad Sci USA 95: 8596-8601 (1998)). The data are shown in Table 8. A proteomics database (Swiss-Prot/TrEMBL) search indicated that the 90 kDa protein is human gelsolin. That is, the mass spectroscopy pattern observed for the 90 kDa polypeptide which was immunoprecipitated by the anti-gelsolin antibodies of the invention matched the fragmentation pattern reported for human plasma gelsolin (Swiss-Prot/TrEMBL). Accordingly, the 90 kDa polypeptide which was immunoprecipitated by the anti-gelsolin antibodies of the invention was confirmed as human plasma gelsolin.

TABLE 8

Mass spectrometry analysis of the immunoprecipitated 90 kDa protein.

| | m/z | Intens. |
|---|---|---|
| 1 | 998.57 | 50843.46 |
| 2 | 1033.56 | 2703.13 |
| 3 | 1044.55 | 1646.67 |
| 4 | 1074.56 | 2661.98 |
| 5 | 1078.56 | 13005.95 |
| 6 | 1118.55 | 3156.02 |
| 7 | 1126.65 | 3472.77 |
| 8 | 1179.65 | 1752.49 |
| 9 | 1208.74 | 2901.21 |
| 10 | 1210.76 | 9589.77 |
| 11 | 1231.78 | 2089.52 |
| 12 | 1234.68 | 6770.12 |
| 13 | 1254.76 | 130596.74 |
| 14 | 1260.75 | 2464.65 |
| 15 | 1275.78 | 178815.66 |
| 16 | 1279.76 | 1859.19 |
| 17 | 1293.70 | 3749.91 |
| 18 | 1308.71 | 1859.32 |
| 19 | 1315.74 | 5299.92 |
| 20 | 1320.64 | 3175.49 |
| 21 | 1349.70 | 6692.36 |
| 22 | 1434.84 | 1473.61 |
| 23 | 1475.82 | 4269.13 |
| 24 | 1493.80 | 2938.58 |
| 25 | 1526.84 | 13178.06 |
| 26 | 1538.84 | 3921.98 |
| 27 | 1542.83 | 3212.21 |
| 28 | 1554.85 | 2676.44 |
| 29 | 1573.80 | 2077.29 |
| 30 | 1599.87 | 2777.20 |
| 31 | 1639.78 | 1360.55 |
| 32 | 1700.92 | 2838.91 |
| 33 | 1722.91 | 17508.64 |
| 34 | 1736.86 | 1608.93 |
| 35 | 1753.97 | 1432.72 |
| 36 | 1813.00 | 1890.69 |
| 37 | 1826.96 | 2585.75 |
| 38 | 1830.03 | 7243.12 |
| 39 | 1837.97 | 10582.00 |
| 40 | 1849.95 | 17521.04 |
| 41 | 1911.03 | 2400.38 |
| 42 | 1936.98 | 6510.56 |
| 43 | 1955.05 | 1325.40 |
| 44 | 1998.12 | 2783.94 |
| 45 | 2039.65 | 4259.79 |
| 46 | 2079.14 | 62184.58 |
| 47 | 2085.15 | 1201.01 |
| 48 | 2095.13 | 9613.80 |
| 49 | 2150.15 | 2518.35 |
| 50 | 2163.13 | 3361.57 |
| 51 | 2272.16 | 13436.04 |
| 52 | 2294.14 | 897.53 |
| 53 | 2326.30 | 1187.02 |
| 54 | 2345.18 | 1417.40 |
| 55 | 2387.22 | 1715.26 |
| 56 | 2464.28 | 2647.65 |
| 57 | 2562.43 | 546.82 |
| 58 | 2669.34 | 1409.68 |
| 59 | 2687.35 | 1054.55 |
| 60 | 2706.46 | 3530.63 |

TABLE 8-continued

Mass spectrometry analysis of the immunoprecipitated 90 kDa protein.

| | m/z | Intens. |
|---|---|---|
| 61 | 2764.51 | 682.48 |
| 62 | 2771.42 | 832.80 |
| 63 | 2843.46 | 1059.69 |
| 64 | 2873.38 | 3997.29 |
| 65 | 2889.36 | 558.77 |
| 66 | 3029.49 | 648.16 |
| 67 | 3570.92 | 306.74 |
| 68 | 3958.23 | 362.16 |
| 69 | 4087.37 | 124.00 |
| 70 | 4273.48 | 78.00 |

Example 5

Characterization of Epitopes of Select Gelsolin Binding Agents of the Invention The epitope recognized by the anti-gelsolin antibodies of the invention was mapped to a 50-residue region of human gelsolin using the truncated gelsolin polypeptides of distinct but overlapping amino acid sequences of human gelsolin polypeptide.

1. Expression of Truncated Gelsolin Polypeptides

The epitopes recognized by GN3E9, GC1C10, and GF2D6 antibodies, as well as the commercially available anti-gelsolin GS2C4 antibody (Sigma Chemical Co., St. Louis, Mo., USA) were determined using a panel of the truncated recombinant human gelsolin proteins.

a. Design of Truncated Human Gelsolin Proteins

Total RNA was isolated from a HELA human cancer cell line. cDNA was synthesized using a reverse transcription kit (Promega, Madison, Wis., cat. no. A3500), according to the manufacturer's instructions. The cDNA was used as a template for PCR. The primers used for obtaining the cDNA clones encoding the truncated gelsolin proteins and the corresponding amino acid sequences of the truncated proteins are summarized in Table 9.

TABLE 9

Cloning of the truncated human gelsolin for epitope mapping

| Peptide | Primers | SEQ ID NO.: | Protein sequence | Epitope |
|---|---|---|---|---|
| GN1 | 5' CACCGGATCCCTGCTTTGCGCGCTGTCCCTG<br>3' GGATCCCTATCCATATGTGGCAGGGTC | SEQ ID NO.: 11<br>SEQ ID NO.: 12 | aa13-aa466 | aa416-aa466 |
| GN2 | 5' CACCGGATCCCTGCTTTGCGCGCTGTCCCTG<br>3' GGATCCCTAGTTGGCGATATGGCTGGA | SEQ ID NO.: 13<br>SEQ ID NO.: 14 | aa13-aa416 | aa366-aa416 |
| GN3 | 5' CACCGGATCCCTGCTTTGCGCGCTGTCCCTG<br>3' GGATCCCTAGATGAAGTCAGAGGCTGT | SEQ ID NO.: 15<br>SEQ ID NO.: 16 | aa13-aa366 | aa316-aa366 |
| GN4 | 5' CACCGGATCCCTGCTTTGCGCGCTGTCCCTG<br>3' GGATCCCTAAGCCACGAGGGAGACGG | SEQ ID NO.: 17<br>SEQ ID NO.: 18 | aa13-aa316 | aa266-aa316 |
| GN5 | 5' CACCGGATCCCTGCTTTGCGCGCTGTCCCTG<br>3' GGATCCCTACTCAGTGCCCTCCTCAGA | SEQ ID NO.: 19<br>SEQ ID NO.: 20 | aa13-aa266 | aa216-aa266 |
| GN6 | 5' CACCGGATCCCTGCTTTGCGCGCTGTCCCTG<br>3' GGATCCCTAGAAGCAGTCGCCATTGTT | SEQ ID NO.: 21<br>SEQ ID NO.: 22 | aa13-aa216 | aa166-aa216 |
| GN7 | 5' CACCGGATCCCTGCTTTGCGCGCTGTCCCTG<br>3' GGATCCCTACTTCAGGCCAGACTTGAA | SEQ ID NO.: 23<br>SEQ ID NO.: 24 | aa13-aa166 | aa116-aa166 |
| GN8 | 5' CACCGGATCCCTGCTTTGCGCGCTGTCCCTG<br>3' GGATCCCTACAGCCAGTAGTGGAGGTC | SEQ ID NO.: 25<br>SEQ ID NO.: 26 | aa13-aa116 | aa66-aa116 |
| GC1 | 5' CACCGGATCCGCCACATATGGACAGTTCT<br>3' GGATCCCTATCAGGCAGCCAGCTCAGC | SEQ ID NO.: 27<br>SEQ ID NO.: 28 | aa467-aa782 | aa732-aa782 |
| GC2 | 5' CACCGGATCCGCCACATATGGACAGTTCT<br>3' GGATCCCTACGTCTCGATGTACCGCTT | SEQ ID NO.: 29<br>SEQ ID NO.: 30 | aa467-aa732 | aa682-aa732 |
| GC3 | 5' CACCGGATCCGCCACATATGGACAGTTCT<br>3' GGATCCCTACTCTTCGATCACAAAACG | SEQ ID NO.: 31<br>SEQ ID NO.: 32 | aa467-aa682 | aa632-aa682 |
| GC4 | 5' CACCGGATCCGCCACATATGGACAGTTCT<br>3' GGATCCCTATGCCACCTGCACAGGTTG | SEQ ID NO.: 33<br>SEQ ID NO.: 34 | aa467-aa632 | aa582-aa632 |
| GC5 | 5' CACCGGATCCGCCACATATGGACAGTTCT<br>3' GGATCCCTAAGGCAATACCTCAACAGC | SEQ ID NO.: 35<br>SEQ ID NO.: 36 | aa467-aa582 | aa532-aa582 | b. PCR Reaction

DNA encoding each human gelsolin peptide summarized in Table 5, Table 6 or Table 9 was amplified from a composition comprising human nucleic acid as template. Briefly, the following reagents were combined in the PCR reaction (100 μA final volume): template cDNA, 5 μl of total 33 μl reaction; 10 pmol of the appropriate 5' and 3' primer pair (see Table 5 or Table 9); 10×PCR buffer, 10 μl; dNTPs (2.5 mM each), 4 μl; and Taq polymerase (Promega), 5 units.

The PCR reaction was conducted as follows. The solution was first heated at 94° C. for 2 min, followed by 40 cycles of 94° C. for 30 s, 52° C. for 1 min, and 72° C. for 3 min. The reaction was then incubated at 72° C. for 10 min for a final extension. The amplified DNA fragments were separated on a 1% agarose gel containing 0.25 μg/ml ethidium bromide and visualized using IN light. The bands corresponding to the expected size of the amplification product were recovered using the Gene Clean kit (BIO101, Irvine, Calif.). The identity of all PCR products was confirmed by sequence analysis (see below).

c. Cloning of PCR Products Encoding Truncated Human Gelsolin Polypeptide

Each DNA fragment encoding truncated human gelsolin polypeptide (Table 5, Table 6 and Table 9) was cloned using the TOPO Expression Cloning Kit (Invitrogen, CA). Briefly, the DNA fragment recovered from the PCR reaction solution, together with 50 ng of TOPO expression vector (TOPO Expression Cloning kit), was mixed with 1 μl of 10× ligase reaction buffer (6 mM Tris-HCl, pH 7.5, 6 mM magnesium chloride, 5 mM sodium chloride, 7 mM β-mercaptoethanol, 0.1 mM ATP, 2 mM DTT, 1 mM spermidine, and 0.1 mg/ml BSA), to which 4 units of T4 DNA ligase (1 μl) had been added. The total volume of the mixture was adjusted to 10 μl with sterile deionized water, and the resulting ligase solution was incubated at 14° C. for 15 h. Following incubation, 2 μl of the ligase reaction solution was added to 50 p. 1 of competent E. coli strain TOP10F (TOPO Expression Cloning Kit) and brought to competence in accordance with the manufacturer's instructions. The resulting mixture was kept on ice for 30 min, then treated at 42° C. for 30 s, and then again chilled on ice for 5 min. Next, 500 μl of medium containing 2% (v/v) tryptone, 0.5% (w/v) yeast extract, 0.05% (w/v) sodium chloride, 2.5 mM potassium chloride, 1 mM magnesium chloride, and 20 mM glucose (hereinafter referred to as "SOC" medium) was added to the culture, and the mixture was incubated for 1 h at 37° C. with shaking. After this time, the culture was spread on an L-broth agar plate (1% (v/v) tryptone, 0.5% (w/v) yeast extract, 0.5% (w/v) sodium chloride, 0.1% (w/v) glucose, and 0.6% (w/v) bacto-agar (Difco, Detroit, Mich.)), containing 100 μg/ml ampicillin. Ampicillin resistant colonies appearing on the plate were selected and scraped off with a platinum transfer loop and cultured in L-broth medium containing 100 μg/ml ampicillin at 37° C., overnight, with shaking at 200 r.p.m. After incubation, the cells were harvested by centrifugation, from which plasmid DNA was prepared by the alkali method (Sambrook et al., *Molecular Cloning: A Laboratory Manual*, Second Ed. (Cold Spring Harbor Laboratory Press, Cold Spring Harbor, N.Y., 1989)). Five clones from each truncated clone were sequenced to identify clones encoding predicted polypeptide sequence of each truncated gelsolin polypeptide. A single clone verified to encode the predicted polypeptide sequence of each truncated gelsolin polypeptide was then selected for expression in E. coli expression host.

d. Expression and Purification of Gelsolin Proteins

The cDNA encoding the full-length, the N-terminal or the C-terminal fragment of human gelsolin (Table 5 or Table 6) or the gelsolin polypeptide truncations shown in (Table 9) were each inserted into separate TOPO100 vectors (Invitrogen). The resulting plasmids were transformed into the *Escherichia coli* strain BL21 (DE3), which was grown in LB media to exponential phase and induced with 0.4 mM isopropyl-1-thio-β-D-galactopyranoside for 3 h. Cells were pelleted by centrifugation and the supernatant removed. The pelleted cells were resuspended in lysis buffer (8 M urea, 20 mM Tris-HCl), and further disrupted by sonication. This mixture was clarified by centrifugation (14,000×g for 15 min) and the supernatant recovered. The expressed recombinant human gelsolin polypeptide was purified from the clarified supernatant using a Ni-NTA superflow column (Qiagen, Valencia, Calif.) according to manufacturer's instructions. The purified gelsolin protein preparation was dialyzed against PBS at 4° C. overnight. The protein concentration was determined by BCA assay (Pierce, Woburn, Mass.), and aliquots were stored at −80° C. until use.

2. Epitope Mapping by ELISA with Truncated Human Gelsolin Proteins.

An ELISA plate (96 well; BD Biosciences, CA) was coated (4° C. overnight) with 1 μg/ml of each truncated gelsolin protein as listed in Tables 10 and 11. Unbound truncated gelsolin polypeptide was rinsed from the plate by washing the wells three times with PBS. The plate was then blocked with 3% (w/v) BSA PBS at room temperature for 1 h. Test antibody (at 1 μg/mL final concentration) was added to appropriate wells and incubated at 37° C. for 1 h. The unbound antibodies were removed from the wells by washing the plate three times with PBS. Bound anti-gelsolin antibody was detected by incubating wells (30 min; 37° C.) with HRP-conjugated anti-mouse IgG antibody (diluted 1:10,000; SouthernBiotech, Birmingham, Ala.)). Unbound HRP-conjugated anti-mouse IgG antibody was removed by rinsing the wells three times with PBS (5 min each). Anti-gelsolin antibody-HRP-conjugated anti-mouse IgG antibody complexes were measured using SureBlue TMB 1-Component Microwell Peroxidase Substrate (KPL, Gaithersburg, Md.). Specifically, SureBlue TMB 1-Component Microwell Peroxidase Substrate (KPL, Gaithersburg, Md.) was added to the wells and the plate was incubated for 10 min to allow HRP-mediated conversion of the substrate. The enzymatic reaction was stopped with the addition of 100 μl 2N $H_2SO_4$. The optical density of the sample wells was then measured at 450 nm/650 nm using an ELISA plate reader.

A total of 9 anti-gelsolin antibody clones which produce monoclonal antibody directed against the N-terminal fragment of human gelsolin were examined with a panel of the N-terminal human gelsolin truncated polypeptides (GN1-GN8). Similarly, 16 anti-gelsolin antibody clones which produce monoclonal antibody directed against the C-terminal fragment of human gelsolin were examined with a panel of the C-terminal human gelsolin truncated polypeptides (GC1-GC6). The epitope frequency of the N-terminal and C-terminal specific antibodies is shown in Tables 10 and 11, respectively.

TABLE 10

Epitope frequency of the N-terminus specific anti-gelsolin antibodies.

| Peptide | Sequence | Epitope | Frequency | Representative |
|---|---|---|---|---|
| GN1 | aa13-aa466 | aa416-aa466 | 0/9 | |
| GN2 | aa13-aa416 | aa366-aa416 | 0/9 | |
| GN3 | aa13-aa366 | aa316-aa366 | 4/9 | GN3E9 |
| GN4 | aa13-aa316 | aa266-aa316 | 0/9 | |

TABLE 10-continued

Epitope frequency of the N-terminus specific anti-gelsolin antibodies.

| Peptide | Sequence | Epitope | Frequency | Representative |
|---|---|---|---|---|
| GN5 | aa13-aa266 | aa216-aa266 | 0/9 | |
| GN6 | aa13-aa216 | aa166-aa216 | 0/9 | |
| GN7 | aa13-aa166 | aa116-aa166 | 0/9 | |
| GN8 | aa13-aa116 | aa66-aa116 | 5/9 | GF5A3 |

As shown in Table 10, four (4) of the nine (9) tested anti-gelsolin antibody clones which produce monoclonal antibody directed against the N-terminal fragment of human gelsolin were directed to region GN3. One such anti-human gelsolin antibody is GN3E9. The remaining five (5) of the nine (9) tested anti-gelsolin antibody clones which produce monoclonal antibody directed against the N-terminal fragment of human gelsolin were directed to region GN8. One such anti-human gelsolin antibody is GN5A3.

TABLE 11

Epitope frequency of the C-terminus specific anti-gelsolin antibodies.

| Peptide | Sequence | Epitope | Frequency | Representative |
|---|---|---|---|---|
| GC1 | aa467-aa782 | aa732-aa782 | 0/16 | |
| GC2 | aa467-aa732 | aa682-aa732 | 0/16 | |
| GC3 | aa467-aa682 | aa632-aa682 | 11/16 | GC1C10, GP2D6 Sigma GS2C4 |
| GC4 | aa467-aa632 | aa582-aa632 | 0/16 | |
| GC5 | aa467-aa582 | aa532-aa582 | 0/16 | |
| GC6 | aa467-aa532 | aa482-aa532 | 5/16 | GC5C1 |

As shown in Table 11, eleven (11) of the sixteen (16) tested anti-gelsolin antibody commercially available GS2C4 antibody clones which produce monoclonal antibody directed against the C-terminal fragment of human gelsolin were directed to region GC3. Three such anti-human gelsolin antibodies are GC1C10, GF2D6 and the commercially available GS2C4 antibody. The remaining five (5) of the sixteen (16) tested anti-gelsolin antibody clones which produce monoclonal antibody directed against the C-terminal fragment of human gelsolin were directed to region GC6. One such anti-human gelsolin antibody is GC5C1.

3. Fine Mapping of Epitopes by Analysis of Cross-Reactivity and Homology Among Species The high level of homology of gelsolin polypeptides among different species allowed further mapping of the gelsolin epitopes bound by gelsolin binding agents of the invention by examining cross-reactivity of these binding agents with gelsolin immunoreactive polypeptide expressed in different species.

a. Immunoprecipitation

Figure 5C:
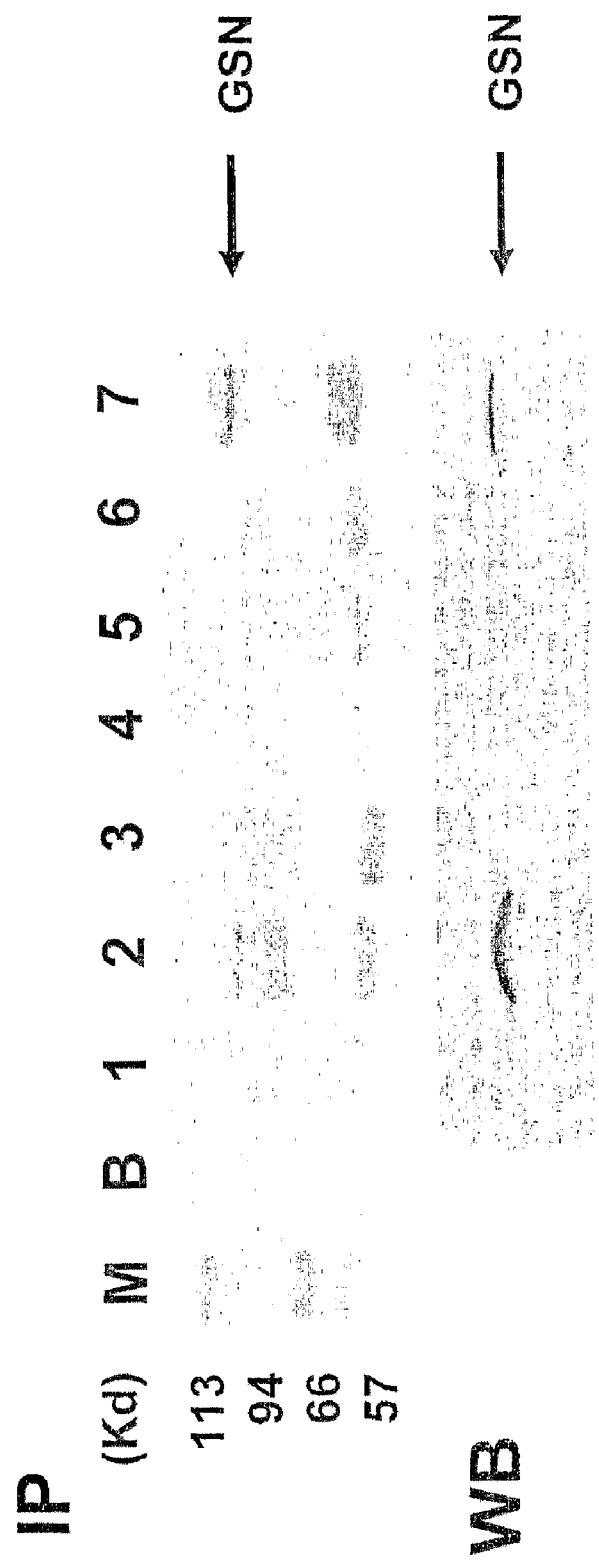
FIG. 5 is an analysis of the cross-reactivity of anti-gelsolin antibodies, GC 1C10 (FIG. 5A); GF2D6 (FIG. 5B) and GN3E9 (FIG. 5C) by immunoprecipitation (top panel) and western blot analysis (lower panel) among seven different species: lane 1: mouse; lane 2: monkey; lane 3: rabbit; lane 4: rat; lane 5: bovine; lane 6: horse; lane 7: human.

To determine the ability of anti-gelsolin antibodies of the invention to immunoprecipitate the native form of plasma gelsolin from various species, GN3E9, GF2D6 and GC1C10 were conjugated to Sepharose 4B at a concentration of 2 mg/ml beads as described in Example 3 above. One mL serum samples (1 mL) from select mammalian species were incubated with 10 µl antibody-conjugated beads or blank beads (control) at room temperature for 2 h. Unbound material was rinsed from the anti-gelsolin antibody-conjugated beads or blank beads by pelleting the bead by centrifugation (14,000 rpm, 3 min), removing the supernatant and then washing the pelleted beads by resuspension in PBS. Following five (5) wash cycles, materials bound to the anti-gelsolin antibody-conjugated beads or blank beads was removed under denaturing conditions by adding 40 µl SDS-PAGE loading buffer (SDS-PAGE loading buffer prepared by mixing 3× stock: 1M Tris-Cl pH 6.8 2.4 ml; 20% SDS 3 ml; Glycerol (100%) 3 ml; B-mercaptoethanol 1.6 ml; Bromophenol blue 0.006 g, 10 ml) to the pelleted beads and boiling the sample for 5 min. The immunoprecipitated proteins were fractionated on a 10% SDS-PAGE and visualized stained with Coomassie blue stain using standard techniques. Results are shown in FIG. 5A-5C.

b. Western Blot Analysis

To determine the binding specificity among different species of anti-gelsolin antibodies, western blot analysis of serum samples with anti-gelsolin antibodies was performed. The serum samples of select mammalian species (20 µl of 1:20 dilution of serum in PBS) were fractionated by 10% SDS-PAGE and western blotted onto nitrocellulose membrane using standard techniques. After electrotransfer the with electroblotted nitrocellulose membrane (blot) was blocked using 5% (w/v) non-fat milk at room temperature for 1 h. Blots was probed with a purified anti-gelsolin antibody (1 µg/ml; Protein A or protein G purified), i.e., GN3E9; GC1C10; GF2D6; or GS 2C4, at room temperature for 2 h. Unbound anti-gelsolin antibody was rinsed from the blots by washing five (5) times with PBS containing 0.02% (v/v) Tween 20 at room temperature for 10 min with shaking. The bound anti-gelsolin antibody was detected by probing each blot with HRP-conjugated goat anti-murine IgG (1:10,000 in blocking buffer) at room temperature for 1 h. Unbound HRP-conjugated goat anti-murine IgG was rinsed from the blots by washing five (5) times with PBS containing 0.02% (v/v) Tween 20 at room temperature for 10 min with shaking. The anti-gelsolin-HRP-conjugated goat anti-murine IgG complexes were visualized using BRP-mediated chemiluminescence. Specifically, the blots were incubated with Lumi-GLO® Peroxidase Chemiluminescent Substrate (KPL, Gaithersburg, Md.) for 3 min, and exposed to X-ray films. Results of western blot analysis are shown in FIG. 5A (GC1C10), FIG. 5B (GF2D6) and FIG. 5C (GN3E9). The lanes were as follows: M: molecular weight marker; B: blank; lane 1: mouse serum, lane 2: monkey serum, lane 3: rabbit serum, lane 4: rat serum, lane 5: bovine serum, lane 6: horse serum, lane 7: human serum.

The results of studies examining crossreactivity of anti-gelsolin antibodies are summarized in Table 12, where "nd" is not determined.

TABLE 12

Crossreactivity of Antibodies

| | pGSN | | | | | | | |
|---|---|---|---|---|---|---|---|---|
| Clone | human | monkey | bovine | horse | pig | rabbit | rat | mouse |
| GN3E9 | + | + | − | − | nd | − | − | − |
| GC1C10 | + | + | + | + | nd | − | + | − |
| GF2D6 | + | + | + | + | nd | − | − | − |
| GS2C4 | + | nd | + | nd | + | + | − | − |

As shown in Table 12, each anti-gelsolin antibody tested had a distinct pattern of crossreactivity for immunoreactive gelsolin. For example, antibody GN3E9 selectively bound primate serum gelsolin (human and monkey), but not serum gelsolin polypeptide of the other mammals tested. In contrast, commercial anti-gelsolin antibody GS2C4 was observed to bind to most of the mammalian serum gelsolin tested, except for rat and mouse.

c. Sequence Homology Analysis of Epitopes.

Differences in the sequence alignment of 50 amino acid gelsolin epitope regions (identified above) for various mammalian species examined for cross-reactivity with the human anti-gelsolin antibodies (see Table 12) allowed for further refinement of the gelsolin epitopes to approximately 10 amino acid residues for each of the anti-gelsolin antibodies tested. The results of homology search and epitope determination are summarized in Table 13 (GN3E9), Table 14 (GF2D6), Table 15 (GC1C10) and Table 16 (Sigma GS2C4). It was observed that one or two amino acid residue changes in the gelsolin epitope regions may affect epitope binding of anti-gelsolin antibody.

TABLE 13

Homology search and epitope determination of GN3E9

| Species | Sequence homology | Reactivity | Determined epitope | amino acid range | Seq ID |
|---|---|---|---|---|---|
| Human | FAQGALKSED | ++++ | FAQGALKSED | 321-330 | SEQ ID NO.: 2 |
| Bovine | FAQGALRSED | − | | | SEQ ID NO.: 37 |
| Horse | FAQGALRSED | − | | | SEQ ID NO.: 37 |
| Mouse | FAQGALRSED | − | | | SEQ ID NO.: 37 |
| Rat | FAQGALRSED | − | | | SEQ ID NO.: 37 |

As summarized in Table 13, the anti-gelsolin antibody GN3E9 is predicted to bind an epitope comprising the amino acid sequence FAQGALKSED (SEQ ID NO.: 2).

TABLE 14

Homology search and epitope determination of GF2D6

| Species | Sequence homology | Reactivity | Determined epitope | amino acid range | Seq ID |
|---|---|---|---|---|---|
| Human | ACSNKIGRFV | ++++ | ACSNKIGRFV | 661-670 | SEQ ID NO.: 4 |
| Bovine | ACSNKIGRFV | ++++ | | | SEQ ID NO.: 4 |
| Horse | ACSNKIGRFV | ++++ | | | SEQ ID NO.: 4 |
| Mouse | ACSNRIGRFV | − | | | SEQ ID NO.: 38 |
| Rat | ACSNRIGRFV | − | | | SEQ ID NO.: 38 |
| pig | ACSNKIGRFV | nd | | | SEQ ID NO.: 4 |

As summarized in Table 14, the anti-gelsolin antibody GF2D6 is predicted to bind an epitope comprising the amino acid sequence ACSNKIGRFV (SEQ ID NO.: 4).

TABLE 15

Homology search and epitope determination of GC1C10

| Species | Sequence homology | Reactivity | Determined epitope | amino acid range | Seq ID |
|---|---|---|---|---|---|
| Human | SEPDGFWEAL | ++++ | SEPDGFWEAL | 636-645 | SEQ ID NO.: 3 |
| Bovine | SEPDSFWEAL | ++++ | SEPDSFWEAL | 636-645 | SEQ ID NO.: 39 |
| Horse | SEPDSFWEAL | ++++ | | | SEQ ID NO.: 39 |
| Mouse | SEPDAFWEAL | − | | | SEQ ID NO.: 40 |

TABLE 15-continued

Homology search and epitope determination of GC1C10

| Species | Sequence homology | Reactivity | Determined amino acid epitope range | Seq ID |
|---|---|---|---|---|
| Rat | SEPDGFWEAL | ++++ | | SEQ ID NO.: 3 |
| Pig | SEPDSFWEAL | nd | | SEQ ID NO.: 39 |

As summarized in Table 15, the anti-gelsolin antibody GC1C10 is predicted to bind an epitope comprising the amino acid sequence SEPDXFWEAL (SEQ ID NO.: 47) wherein Xaa is G or S.

TABLE 16

Homology search and epitope determination of GS2C4

| Species | Sequence homology | Reactivity | Determined amino acid epitope range | Seq ID |
|---|---|---|---|---|
| Human | GGKAAYRTSP | ++++ | GGKAAYRTSP646-655 | SEQ ID NO.: 41 |
| Bovine | GGKAAYRTSP | ++++ | | SEQ ID NO.: 41 |
| Horse | GGKATYRTSP | − | | SEQ ID NO.: 42 |
| Mouse | GGKTAYRTSP | − | | SEQ ID NO.: 43 |
| Rat | GGKTAYRTSP | − | | SEQ ID NO.: 43 |
| pig | GGKAAYRTSP | ++++ | | SEQ ID NO, : 41 |

As summarized in Table 16, the commercial anti-gelsolin antibody GS2C4 is predicted to bind an epitope comprising the amino acid sequence GGKAAYRTSP (SEQ ID NO.:41).

Figure 6:
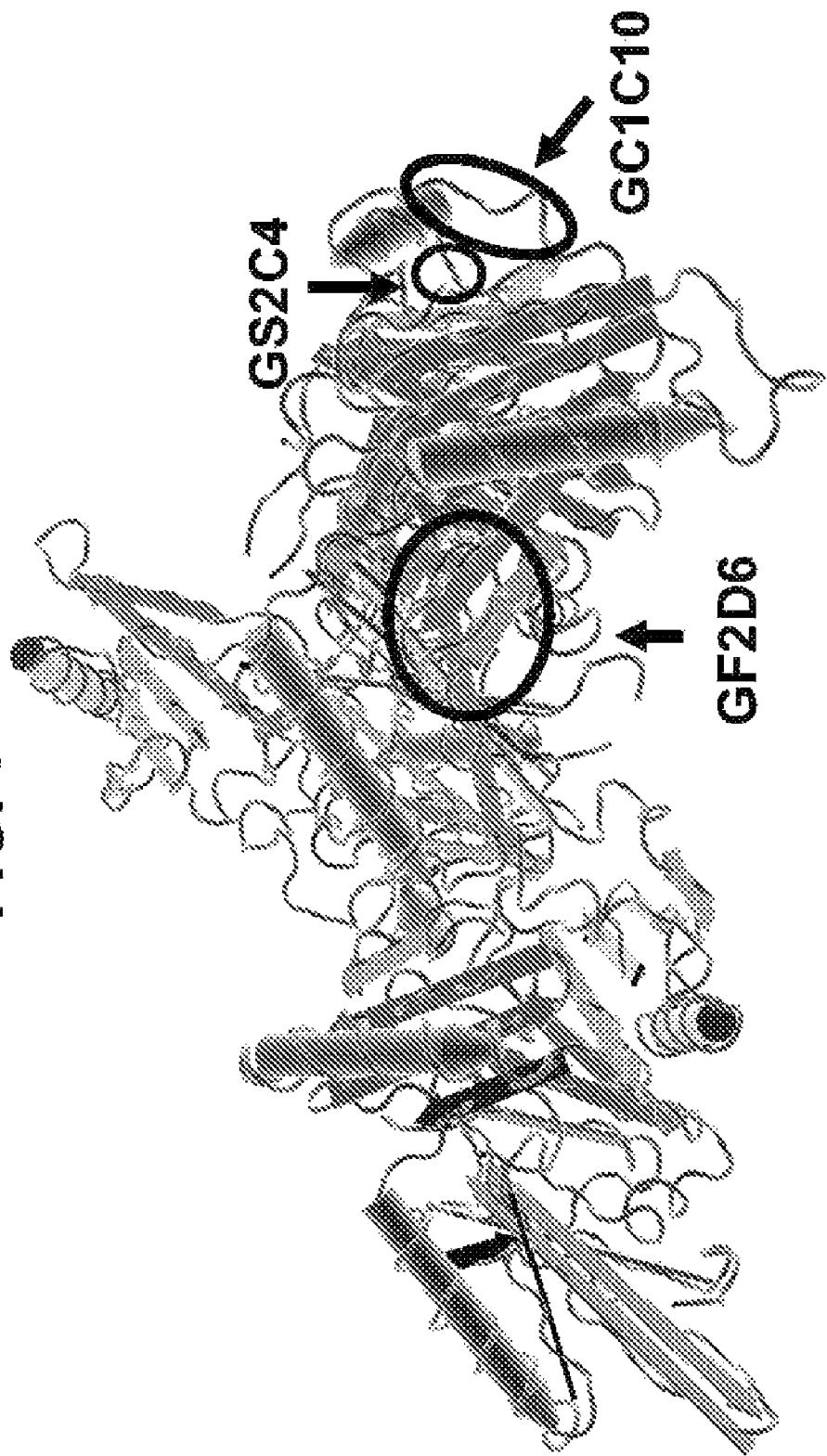
FIG. 6 is a 3D structure of the C-terminal fragment of gelsolin and the epitope location of anti-gelsolin antibodies.

As noted above, the anti-gelsolin antibodies GN3EP, GC1C10, GF2D6 and GS2C4 display distinct biochemical characteristics. Anti-gelsolin antibodies GN3EP, GC1C10, and GF2D6 show patterns of cross-reactivity which are distinct from one another and which also differ from the pattern of cross-reactivity observed for the commercial anti-gelsolin antibody GS2C4. Furthermore, the anti-gelsolin antibodies GN3EP, GC1C10, and GF2D6 bind to gelsolin epitopes which are distinct from one another and which also differ from the gelsolin epitope bound by the commercial anti-gelsolin antibody GS2C4. This is further illustrated by analysis of the 3D structure of the C-terminus of gelsolin (Narayan et al., FEBS Lett, 552: 82-85 (2003)). A shown in FIG. 6, mapping the location of the location of the gelsolin epitopes identified for anti-gelsolin antibodies GC1C10, GF2D6 and GS2C4 reveal that these agents bind to differing regions on the surface of human gelsolin polypeptide. The results indicate that the epitopes recognized by all the anti-gelsolin antibodies tested are in regions predicted to be positively charged.

Example 6

Capability of Recognizing Actin-Free Plasma Gelsolin

The ability of the gelsolin binding agents of the present invention to recognize the unbound (active) form of plasma gelsolin and not the bound (inactive) form of plasma gelsolin was tested using an actin inhibitory ELISA assay. In this assay, an ELISA plate was coated with 1 μg/ml of purified native human plasma gelsolin in PBS at 4° C. overnight. After washing three times with PBS, the plate was blocked with 3% (w/v) BSA PBS at room temperature for 1 h. F-actin was added to appropriate test wells to a final concentration of 10 μg/ml the presence of 10 mM $CaCl_2$. The plate was then incubated at incubated at 37° C. for 1 h to allow binding of actin to the native plasma gelsolin coating on the well. Following this incubation period, the unbound F-actin was rinsed from the wells by washing three times with PBS at room temperature (3 min each). Anti-gelsolin test antibody (at 1 μg/mL final concentration) was added to appropriate wells and incubated at 37° C. for 1 h. The unbound antibody was removed from the wells by washing the plate three times with PBS. Bound anti-gelsolin antibody was detected by incubating wells (30 min; 37° C.) with PRP-conjugated anti-mouse IgG antibody (diluted 1:10,000; SouthernBiotech, Birmingham, Ala.)). Unbound HRP-conjugated anti-mouse IgG antibody was removed by rinsing the wells three times with PBS (5 min each). Anti-gelsolin antibody-HRP-conjugated anti-mouse IgG antibody complexes were measured using SureBlue TMB 1-Component Microwell Peroxidase Substrate (KPL, Gaithersburg, Md.). Specifically, SureBlue TMB 1-Component Microwell Peroxidase Substrate (KPL, Gaithersburg, Md.) was added to the wells and the plate was incubated for 10 min to allow HRP-mediated conversion of the substrate. The enzymatic reaction was stopped with the addition of 100 μl 2N $H_2SO_4$. The optical density of the sample wells was then measured at 450 nm/650 nm using an ELISA plate reader.

Figure 7:
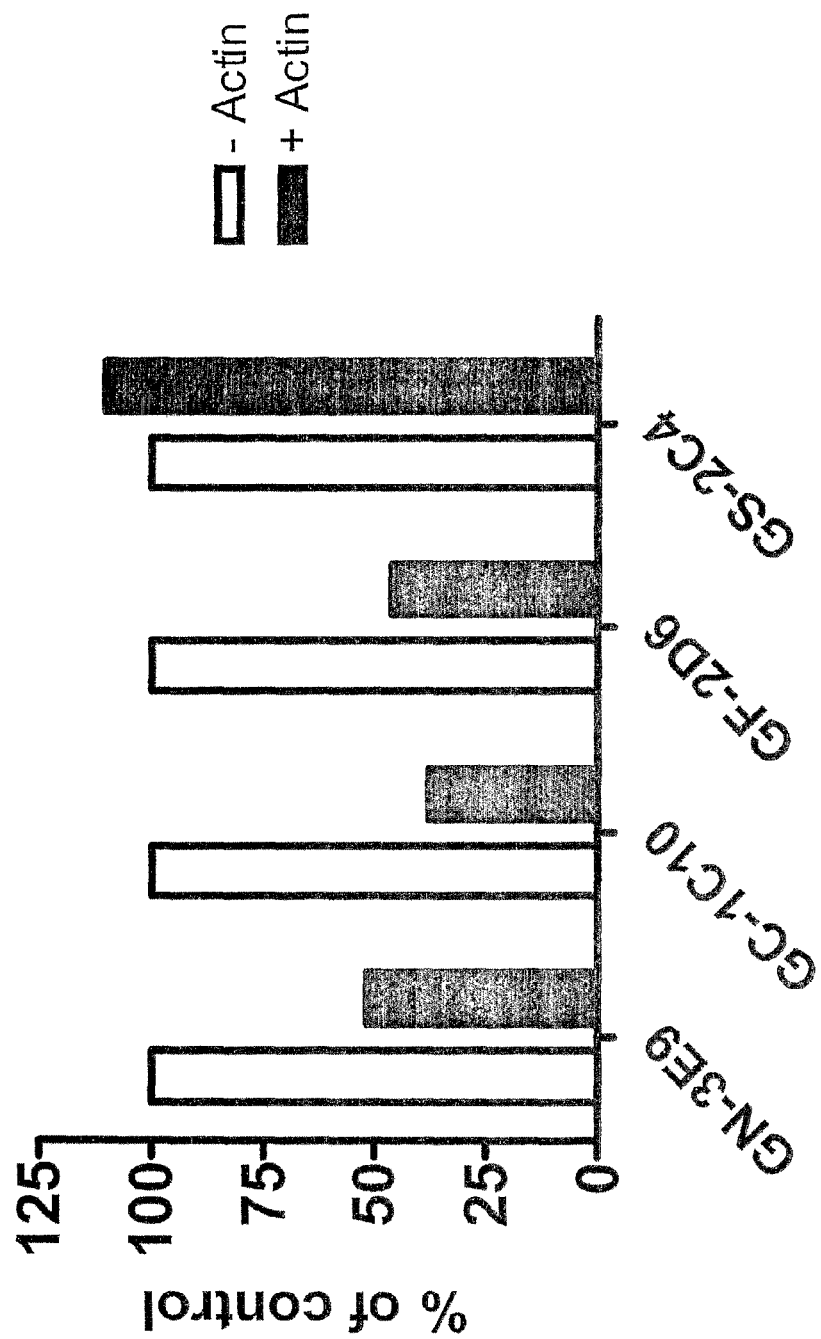
FIG. 7 is a F-actin inihibitory ELISA analysis of the binding of anti-gelsolin antibodies to purified human plasma gelsolin. The inhibition of antibody binding to gelsolin by F-actin is presented as percent of the binding without F-actin.

Comparison of the amount of anti-gelsolin antibody bound to the samples treated with F-actin relative to the binding of antibody to samples not treated with F-actin (100% binding) is summarized in FIG. 7. The commercial anti-gelsolin antibody GS2C4 did not discriminate between free gelsolin (i.e., not bound to F-actin) and F-actin-bound gelsolin as no significant change was observed in the assay signal observed for anti-gelsolin antibody GS2C4 binding in the presence or absence of F-actin treatment. In contrast, anti-gelsolin antibodies GN3E9, GC1C10, and GF2D6 show a preference for the active form of human plasma gelsolin over the actin-bound form of gelsolin (FIG. 7). While not wishing to be limited by theory, free and actin-complexed gelsolin molecules differ in their functional properties. For example, although free gelsolin can sever actin filaments, actin-gelsolin in complexes cannot. Accordingly, use of such gelsolin binding agents which preferentially bind free active gelsolin in methods of the present invention have the advantage of more accurately quantifying level of free gelsolin in a biological sample which (as noted above) has different functional properties than gelsolin complexed with actin.

Example 7

Immunoassay for Plasma Gelsolin

1. Methods

To develop a sandwich gelsolin ELISA for quantitative measurement of plasma gelsolin, four anti-gelsolin antibodies were selected to determine their ability to serve as a capture or detection antibody. Gelsolin ELISA was carried out as follows. An ELISA plate (96 well; BD biosciences CA) was coated with 10 μg/ml of the capture antibody at 4° C. overnight. Unbound capture antibody was rinsed from the wells by washing the plate three times with PBS. Non-specific binding sites were then blocked by incubating the wells with 3% (w/v) BSA in PBS (1 h, room temperature). Blocking solution was removed from the wells and the plate was air dried prior to vacuum sealing and storage at 4° C. prior to use. For measurement of gelsolin in biological sample, 50 μl of human plasma sample was first added to appropriate wells of gelsolin ELISA plate treated with capture antibody which had been equilibrated to room temperature. Immediately following the addition of the samples to the plate, 50 μl of HRP-conjugated detection antibody (~0.1 μg/ml in blocking buffer) was added to appropriate wells and the plate was incubated for 20 min at 37° C. Unbound material was rinsed from the wells by washing the plate three times with PBS. Captured plasma gelsolin: HRP-conjugated antibody complexes were measured by adding 100 μl ECL substrate buffer (KPL, Inc., Gaithersburg, Md.) was added. After incubation at 37° C. for 3 min, the optical density of each well was measured at 450 nm/650 nm in an ELISA plate reader.

2. Pairing Capability of Gelsolin Antibodies in ELISA

Table 17 shows the pairing compatibility of select antibodies of the present invention and the commercial anti-gelsolin monoclonal antibody GS2C4. When anti-gelsolin antibody GN3E9 was used as the capture antibody, the highest OD values were obtained with either GC1C10 or GF2D6 antibodies as a detection antibody, suggesting that a useful antibody configuration for gelsolin ELISA is GN3E9 as capture and GC1C10 antibody or GF2D6 antibody as detection antibody. In contrast, the gelsolin binding agents of the invention (e.g., anti-gelsolin antibodies GN3E9, GC1C10 or GF2D6), the commercial anti-gelsolin antibody GS2C4 was not useful as either a capture or detection antibody to detect plasma gelsolin in ELISA format.

TABLE 17

Pairing Capability of Gelsolin Antibodies in ELISA

| | | Capture Antibody | | | |
|---|---|---|---|---|---|
| | | GN3E9 | GC1C10 | GF2D6 | GS2C4 |
| Detection | GN3E9 | — | 2.58 | 2.96 | 0.015 |
| | GC1C10 | 3.65 | — | 0.35 | 0.012 |
| | GF2D6 | 3.85 | 0.41 | — | 0.031 |
| | GS2C4 | 0.025 | 0.014 | 0.013 | — |

3. Quantitative Measurement of Plasma Gelsolin

To test the ability of gelsolin binding agents of the invention to quantitatively measure plasma gelsolin in a gelsolin ELISA assay format (as detailed above), standard curves were generated using a dilution series of samples containing affinity-purified human plasma gelsolin. The results are shown in FIG. 8 and indicate that the two capture/detection antibody pairs tested are capable of quantitative measurement human gelsolin over a broad concentration range of plasma gelsolin. As shown in both FIG. 8A and FIG. 8B, there was a direct linear relationship between the assay signal expressed as relative light units (RLU) and the plasma gelsolin concentration (ng/ml). For example, the antibody pair shown in FIG. 8A (GN3E9 (capture)/GC1C10 (detection)) had an R value of 0.9998. The antibody pair shown in FIG. 8B (GN3E9 (capture)/GF2D6 (detection)) had an R value of 0.9989.

4. Effects of Sample Preparation on Measurement of Plasma Gelsolin

Figure 9:
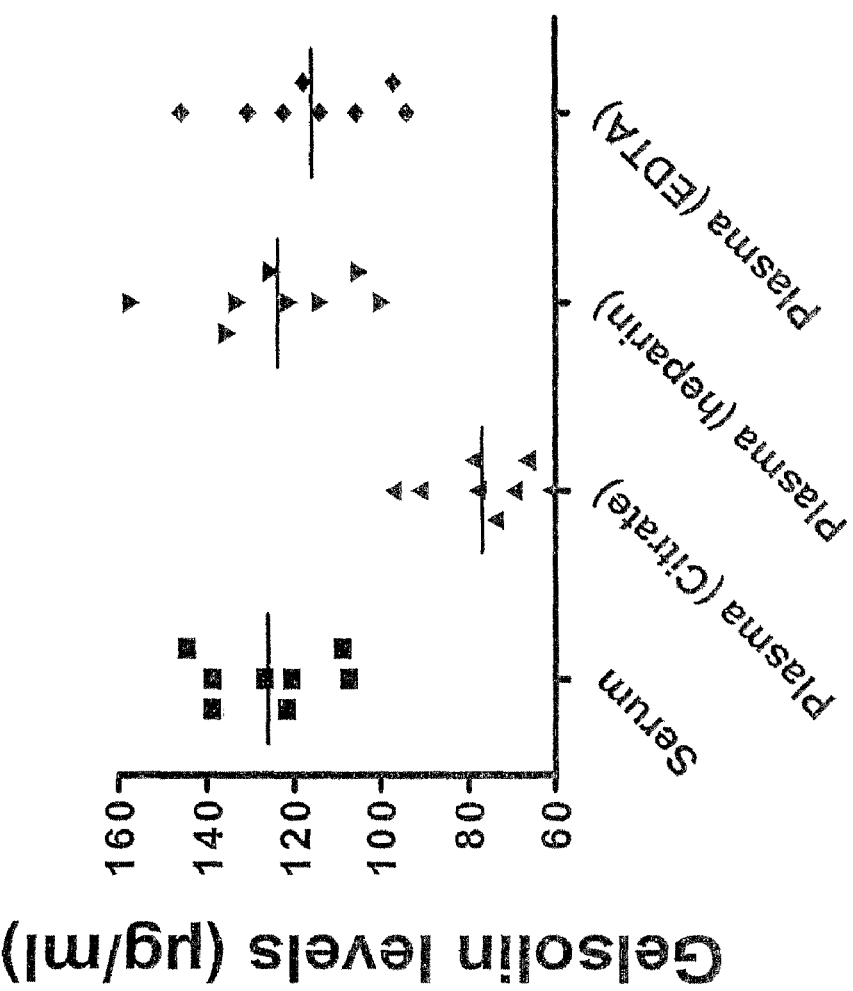
FIG. 9 is a comparison of quantification of plasma gelsolin levels based sample handling conditions, i.e. addition of sodium citrate (citrate), heparin, or EDTA to the sample.

To test whether blood collection procedure may affect the quantitation of gelsolin, blood samples from 8 healthy individuals were collected in the serum preparation tubes containing sodium citrate, herparin, or EDTA (Liu Yang Medical Device Co Ltd, Hunan, China) Gelsolin ELISA was conducted as described above using the GN3E9/GC1C10 antibody pair. The results are shown in FIG. 9. The no additive (serum) sample showed a gelsolin level of 126±14 μg/mL. Addition of heparin or EDTA did not significantly interfere with the quantitation of gelsolin in serum and showed gelsolin levels of 124±18 μg/mL and 116±17 μg/mL, respectively. However, sodium citrate does interfere with the ELISA measurement of human plasma gelsolin, showing 77±12 μg/mL gelsolin ($p<0.0001$). These results indicate that the conditions of preparation of plasma samples may affect detection of immunoreactive gelsolin polypeptides by ELISA techniques.

5. Specific Measurement of the Full-Length Gelsolin

Figure 10:
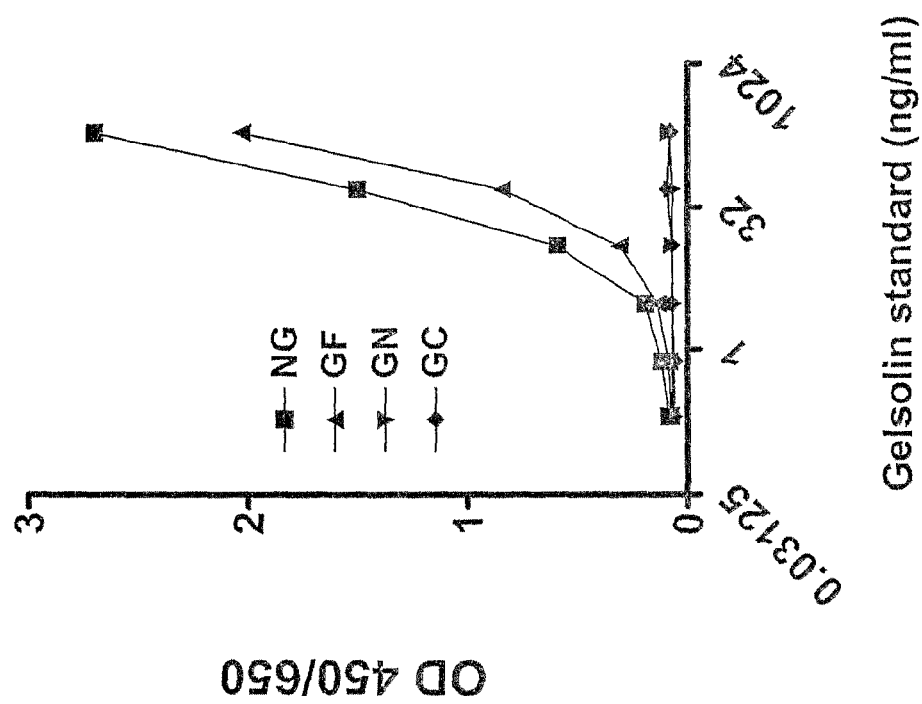
FIG. 10 shows a graph of optical density versus gelsolin polypeptide concentration in an ELISA assay using the antibody pair GN3E9/GC1C10, where the gelsolin polypeptide is NG: native gelsolin; GF: full-length recombinant gelsolin; GN: recombinant N-terminal gelsolin fragment; or GC: recombinant C-terminal gelsolin fragment.

To determine whether the immunoassay using gelsolin binding agents measures full-length gelsolin and/or other immunoreactive fragments, four different types of human gelsolin standards (e.g., native gelsolin, recombinant full-length, recombinant N-terminal and recombinant C-terminal fragments) were measured by ELISA using GN3E9/GC1C10 antibody pair. The results are shown in FIG. 10. The gelsolin binding agents tested were useful in a ELISA format to quantitatively measure both native plasma gelsolin and recombinant full-length gelsolin in a dose-dependent fashion. Consistent with the specificity of the GN3E9 capture antibody and the GC1C10 detection antibody this antibody pairing did detect either N-terminal or C-terminal fragment. These results indicate that the quantitative assay described in this example is specific for full-length gelsolin and does not detect immunoreactive fragments.

6. Specific Measurement of Actin-free Gelsolin

Figure 11A:
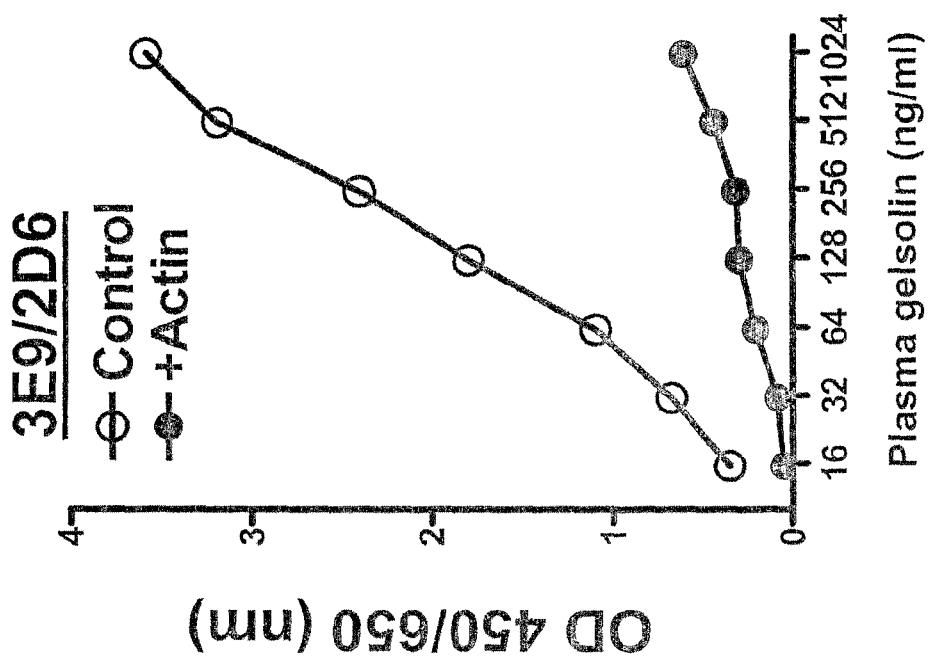
FIG. 11 shows a graph of optical density versus plasma gelsolin in an ELISA assay using the GN3E9/GC 1C10 (FIG. 11A) or GN3E9/GF2D6 (FIG. 11B) antibody pair to measure actin-free gelsolin (control) or gelsolin in complex with actin (+actin).
Figure 11B:
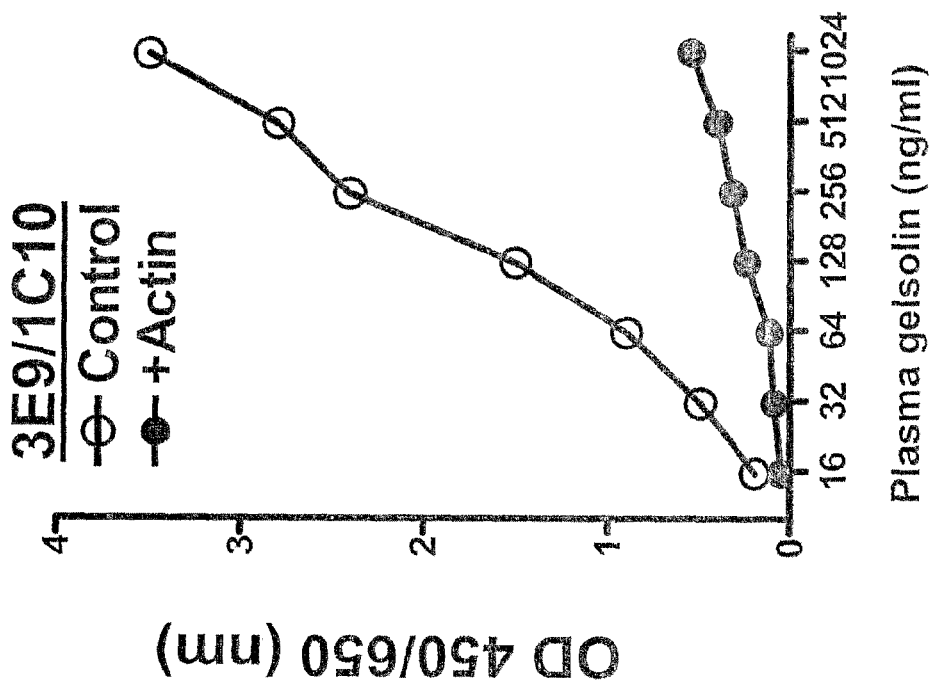

An immunoassay for plasma gelsolin that measures the functional form of gelsolin in samples, e.g. the actin-free form would be advantageous. To determine whether gelsolin ELISA using gelsolin binding agents of the invention only measures actin-free gelsolin, various amounts of native plasma gelsolin standard were measured in the presence or absence of 10 μg/ml F-actin using two pairs of antibodies. As shown in FIG. 11, the presence of F-actin significantly reduced the reactivity of the paired antibodies to gelsolin (Panel A: GN3F9/GC1C10; Panel B: GN3E9/GC2D6). These results indicate that the selected antibody pairs are useful to quantitate active plasma gelsolin in an ELISA format as they are selective for active plasma gelsolin.

Example 8

Quantitation of Plasma Gelsolin in Clinical Samples

1. Serum Gelsolin Levels in Critical Care Patients

Figure 12:
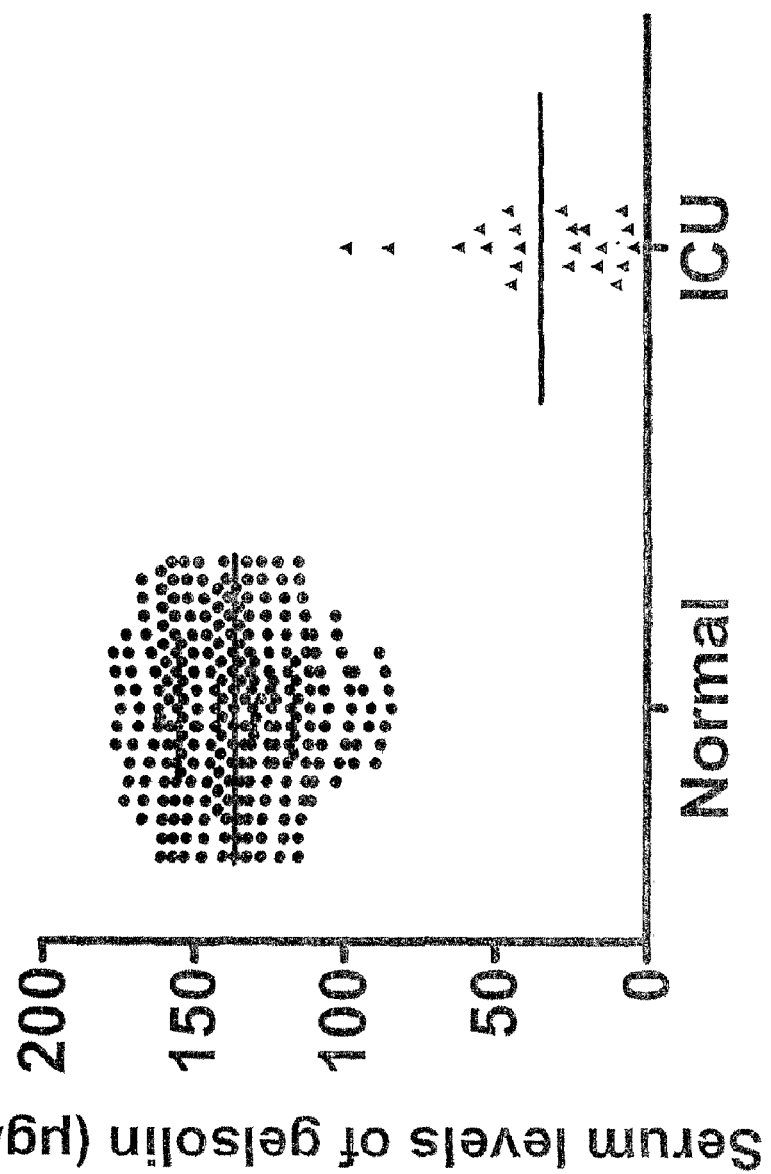
FIG. 12 is a graph of serum gelsolin concentration measured in healthy controls (n=291) and ICU (critical care) patients (n=22) using a gelsolin ELISA assay of the invention.

To test the ability of the gelsolin ELISA assay to quantitate gelsolin in a clinical setting, samples from normal patients and ICU patients were obtained and analyzed as described above. This analysis used the capture/detection antibody pair GN3E9/GC1C10. The results are shown in FIG. 12 and Table 18. FIG. 12 shows that normal subjects exhibited a serum gelsolin level of 136±22 µg/mL, while ICU patients had a significantly decreased serum gelsolin level of approximately 35±25 µg/mL (p<0.0001). Table 18 presents data showing the sex, age, diagnosis, and actual gelsolin level for each of the critical care patients. Thus, serum gelsolin level is a biomarker of septic shock, infection (e.g., pneumonia and respiratory distress syndrome); heart failure; heart attack and pancreatitis in ICU patients.

TABLE 18

Serum Gelsolin Levels in Critical Care Patients

| Sample No | Sex | Age | Diagnosis | Serum gelsolin (µg/ml) | Cut-off (mean − 3SD) |
|---|---|---|---|---|---|
| Normal control (298) | | | | 136 ± 22 | 70 |
| 1 | F | 70 | Stroke | 8.4 | **** |
| 2 | M | 80 | pneumonia | 99.5 | |
| 3 | M | 74 | Sepsis | 25.8 | *** |
| 4 | F | 70 | Pneumonia, RDS? | 4.6 | **** |
| 5 | F | 88 | Heart infarction | 16.8 | *** |
| 6 | F | 76 | Heart failure | 6.7 | **** |
| 7 | M | 72 | Pneumonia, RDS? | 15.2 | *** |
| 8 | M | 80 | Pneumonia, RDS? | 8.7 | **** |
| 9 | M | 80 | Pneumonia | 42.2 | ** |
| 10 | F | 82 | Pneumonia | 53.2 | * |
| 11 | M | 75 | Acute pancreatis | 85.4 | |
| 12 | M | 72 | ? | 25.1 | *** |
| 13 | | | | 46.1 | * |
| 14 | | | | 43.8 | * |
| 15 | | | | 23.7 | **** |
| 16 | | | | 43.3 | * |
| 17 | F | 87 | Pneumonia, RDS? | 21.1 | *** |
| 18 | M | 75 | Pneumonia | 10.3 | *** |
| 19 | M | 80 | Pneumonia | 62.3 | * |
| 20 | M | 78 | Sepsis | 28.1 | *** |
| 21 | M | 72 | Heart failure | 55.5 | * |
| 22 | F | 85 | Heart failure | 44.9 | * |

While the patients in the ICU group showed relatively advanced ages, other studies showed that plasma gelsolin levels among various age groups are not significantly different. The results are shown in Table 19.

TABLE 19

Quantitation of Serum Gelsolin In Human Subjects Classified by Age

| | Age Group | | | | | |
|---|---|---|---|---|---|---|
| | 20-30 | 30-40 | 40-50 | 50-60 | 60-70 | 70-80 |
| Number of subjects | 83 | 36 | 13 | 29 | 72 | 70 |
| Mean | 185.8 | 181.1 | 190.2 | 188.4 | 194.6 | 203.7 |
| Std. Deviation | 37.75 | 34.2 | 37.46 | 32.93 | 43.69 | 40.34 |
| Std. Error | 4.144 | 5.7 | 10.39 | 6.114 | 5.149 | 4.822 |

Two additional groups of critical care patients, patients having major surgery and those exhibiting symptoms of severe sepsis, also showed decreased levels of serum gelsolin using the gelsolin binding agents of the present invention in a gelsolin ELISA assay. Major surgery is defined as any surgical procedure that involves anesthesia or respiratory assistance. The criteria for patient recruitment was previously described (Wang et al., *Eur J Clin Pharmacol* 62:927-31 (2006)). Severe sepsis is defined as sepsis associated with new organ dysfunction, hypotension, or hypoperfusion. The criteria for patient recruitment was previously described (Chen et al., *Genes immun* 8:439-43 (2007)).

Compared to the control (127.7±35.2 µg/mL, n=14), serum gelsolin levels were reduced in both the surgery patients (44.75±25.0 µg/mL, n=43) and severe sepsis patients (21.65±12.04 µg/mL, n=80). These results further demonstrate the ability of the gelsolin binding agents of the present invention to quantify serum gelsolin in a clinical setting. Further, the studies demonstrate that gelsolin ELISA using gelsolin binding agents of the invention is useful to measure serum gelsolin in biological sample from sepsis patients. Gelsolin is a biomarker in human sepsis.

2. Serum Gelsolin Levels in Systemic Lupus Erythematosus (SLE)

Figure 13:
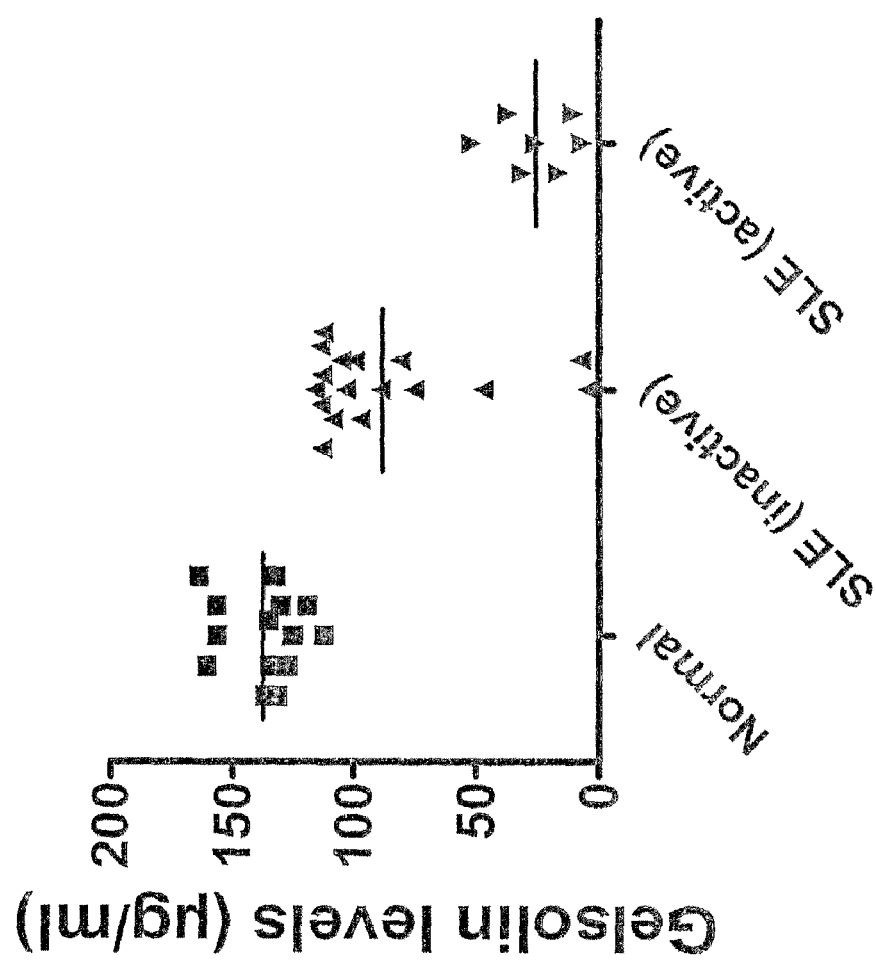
FIG. 13 is a graph of serum gelsolin concentration (μg/mL) in normal patients and patients exhibiting inactive and active forms of Systemic Lupus Erythematosus (SLE) as determined using a gelsolin ELISA assay of the invention.

Gelsolin ELISA using gelsolin binding agents of the invention was used to examine whether serum gelsolin level provides a suitable biomarker for the detection of an active autoimmune disease, such as systemic lupus erythematosus (SLE). The gelsolin ELISA analysis was carried out as described above. The results are shown in FIG. 13 and indicate that patients having active SLE (2616 µg/mL, p<0.0001) or inactive SLE (88±36 µg/mL, p<0.0001) show significantly decreased levels of serum gelsolin compared to normal patients (137±16 µg/mL). Likewise, patients having inactive SLE show significantly decreased levels of serum gelsolin compared to normal patients. Further, the studies demonstrate that gelsolin ELISA using gelsolin binding agents of the invention is useful to measure serum gelsolin in biological sample from patients with autoimmune disease. Serum gelsolin may be a biomarker for an autoimmune disease and may help to identify individuals moving from active to inactive SLE status.

3. Serum Gelsolin Levels in Chronic Hepatitis

Figure 14:
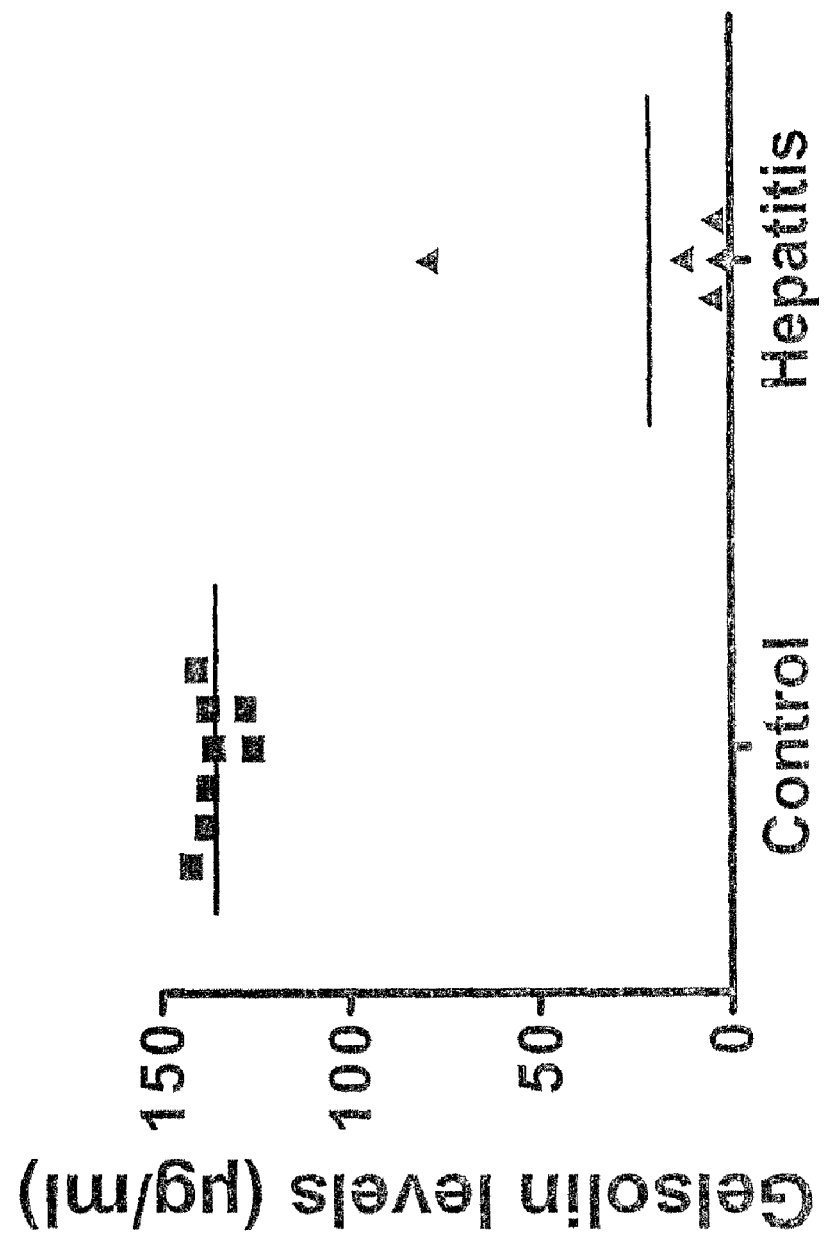
FIG. 14 is a graph of serum gelsolin concentration (μg/mL) in normal patients and patients with chronic hepatitis as determined using a gelsolin ELISA assay of the invention.

Gelsolin ELISA using gelsolin binding agents of the invention was used to examine whether serum gelsolin level provides a suitable biomarker for the detection of chronic hepatitis. The gelsolin ELISA analysis was carried out as described above. As shown FIG. 14, serum gelsolin is significantly decreased in patients with chronic hepatitis. Thus, gelsolin may be an indicator of liver function, and suggests that patients with chronic hepatitis may need gelsolin replacement therapy. Serum gelsolin may be a biomarker for chronic hepatitis. Further, the studies demonstrate that gelsolin ELISA using gelsolin binding agents of the invention is useful to measure serum gelsolin in biological sample from patients with chronic hepatitis.

4. Serum Gelsolin Levels in Rheumatoid Arthritis

Figure 23:
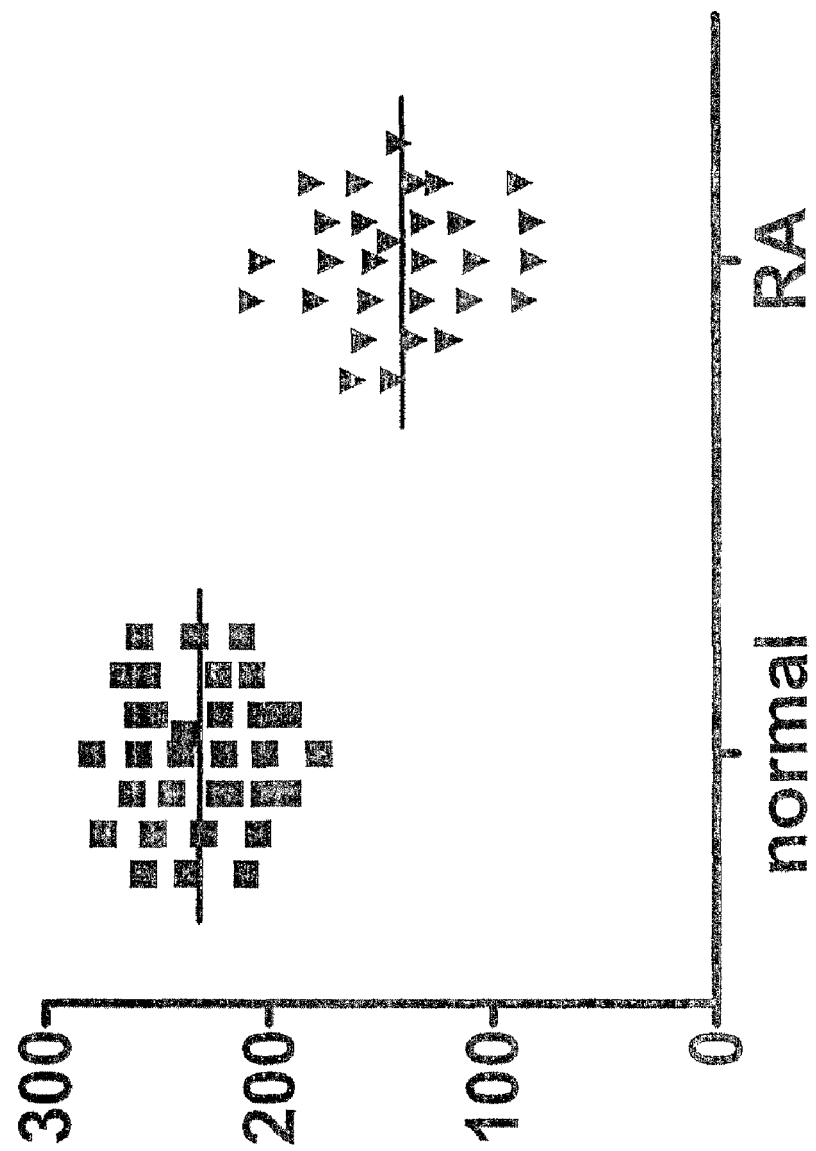
FIG. 23 is a graph of serum gelsolin concentration (μg/mL) in normal patients compared with patients with rheumatoid arthritis as determined using a gelsolin ELISA assay of the invention.

Gelsolin ELISA using gelsolin binding agents of the invention was used to examine whether serum gelsolin level provides a suitable biomarker for the detection of a chronic inflammatory disease, such as rheumatoid arthritis. The gelsolin ELISA analysis was carried out as described above. The results are shown in FIG. 23 and indicate that patients having rheumatoid arthritis (140.116.3 µg/mL, p<0.0001; n=29; mean±SEM) show significantly decreased levels of serum gelsolin compared to normal patients (231±4.7 µg/mL; n=32). The studies demonstrate that gelsolin ELISA using gelsolin binding agents of the invention is useful to measure serum gelsolin in biological sample from patients with chronic inflammatory disease, e.g., rheumatoid arthritis.

5. Serum Gelsolin Levels in Cancer Patients

Gelsolin ELISA using gelsolin binding agents of the invention was used to measure serum gelsolin levels in cancer patients in order to evaluate the patient's condition. Serum samples were collected from patients with newly diagnosed cancer prior to any major treatment (surgery, chemotherapy, or radiation therapy). The samples were analyzed by gelsolin ELISA as described above using the capture/detection antibody pair GN3EP/GC1C10. The results are shown in Table 20.

TABLE 20

Serum Gelsolin Levels in Cancer Patients

| | Number of samples | Below cut-off Mean − 3SD (70 μg/mL) | % of patients below cutoff value |
| --- | --- | --- | --- |
| Normal | 291 | 0 | 0 |
| Breast | 48 | 7 | 14.6% |
| Colon | 66 | 17 | 27.6% |
| Gastric | 98 | 40 | 40.8% |
| Lung | 88 | 42 | 47.7% |

The results indicate that a significant portion of patients having cancers of all the types tested exhibited a significantly lower serum gelsolin level compared to healthy controls. As such, serum gelsolin level may be a biomarker for cancer or the status of cancer patients. Further, the studies demonstrate that gelsolin ELISA using gelsolin binding agents of the invention is useful to measure serum gelsolin in biological sample from patients with cancer. The gelsolin ELISA using gelsolin binding agents of the invention is useful in methods to determine the status of cancer patients for the purpose of gelsolin replacement therapy. For example, gelsolin level in a cancer patient may be assessed to determine if the gelsolin level is decreased relative to a control reference standard. If the level of serum gelsolin in the patient is lower than the control reference standard, then the patient may be classified as an individual in need of gelsolin replacement therapy. Further, the gelsolin binding agents of the invention may be used to determine the level of gelsolin to be dosed to the patient based on the level of plasma gelsolin. Moreover, the gelsolin binding agents of the invention may be used to measure the subsequent response of a patient to gelsolin replacement therapy by measuring serum gelsolin level after treatment of the patient.

Example 9

Effect of Chemotherapy on Plasma Gelsolin Levels

1. Effect of Chemotherapy on Plasma Gelsolin in an In Vivo Murine Model

Figure 15A:
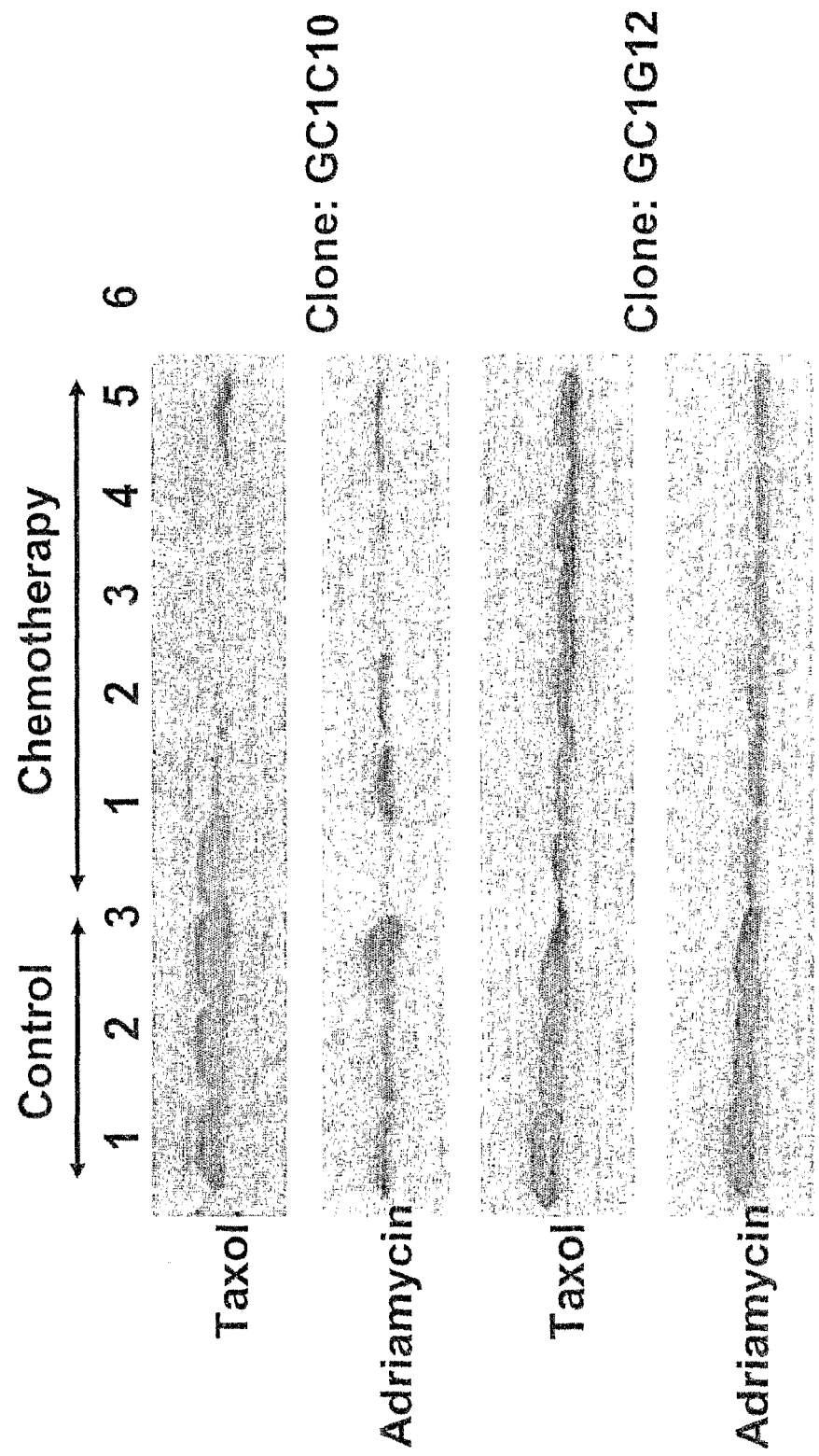
FIG. 15A is a photograph of western blot and FIG. 15B is a quantitative analysis of the western blot by densitometry.
Figure 15B:
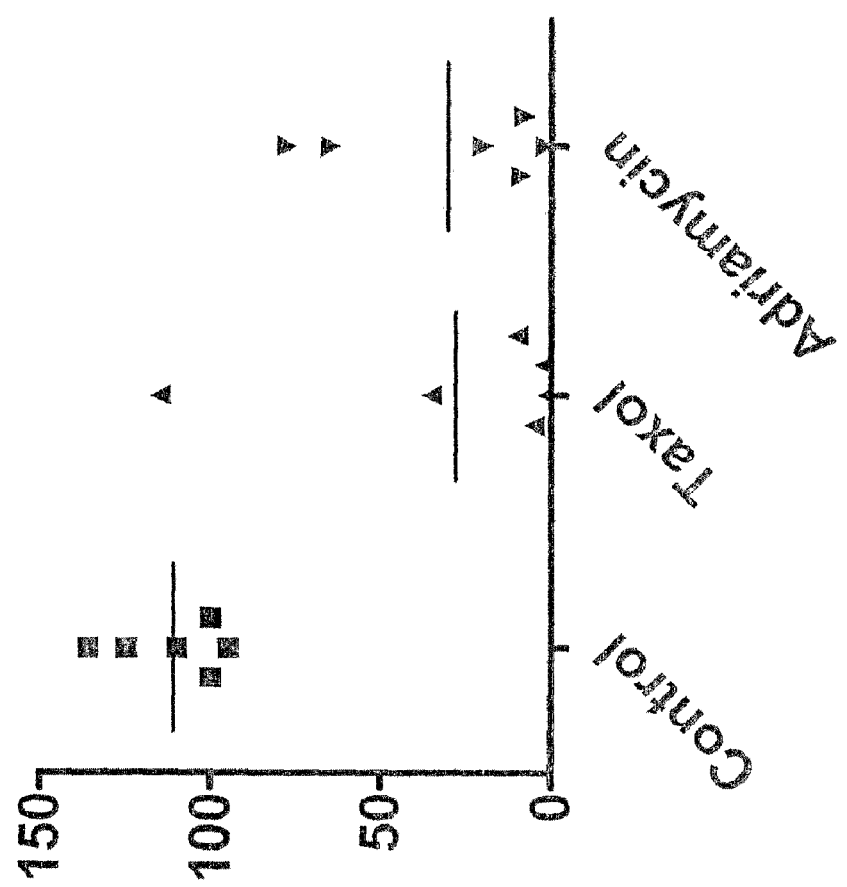

The effects of chemotherapy on plasma gelsolin were investigated using the binding agents of the present invention. The chemotherapeutic agents taxol (Taxol, Mayne Pharma Pty Ltd, Mulgrave VIC 3170 Australia) or adriamycin (Adriamycin, Ben Venue Laboratories, Inc. Bedford, Ohio 4414) were administered by i.p. injection (250 μg per dose) into mice (8 week-old female Balb/c purchased from Animal Facility of Chinese Academy of Medical Sciences). The agent was administered two times every other day. At three days after the last injection, serum was collected from the mice and analyzed by western blot using anti-gelsolin antibodies GC1C10 and GC1G12 (using procedures described above). Antibody GC1G12 cross-reacts with murine gelsolin. The results are shown in FIG. 15 (Panels A and B). Each lane in panel A represents a different subject mouse. The western blot data of panel A (FIG. 15A) was quantitatively measured by densitometry (FIG. 15B). The results indicate that chemotherapy treatment using either taxol or adriamycin significantly decreases the levels of detectable serum gelsolin in mice administered such therapy.

Figure 16B:
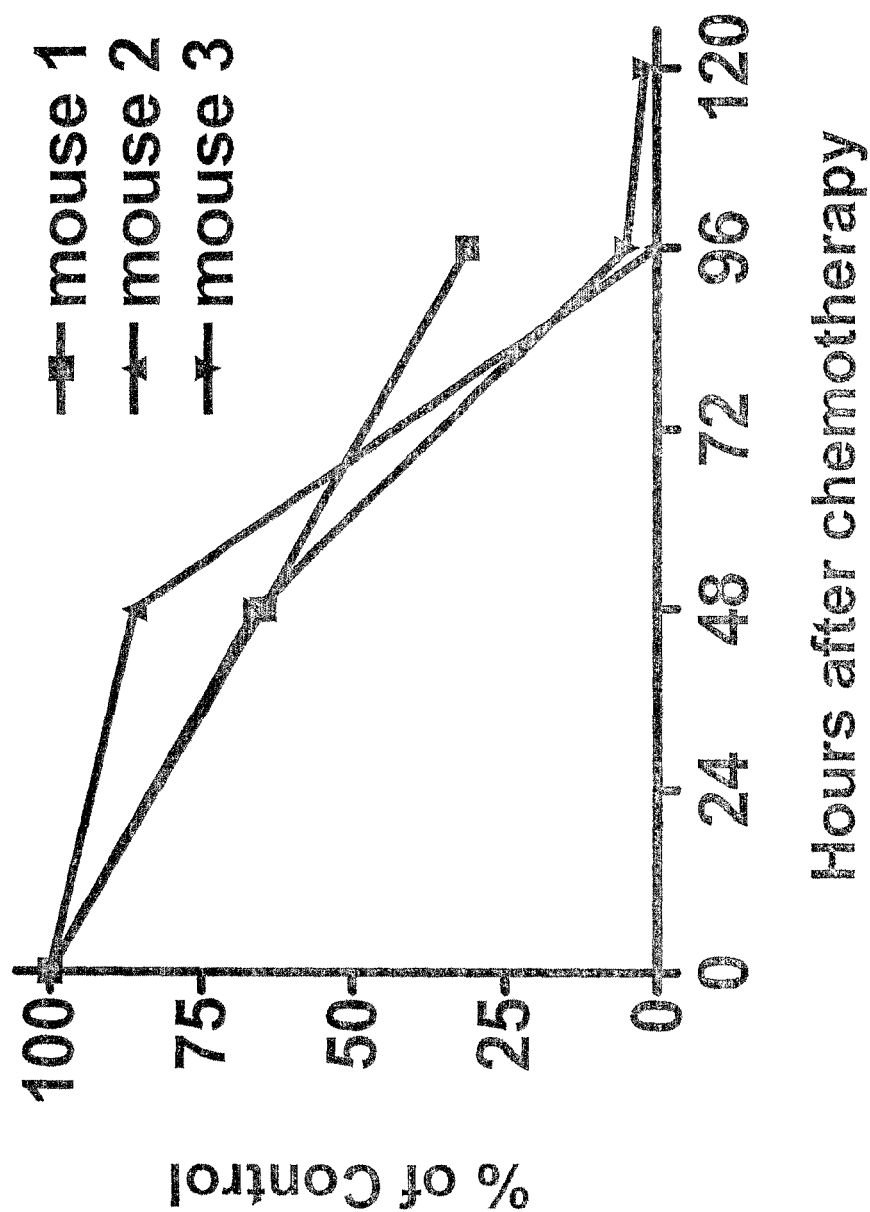
FIG. 16B is a quantitative analysis of the western blot of FIG. 16A by densitometry.
Figure 16C:
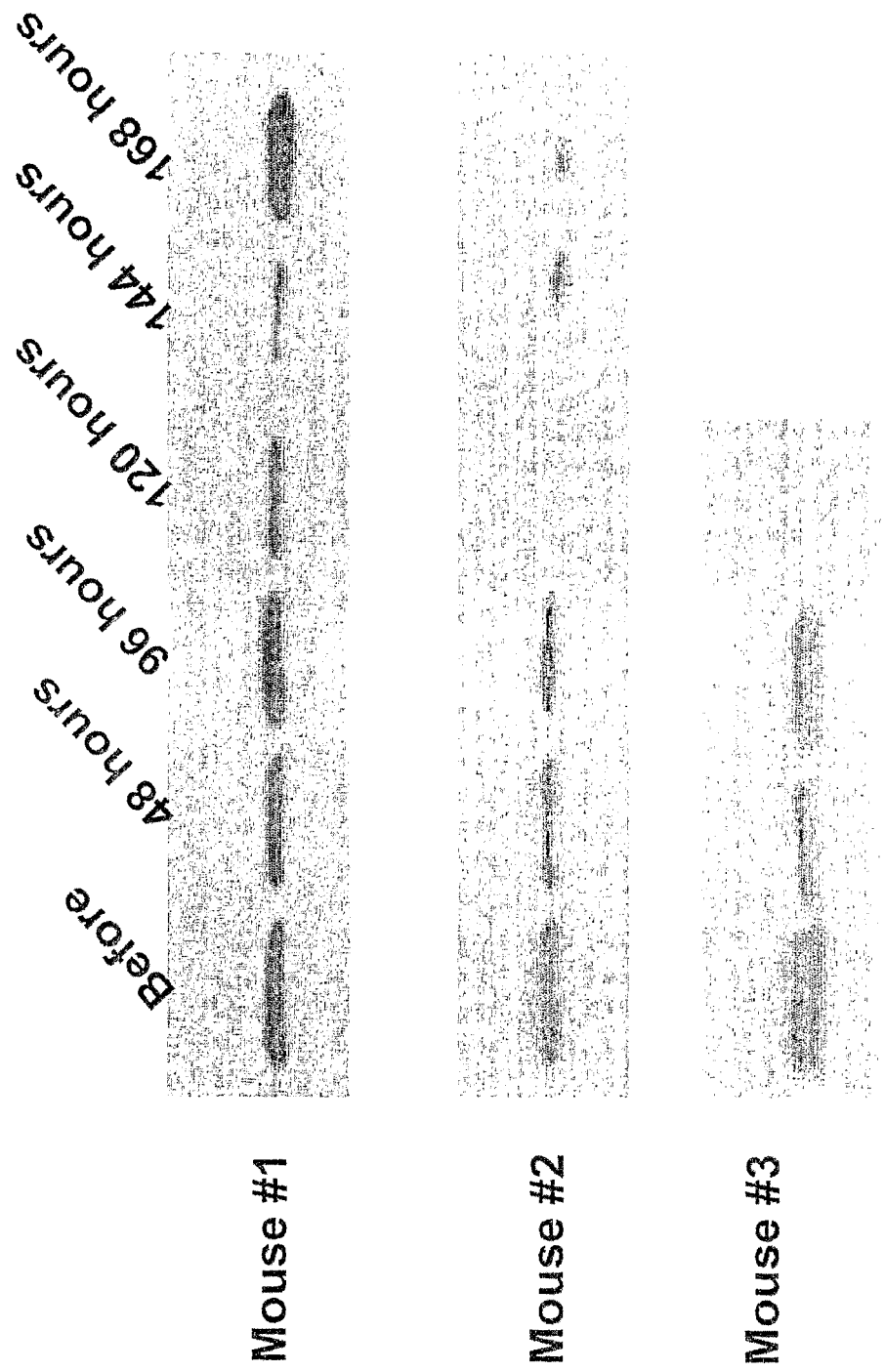
FIG. 16C is a photograph of a western blot of serum samples of mice at various time points after receiving Taxol.

To examine the time-dependent decrease of plasma gelsolin after chemotherapy, mice (8 week-old female Balb/c purchased from Animal Facility of Chinese Academy of Medical Sciences) were i.p. injected with a high dose of taxol (500 μg per dose) or adriamycin (500 μg per dose), as a single bolus injection. Serum levels of gelsolin were measured at the indicated time point after treatment using western blot analysis with anti-gelsolin antibody GC1G12 (as described above). FIG. 16A shows the western blot, and FIG. 16B shows quantitation of the western blot using densitometry. As shown in FIGS. 16A and 16B, a time-dependent decrease of serum gelsolin after taxol treatment was observed. Likewise, as shown in FIGS. 16C and 16D, the time-dependent decrease of serum levels of gelsolin after adriamycin treatment was observed. Thus, chemotherapy depletes plasma gelsolin in a murine model and plasma gelsolin levels may serve as a biomarker for the acute toxic response of chemotherapy. As such, the gelsolin binding agents of the invention are useful to monitor patient condition following chemotherapy or to ascertain whether gelsolin replacement therapy, or further chemotherapy, might be appropriate. Further, the gelsolin binding agents of the invention may be used to determine the level of gelsolin to be dosed to the patient based on the level of plasma gelsolin. Moreover, the gelsolin binding agents of the invention may be used to measure the subsequent response of a patient to gelsolin replacement therapy by measuring serum gelsolin level after treatment of the patient.

2. Effect of Chemotherapy on Plasma Gelsolin in Humans

Figure 17:
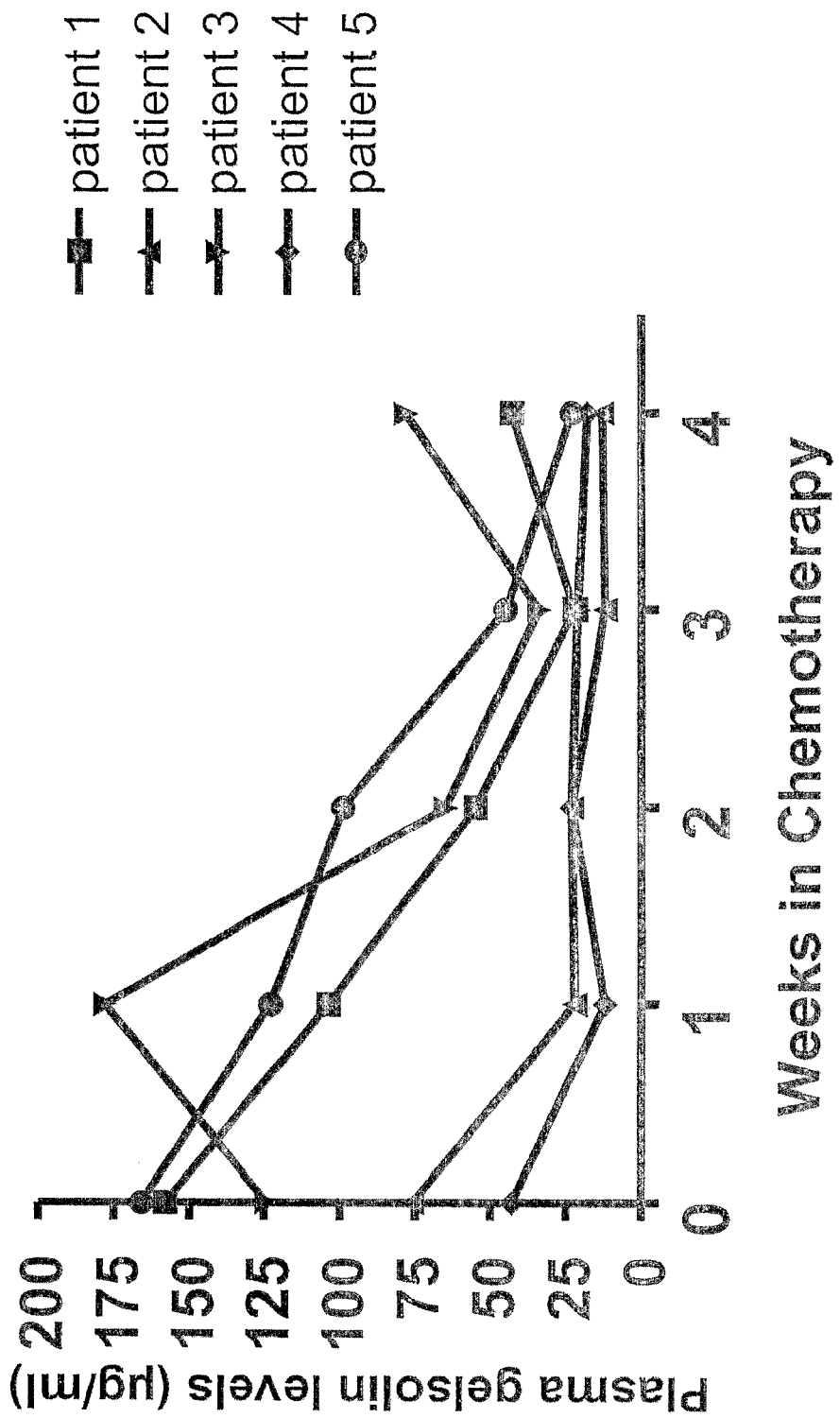
FIG. 17 is a graph showing plasma gelsolin levels of five patients in chemotherapy, a time-dependent decrease in a group of patients with ovarian cancer after cisplatin chemotherapy as determined using a gelsolin ELISA assay of the invention.

Serum levels of gelsolin in five (5) human patients with ovarian cancer were measured by ELISA using GN3E9/GC1C10 antibody pair (as described above) before and after chemotherapy. Specifically, human subjects with stage III/IV ovarian cancer received paclitaxel 185 mg/m2 IV over 3 hours and cisplatin at a dose of 75 mg/m2 every three weeks as chemotherapy. The results are shown in FIG. 17. All patients showed significantly decreased levels of gelsolin at three weeks after chemotherapy. Consistent with the results in the murine model, chemotherapy depletes plasma gelsolin in humans and plasma gelsolin levels may serve as a biomarker for the acute toxic response to chemotherapy. As such, the gelsolin binding agents of the invention are useful to monitor patient condition following chemotherapy or to ascertain whether gelsolin replacement therapy, or further chemotherapy, might be appropriate. Further, the gelsolin binding agents of the invention may be used to determine the level of gelsolin to be dosed to the patient based on the level of plasma gelsolin. Moreover, the gelsolin binding agents of the invention may be used to measure the subsequent response of a patient to gelsolin replacement therapy by measuring serum gelsolin level after treatment of the patient.

Example 10

Gelsolin Replacement Therapy

The effect of gelsolin replacement therapy on body weight and percent survival of mice (8 week-old female Balb/c purchased from Animal Facility of Chinese Academy of Medical Sciences) following chemotherapy was examined. In this experiment, mice were administered two doses of 250 μg adriamycin every other day by i.p. injection. One day following the last dose of adriamycin, the mice in the test group were provided a supplement of 100 μg recombinant full-length gelsolin by ip injection. The gelsolin supplements were repeated every other day for total of three doses. The body weight and percent survival of the mice following chemotherapy and gelsolin replacement therapy are shown in FIG. 18. The results indicate that providing gelsolin results in 100% survival of the mice after 10 days, whereas mice not provided gelsolin exhibit 100% mortality after 10 days. Likewise, the decrease in body weight for mice provided gelsolin replacement therapy was not as severe as mice not provided such therapy. Thus, supplementing subjects with gelsolin during chemotherapy reduces chemotherapy-induced acute toxic response and mortality. As such, the gelsolin binding agents of the invention are useful to monitor patient condition following chemotherapy or to ascertain whether gelsolin replacement therapy, or further chemotherapy, might be appropriate. Further, the gelsolin binding agents of the invention may be used to determine the level of gelsolin to be dosed to the patient based on the level of plasma gelsolin. Moreover, the gelsolin binding agents of the invention may be used to measure the subsequent response of a patient to gelsolin replacement therapy by measuring serum gelsolin level after treatment of the patient.

Example 11

Immunoaffinity Purification of Native Gelsolin from Plasma

1. Affinity-purification of Plasma Gelsolin

Figure 19:
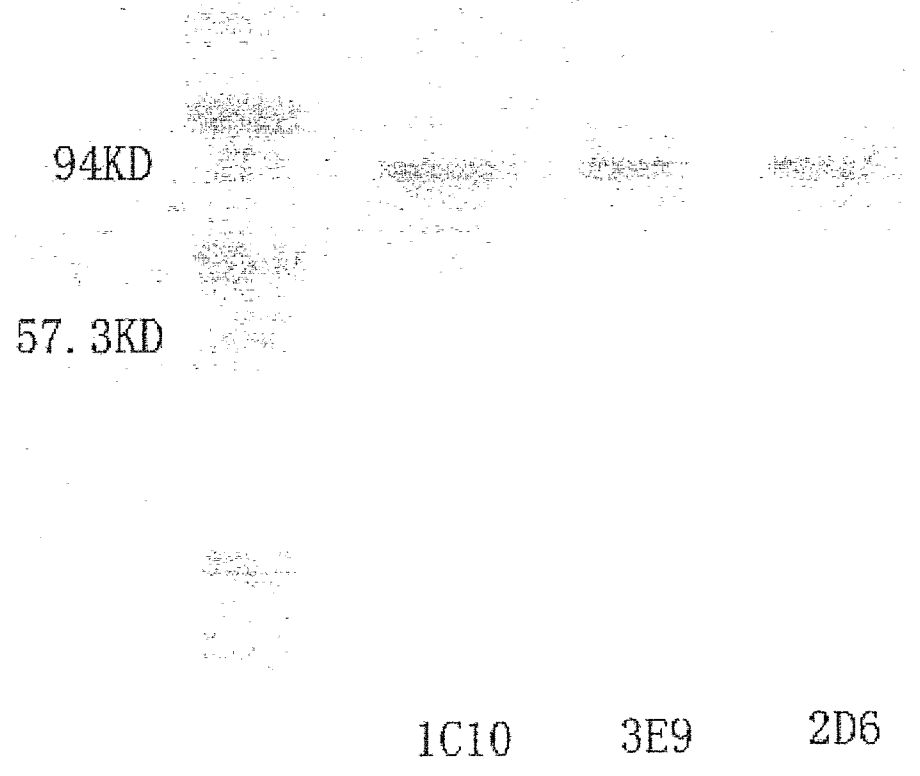

The ability of the selected antibodies of the present invention to bind to actin-free gelsolin in plasma suggests that these antibodies may have utility for purification of native and functional form of gelsolin from human plasma. To test this possibility, highly purified anti-gelsolin antibodies (Protein A or Protein G affinity purified by standard techniques), GN3E9, GF2D6, or GC1C10 were immobilized to Sepharose 4B and used for affinity purification of human plasma gelsolin. The immobilization of anti-gelsolin antibodies to Sepharose 4B was carried out as described in Example 3 above. For affinity purification of plasma gelsolin, 10 ml of pooled human plasma (at least 20 subjects) was passed through a 2 ml column containing antibody (e.g., anti-gelsolin antibody, GN3E9, GF2D6, or GC1C10)-immobilized beads at a flow rate of 2 ml per minute. After plasma samples were passed through each immunoaffinity column, unbound material was washed from the columns with 50 ml PBS. The protein bound to each of the gelsolin affinity columns was eluted with elution buffer (0.1 M glycine (pH 2.4), 0.15 M NaCl). The optical density of each eluted fraction (1 ml) was measured at OD280 nm. The fractions having an OD280>0.1 units were collected. The pH After addition of 100 μl of neutralization buffer (1M Tris-HCl pH 8.5), the eluates were placed separately in dialysis tubing, and the eluates dialyzed against 1 L of PBS (pH 7.5) at 4° C. The dialysis buffer was changed twice. The purified protein was concentrated to 1 mg/ml using a centricon filtration apparatus by standard technique. The concentrated sample was sterilized by passage through a 0.22 μm filter and then stored at 4° C. until use. The protein purity was examined by 10% SDS-PAGE as summarized in FIG. 19 by procedures described above. FIG. 19 shows the results of the fractionation of affinity-purified human plasma gelsolin using beads conjugated to anti-gelsolin antibodies GC1C10, GN3EP, and GN2D6, respectively, by 10% SDS-PAGE and Coomassie Blue staining. Gels were stained with Coomassie Blue at room temperature for 30 minutes and then destained with 50% (v/v) methanol and 10% (v/v) acetic acid. Consistent with the immunoprecipitation studies presented in Example 3, anti-gelsolin antibodies GN3E9, GF2D6, or GC1C10 bound immunoreactive polypeptide which migrated as an ~90 kDa polypeptide on SDS-PAGE. The migration of the ~90 kDa anti-gelsolin antibody immunoreactive polypeptide is consistent with the expected migration of full-length gelsolin polypeptide from human serum sample. The identity of this ~90 kDa polypeptide has been confirmed to be full-length gelsolin polypeptide by mass spectroscopy analysis (See Example 4). The purity of the immunopurified full-length gelsolin polypeptide was greater than 90% as determined by densitometry analysis of the SDS-PAGE gel. As such, the gelsolin binding agents (e.g., anti-gelsolin antibodies GN3E9, GF2D6, or GC1C10) are useful in methods of purifying native human gelsolin from human serum. Likewise, these gelsolin binding agents are useful in methods to purify immunoreactive gelsolin (e.g., native gelsolin and recombinant gelsolin as well as fragments and homologs, thereof) from a biological sample.

2. Comparison of the Biological Activity of Affinity-purified, Native Form of Gelsolin with Recombinant Gelsolin Using Gelsolin Binding Agents of the Invention Native plasma gelsolin human gelsolin was immunoaffinity purified using an anti-gelsolin antibody of the invention by procedures essentially as described above (Example 11, section 1). Full-length recombinant human gelsolin was purified using a Ni-NTA superflow column (Qiagen, Valencia, Calif.) according to manufacturer's instructions (See Example 1). The biological activity of gelsolin test preparations was determined in vitro in an F-actin severing assay. Briefly, F-actin was incubated with immunoaffinity gelsolin (native or recombinant) at room temperature and the proportion of actin in the supernatant (G-actin) versus the pellet (F-actin) was compared to a control reaction without gelsolin. The biological activity of gelsolin was defined by the amount or concentration of gelsolin required to solubilize 50% of the F-actin in 5 min. As the amount of gelsolin needed to reach this threshold increases, the less biologically active that sample of gelsolin is compared to other gelsolin samples that require a lesser amount to achieve the same level of actin cleavage per 5 min.

Specifically, the biological activity of affinity-purified human plasma gelsolin (native plasma gelsolin) was compared to that of recombinant full-length human gelsolin by F-actin severing assay (Cytoskeleton Inc, Denver, Colo.). Gelsolin was diluted in the reaction buffer (50 mM Tris, pH 7.5, containing 0.1 mM $CaCl_2$, 0.1 mM $MgCl_2$, 30 mM NaCl, 1 mM DTT). F-actin substrate was prepared from rabbit muscle actin by diluting the actin in 0.5 mg/ml in general actin buffer (5 mM Tris, pH 8.0, containing 0.2 mM $CaCl_2$), and incubated the mixture on ice for 30 min. The mixture was clarified by centrifugation (14,000 rpm, 15 min) and the supernatant containing G-actin was retained. One tenth (1/10) volume of actin polymerization buffer (500 mM KCl containing 20 mM $CaCl_2$ and 10 mM ATP) was then added to the supernatant and this mixture was incubated at room temperature for 1 h to form F-actin. This F-actin preparation was used as substrate in test reactions to determine gelsolin F-actin severing activity. Gelsolin-mediated F-actin severing activity was measured by incubating 5 μg F-actin preparation in the presence of varying concentrations of gelsolin test preparation (0-0.1 mg/ml) in 100 μl of reaction buffer. Test mixtures were incubated at room temperature for 5 min and then centrifuged at 100,000×g for 1 h. The pellets containing F-actin were dissolved in SDS-PAGE sample buffer. The supernants containing G-actin were removed and precipitated with 20% TCA, and the pellets were dissolved in SDS-PAGE sample buffer. Both F-actin and G-actin were separated in 10% SDS-PAGE and stained with Coomassie Blue (as detailed above). The ratio of F-actin versus G-actin was determined by densitometry. The results are summarized in Table 21 below.

TABLE 21

F-actin severing activity of the affinity-purified gelsolin

| gelsolin | % of F-actin | | | |
|---|---|---|---|---|
| | 0 | 0.1 mg/ml | 0.5 mg/ml | 1.0 mg/ml |
| Immunoaffinity-purified human native plasma gelsolin | 74 | 35 | 21 | 12 |
| Full-length human recombinant gelsolin | 75 | 68 | 55 | 19 |

As shown in Table 21, the anti-gelsolin antibody of the present invention is useful to purify biologically active human native plasma gelsolin using methods of the present invention. Use of the gelsolin binding agents of the invention to purify human native plasma gelsolin is advantageous as the methods of the invention yield a purified human native plasma gelsolin preparation with greater biological activity compared with full-length human recombinant gelsolin purified by Ni-NTA affinity chromatography as evidenced by F-actin severing activity summarized in Table 21. Gelsolin preparations with greater biological activity may be more efficacious when administered to a subject in need of gelsolin replacement when compared with administration of gelsolin preparation with lower biological activity. Using gelsolin preparations of greater biological activity may be administered at lower dosages to achieve the same therapeutic benefit to a subject. This lower dosage may minimize potential for adverse side-effects of gelsolin replacement therapy (e.g., immunological reaction or cytotoxicity)

The biological activity of gelsolin can also be determined by in vivo assay by evaluation of the efficacy of prevention of chemotherapy-induced acute toxicity as described below. Mice are treated with sub-lethal doses of adriamycin, and injected with gelsolin. The body weight loss and mortality are used for evaluation of the therapeutic efficacy of affinity-purified gelsolin. An increase in body weight loss or mortality in subjects receiving the gelsolin relative to subject that do not receive gelsolin indicates that the gelsolin preparation is biologically active.

Example 12

Characterization of 50 kDa Gelsolin-Like Polypeptide

1. Specificity of Binding Agents for Gelsolin and Gelsolin-like Polypeptides

Figure 20:
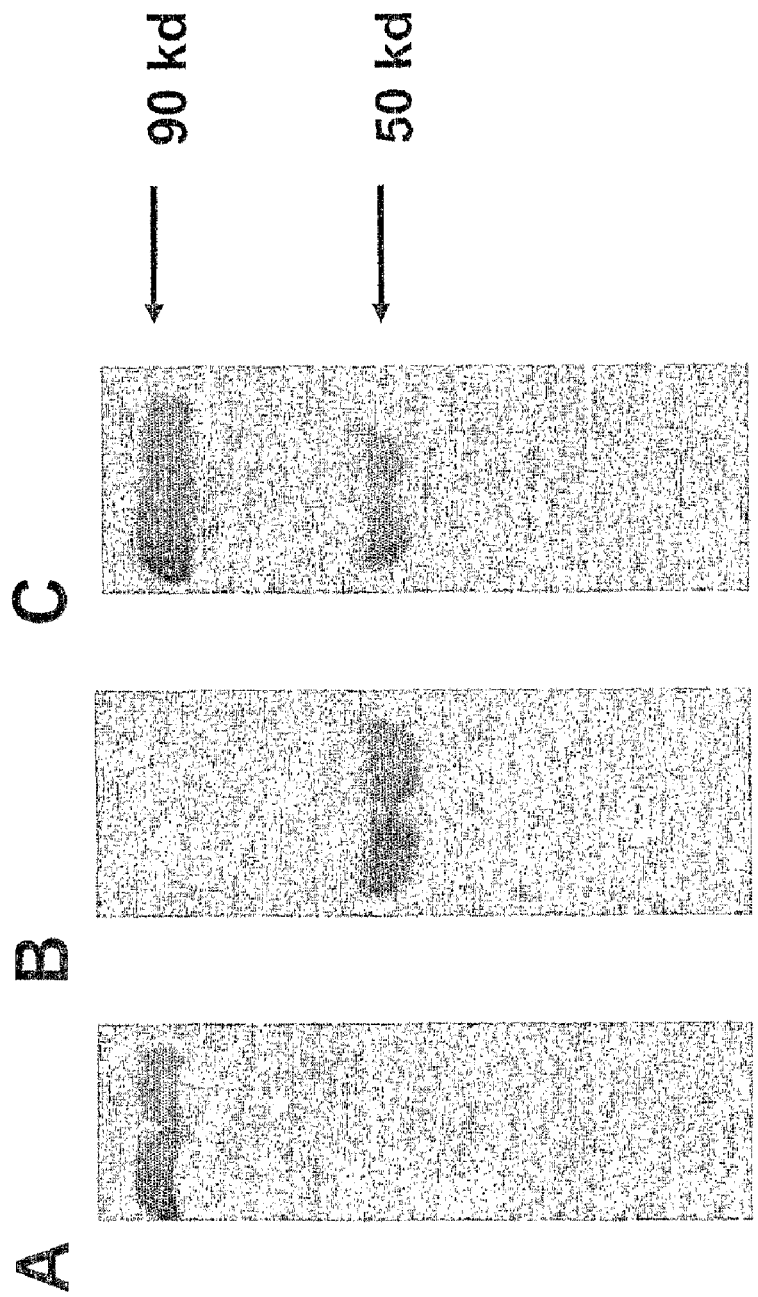
FIG. 20 is a western blot analysis of different forms of human plasma gelsolin with three representative anti-gelsolin antibodies. Panel A is a representative of a group of antibodies that only react with 90 kDa form of human plasma gelsolin (FIG. 20A). Panel B is a representative of a group of antibodies that only reacts with the 50 kDa gelsolin-like polypeptide (FIG. 20B). Panel C is representative of a group of antibodies that reacts with both 90 kDa and 50 kDa immunoreactive forms (FIG. 20C).

A panel of anti-gelsolin antibodies raised against various immunogens were tested for their ability to detect more than one immunoreactive gelsolin-like polypeptide in a western blot. Western blot analysis was carried out as in Example 3 above. The results are shown in Table 22. Five antibodies that were obtained from mice immunized with native plasma gelsolin only recognize a 50 kDa gelsolin-like polypeptide (for example, see FIG. 20B). Six of the antibodies raised against full-length recombinant gelsolin only detect a 90 kDa polypeptide (for example, see FIG. 20A) and 4 of them detect both a 90 and 50 kDa polypeptide (for example, see FIG. 20C). The antibodies raised against the N-terminal fragment of gelsolin only react with a 90 kDa polypeptide and none of them recognize a 50 kDa polypeptide. The antibodies raised against the C-terminal fragment show varying reactivity profiles. Four out of twelve clones recognized a 90 kDa polypeptide, two out of 12 detect the 50 kDa polypeptide, and 6 out of 12 clones react with both of the 90 and 50 kDa polypeptides. FIG. 20 is a western blot showing the representative results of three different categories of antibodies with different detection profiles.

TABLE 22

Frequency of antibodies recognizing different forms of plasma gelsolin

| Antibodies raised against | 90 kDa only | 50 kDa only | 90 kDa and 50 kDa |
|---|---|---|---|
| Native gelsolin (NG) | 0/5 | 5/5 | 0/5 |
| Full-length recombinant (GF) | 6/10 | 0/10 | 4/10 |
| N-terminal fragment (NG) | 4/4 | 0/4 | 0/4 |
| C-terminal fragment (GC) | 4/12 | 2/12 | 6/12 |

Gelsolin binding agents of the invention are useful in immunometric methods (e.g., ELISA; RIA; western blot) which selectively measure full length gelsolin immunoreactive polypeptide and/or 50 kDa gelsolin-like immunoreactive polypeptide.

2. The 50 kDa Gelsolin-like Polypeptide is Present in Apoptotic Cells

Figure 21:
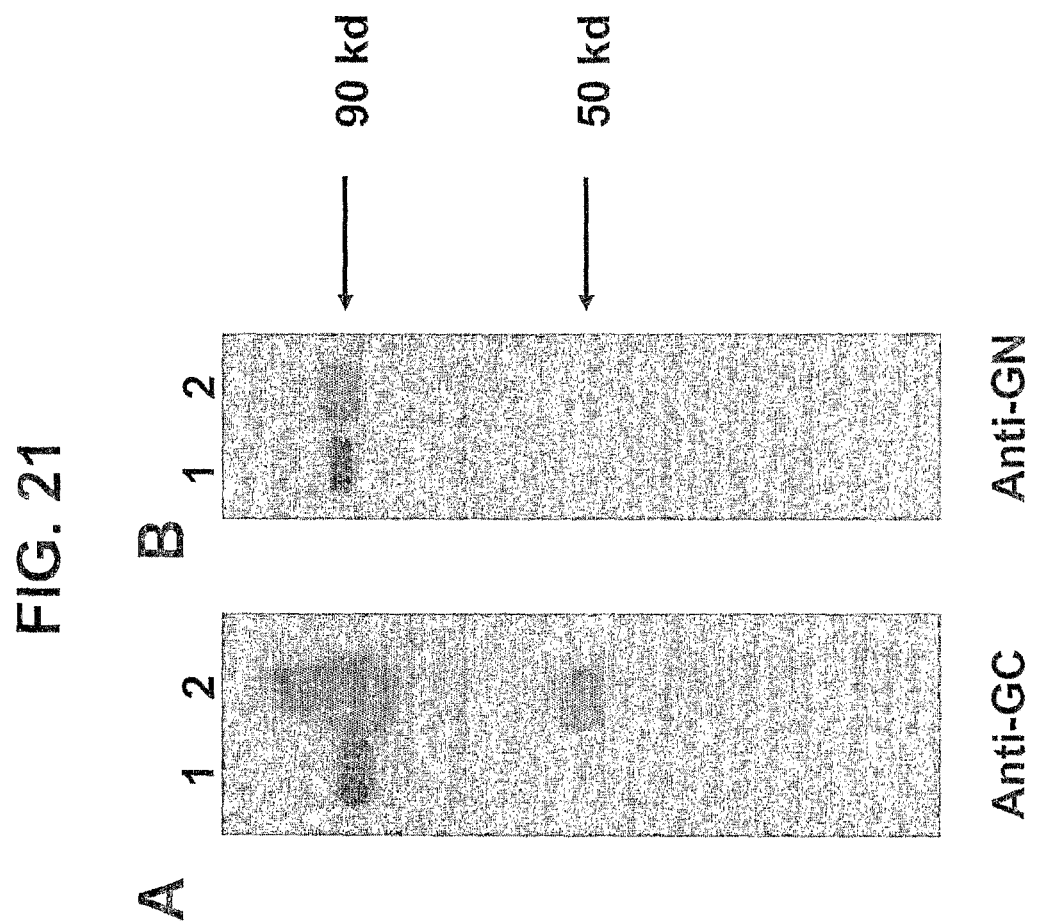
FIG. 21 is a western blot analysis of intracellular gelsolin of a human pancreatic cancer cell line with or without apoptosis with anti-gelsolin antibodies. Human pancreatic cancer cells, MIAcapa, cultured in control medium (lane 1) or in the presence of 1000 ng/ml of anti-DR5 antibody (CTB006) for four hours (lane 2). The western blot of total cell lysates was probed with a gelsolin C-terminal fragment specific antibody GC1C10 (FIG. 21A) or a gelsolin N-terminal fragment specific antibody GN3E9 (FIG. 21B).

It has been reported that caspase 3 cleaves gelsolin during apoptosis (Sun et al., *J Biol Chem.* 274: 33179-33182 (1999)). Therefore, the 50 kDa gelsolin-like immunoreactive polypeptide may be derived from the cleavage of full length gelsolin by caspase 3. FIG. 21 is a western blot analysis of cellular gelsolin with anti-gelsolin antibodies comparing control and apoptotic cells. Lane 1 comprises control MIA-capa cells (pancreatic cancer cells) and Lane 2 are cells treated with CTB006-antibodies. CTB006 is a murine monoclonal antibody directed to the TRAIL-R2 receptor. This antibody induces apoptosis of tumor cells that express TRAIL-R2 receptor. The results indicate that increased levels in intracellular gelsolin (full length, 90 kDa) are associated with induction of apoptosis, suggesting that gelsolin is a stress-inducible protein. Moreover, a 50 kDa immunoreactive fragment is specifically associated apoptotic cells, suggesting that the 50 kDa protein observed in plasma may be a cleaved product of the full-length gelsolin.

3. Serum Gelsolin Profile in Cancer Patients

Figure 22:
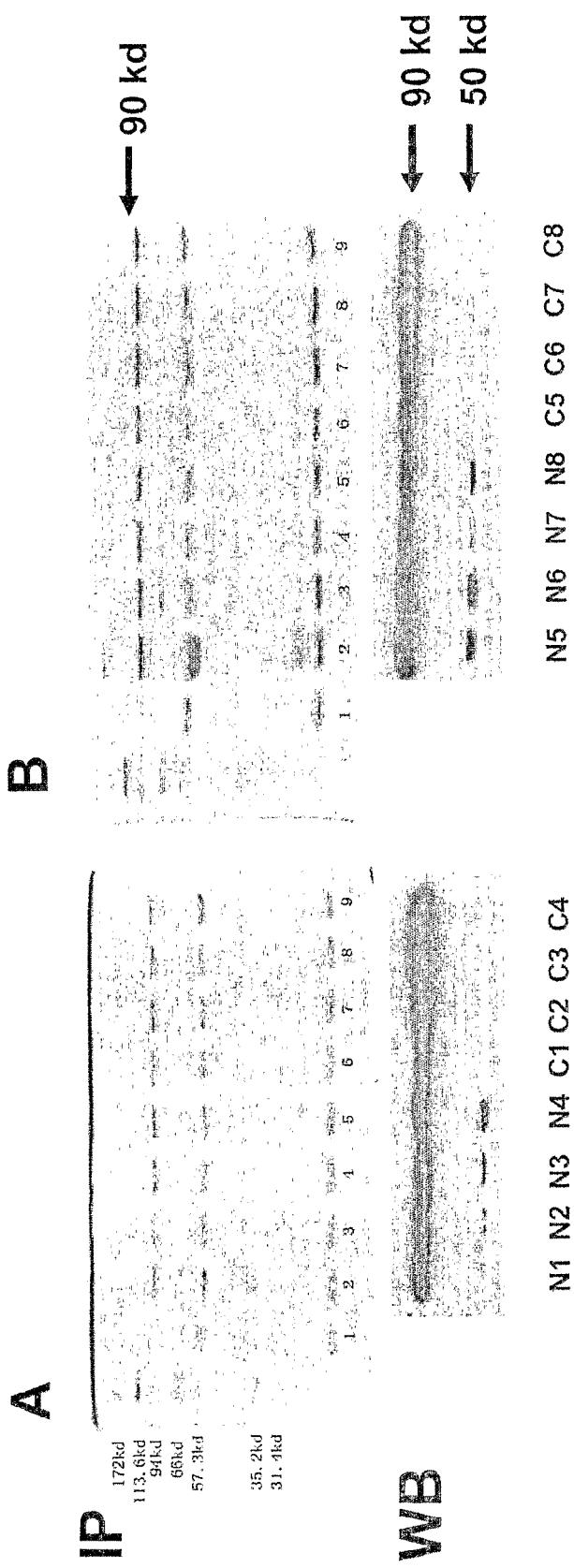
FIG. 22 is an SDS-PAGE analysis of immunoprecipitated plasma gelsolin (top panel) and a western blot analysis (lower panel) of total plasma gelsolin in a first study of 4 healthy control patients (N1 to N4) and 4 patients with cancer (C1 to C4) (FIG. 22A) and a second study of 4 healthy control patients (N5 to N8) and 4 patients with cancer (C5 to C8) (FIG. 22B).

To further examine the clinical significance of the serum profile of gelsolin, the two immunoreactive forms of gelsolin were measured in 8 healthy controls (N1-N8) and 8 cancer patients (C1-C8) by immunoprecipitation and western blot analysis using the anti-gelsolin antibody GC1C10 using procedures described above. As shown in FIG. 4, anti-gelsolin antibody GC1C10 was only able to precipitate the 90 kDa protein. Thus, while anti-gelsolin antibody C1C10 is able to recognize the 50 kDa immunoreactive gelsolin-like protein in a western blot, it is not able to immunoprecipitate the shorter form (i.e., 50 kDa immunoreactive polypeptide) of gelsolin in an immunoprecipitation assay. Western blot analysis of total serum samples shows that GC1C10 detects two forms of gelsolin in serum samples of healthy controls, but not in cancer patients (FIG. 22), indicating that the 50 kDa form may be a biomarker for cancer or the status of cancer patients.

Specifically, a decrease in the 50 kDa plasma gelsolin-like polypeptide may indicate that a patient has cancer. Further, the studies demonstrate that gelsolin using gelsolin binding agents of the invention is useful to measure serum gelsolin and gelsolin-like polypeptide in biological sample from patients with cancer.

Example 13

Determination of the N-Terminal Amino Acid Sequences of the Heavy and Light Chains of Anti-Gelsolin Binding Agents of the Invention In order to obtain cDNAs of the heavy and light chains of GN3E9, GC1C10, and GF2D6, the N-terminal amino acid sequences of the heavy and light chains of GN3E9, GC1C10, and GF2D6 can be determined by known sequencing techniques. Five micrograms (5 μg) of the affinity-purified GN3E9, GC1C10, and GF2D6 are separated in 10% SDS-PAGE) under reducing conditions. After electrophoresis, the proteins in the gel are transferred to a polyvinylidene difluoride membrane ("PVDF"). After transfer, the PVDF membrane is washed with washing buffer 25 mM NaCl, 10 mM sodium borate buffer (pH 8.0), then stained in a staining solution (50% (v/v) methanol, 20% (v/v) acetic acid and 0.05% (w/v) Coomassie Brilliant Blue) for 5 min to locate the protein bands. The PVDF membrane is then destained with 90% (v/v) aqueous methanol and the bands corresponding to the heavy chain (the band with the lower mobility) and light chain (the band with the higher mobility) are excised and washed with deionized water. The N-terminal amino acid sequence of the heavy and light chains are determined by the Edman automated method using a protein sequencer (PRO-CISE 491, ABI, USA). The results are summarized in Table 23 (N/A=not available).

Using the techniques described above, the following N-terminal sequences were determined for select gelsolin binding agents of the invention.

TABLE 23

N-terminal sequences of antibodies

| Clone | Chains | Sequence | Seq ID |
|---|---|---|---|
| GN3E9 | Light chain | DIVMTQSPATLSVTPGDR | SEQ ID NO.: 44 |
| GC1C10 | Heavy chain | EVQLVESGGGLVKPG | SEQ ID NO.: 45 |
| GC1C10 | Light chain | DVQMTSPSXLT | SEQ ID NO.: 46 |

Equivalants

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

Other embodiments are set forth within the following claims.

---

What is claimed is:

1. An isolated antibody produced by a deposited hybridoma cell line selected from the group consisting of: CGMCC Accession Nos: 2114, 2115, and 2116, or antigen binding fragments thereof.

2. A method for determining presence or amount of gelsolin in a biological sample comprising:
   (a) contacting a biological sample with one or more antibodies produced by a deposited hybridoma cell line selected from the group consisting of: CGMCC Accession Nos: 2114, 2115, and 2116, or antigen-binding fragments thereof, under conditions wherein the one or more antibodies or fragments thereof specifically bind to gelsolin; and
   (b) detecting the presence or amount of the one or more antibodies or fragments thereof bound to the gelsolin, thereby determining the presence or amount of the gelsolin in the sample.

3. The method of claim 2, wherein the sample is contacted with the one or more antibodies or antigen-binding fragments thereof in an enzyme-linked immunosorbent assay (ELISA) comprising a detectable label.

4. The method of claim 3, wherein the step of contacting comprises binding a first of the one or more antibodies or fragments thereof to a substrate and contacting the sample and a second of the one or more antibodies or fragments thereof to the substrate, wherein the second antibody comprises the detectable label.

5. The method of claim 4, wherein the first antibody comprises the antibody produced by hybridoma cell line CGMCC Accession No: 2115, or the antigen-binding fragment thereof, and the second antibody comprises the antibody produced by the hybridoma cell line selected from the group consisting of CGMCC Accession No. 2114 and 2116, or the antigen-binding fragments thereof.

6. A method for determining presence of, or a predisposition to, a disease or condition associated with altered levels of a gelsolin polypeptide in a first mammalian subject, the method comprising the steps of:
   (a) providing a test sample from the first mammalian subject;
   (b) contacting the test sample from the first mammalian subject with one or more compounds that bind the gelsolin polypeptide to form a compound/gelsolin polypeptide complex, wherein each of the one or more compounds is an antibody produced by a hybridoma cell line selected from the group consisting of CGMCC Accession No. 2114, 2115, and 2116, or antigen-binding fragments thereof; and
   (c) detecting a level of compound/gelsolin polypeptide complex in the contacted test sample as indicative of a level of gelsolin polypeptide in the test sample; wherein an alteration in the level of the gelsolin polypeptide in the test sample as compared to a reference level indicates the presence of, or the predisposition to, the disease or condition in the first subject.

7. The method of claim 6, wherein the sample is contacted with the one or more antibodies or antigen-binding fragments thereof in an enzyme-linked immunosorbent assay (ELISA) comprising a detectable label.

8. The method of claim 7, wherein the step of contacting comprises binding a first of the one or more antibodies or fragments thereof to a substrate and contacting the sample and a second of the one or more antibodies or fragments thereof to the substrate, wherein the second antibody comprises the detectable label.

9. The method of claim 8, wherein the first antibody comprises the antibody produced by hybridoma cell line CGMCC Accession No: 2115, or the antigen-binding fragment thereof, and the second antibody comprises the antibody produced by the hybridoma cell line selected from the group consisting of CGMCC Accession No. 2114 and 2116, or the antigen-binding fragments thereof.

10. The method of claim 6, wherein the disease or condition associated with altered levels of gelsolin is selected from the group consisting of: septic shock, multiple organ dysfunction syndrome, rheumatoid arthritis, stroke, heart infarction, cancer, systemic autoimmune disease, chronic hepatitis, side-effects of chemotherapy, and side-effects of radiation therapy.

11. The method of claim 6 wherein the first mammalian subject is suspected of having septic shock, the reference standard comprises a control subject not having septic shock, and wherein a decrease in the level of gelsolin polypeptide in the test sample of the first subject compared to the reference standard indicates that the first subject has septic shock.

12. The method of claim 6 further comprising the steps of:
   comparing the level of gelsolin polypeptide in the test sample of the first subject to a reference standard level that comprises a control mammalian subject not having a disease or condition affecting gelsolin levels, and
   selecting to include the first subject with the alteration in the level in a clinical trial.

13. The method of claim 6 further comprising the steps of:
   assigning the first subject with the altered level of gelsolin polypeptide in the test sample to a subject class; and
   selecting a prophylactic or therapeutic treatment for the subject class.

* * * * *